(12) United States Patent
Lambert

(10) Patent No.: US 10,159,495 B1
(45) Date of Patent: Dec. 25, 2018

(54) DRILL BIT FOR A HANDHELD SURGICAL INSTRUMENT

(71) Applicant: Stryker Corporation, Kalamazoo, MI (US)

(72) Inventor: Trevor Jonathan Lambert, Portage, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 0 days.

(21) Appl. No.: 15/887,507

(22) Filed: Feb. 2, 2018

Related U.S. Application Data

(60) Provisional application No. 62/548,357, filed on Aug. 21, 2017.

(51) Int. Cl.
*A61B 17/16* (2006.01)

(52) U.S. Cl.
CPC ........ *A61B 17/1615* (2013.01); *A61B 17/162* (2013.01); *A61B 17/1624* (2013.01); *A61B 17/1637* (2013.01)

(58) Field of Classification Search
CPC .............. A61B 17/1615; A61B 17/162; Y10T 279/17136; Y10T 279/17153; Y10T 279/17427; Y10T 279/17786
See application file for complete search history.

(56) References Cited

U.S. PATENT DOCUMENTS

| 3,837,661 | A | * | 9/1974 | Phillippi | ................. | B23B 31/14 |
| | | | | | | 279/131 |
| 5,499,984 | A | | 3/1996 | Steiner et al. | | |
| 6,382,977 | B1 | | 5/2002 | Kumar | | |
| 6,394,806 | B1 | | 5/2002 | Kumar | | |
| 6,562,055 | B2 | | 5/2003 | Walen | | |
| 6,665,948 | B1 | | 12/2003 | Kozin et al. | | |
| 6,783,533 | B2 | | 8/2004 | Green et al. | | |
| 7,060,071 | B2 | | 6/2006 | Steiger | | |

(Continued)

FOREIGN PATENT DOCUMENTS

| WO | 0166024 A1 | 9/2001 |
| WO | 2017040783 A1 | 3/2017 |

OTHER PUBLICATIONS

English language abstract for WO 01/66024 extracted from espacenet.com database on Mar. 1, 2018, 2 pages.

*Primary Examiner* — Zade Coley
*Assistant Examiner* — Olivia C Chang
(74) *Attorney, Agent, or Firm* — Howard & Howard Attorneys PLLC

(57) ABSTRACT

A drill bit comprises a shank extending along an axis and an interface comprising at least one outermost drive portion spaced at a first interface distance from the axis. The drill bit further comprises a resilient arm extending from a proximal end of the shank. The resilient arm comprises an outer arm surface facing away from the axis and a retention surface facing toward a distal end of the shank. The retention surface may be radially aligned about the axis with respect to the outermost drive portion. The resilient arm is movable between: a first position where the outer arm surface is spaced from the axis at a first arm distance greater than the first interface distance, and a second position where the outer arm surface is spaced from the axis at a second arm distance less than or equal to the first interface distance.

29 Claims, 47 Drawing Sheets

(56) References Cited

U.S. PATENT DOCUMENTS

| | | | |
|---|---|---|---|
| 8,641,674 | B2 | 2/2014 | Bobroff et al. |
| 8,821,493 | B2 | 9/2014 | Anderson |
| 8,894,654 | B2 | 11/2014 | Anderson |
| 8,936,468 | B2 | 1/2015 | Ranck et al. |
| 8,970,207 | B2 | 3/2015 | Baumgartner |
| 8,974,227 | B2 | 3/2015 | Magnusson et al. |
| 9,204,885 | B2 | 12/2015 | McGinley et al. |
| 9,326,832 | B2 | 5/2016 | Zuker et al. |
| 9,358,016 | B2 | 6/2016 | McGinley et al. |
| 9,370,372 | B2 | 6/2016 | McGinley et al. |
| 9,566,121 | B2 | 2/2017 | Staunton et al. |
| 2009/0326537 | A1 | 12/2009 | Anderson |
| 2011/0245833 | A1 | 10/2011 | Anderson |
| 2014/0371752 | A1 | 12/2014 | Anderson |
| 2015/0066030 | A1 | 3/2015 | McGinley et al. |
| 2015/0066035 | A1 | 3/2015 | McGinley et al. |
| 2015/0066036 | A1 | 3/2015 | McGinley et al. |
| 2015/0066037 | A1 | 3/2015 | McGinley et al. |
| 2015/0066038 | A1 | 3/2015 | McGinley et al. |
| 2015/0080966 | A1 | 3/2015 | Anderson |
| 2016/0128704 | A1 | 5/2016 | McGinley et al. |
| 2016/0157871 | A1* | 6/2016 | Overes ............... A61B 17/16 29/428 |
| 2016/0278802 | A1 | 9/2016 | Cihak et al. |

* cited by examiner

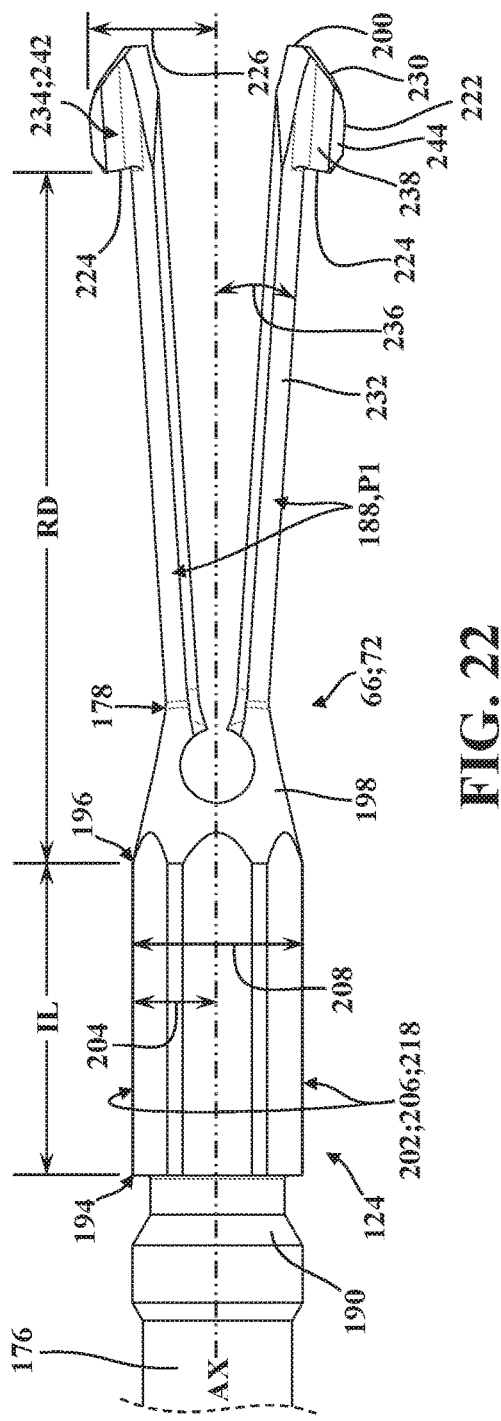
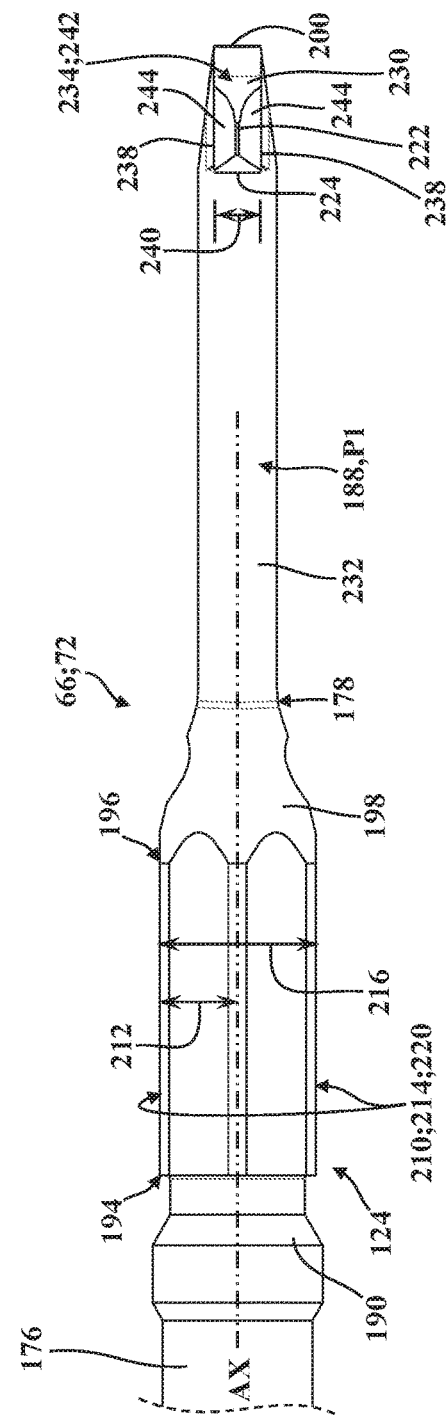
FIG. 22
FIG. 23

DRILL BIT FOR A HANDHELD SURGICAL INSTRUMENT

CROSS-REFERENCE TO RELATED APPLICATION

The subject patent application claims priority to and all the benefits of U.S. Provisional Patent Application No. 62/548,357 which was filed on Aug. 21, 2017, the disclosure of which is hereby incorporated by reference in its entirety.

TECHNICAL FIELD

The present invention relates, generally, to surgical instruments and, more particularly, to a drill bit for a handheld surgical instrument, a tip protector for attaching the drill bit to the surgical instrument, and a release mechanism for removing the drill bit from the surgical instrument.

BACKGROUND

Conventional medical and surgical procedures routinely involve the use of surgical tools and instruments which allow surgeons to approach and manipulate surgical sites. By way of non-limiting example, rotary instruments such as handheld drills are commonly utilized in connection with orthopedic procedures to address various musculoskeletal conditions, such as trauma, sports injuries, degenerative diseases, joint reconstruction, and the like. In procedures where handheld drills or similar surgical instruments are employed, rotational torque selectively generated by an actuator (e.g., an electric motor) is used to rotate a releasably-attachable drill bit at different speeds. Drill bits utilized in connection with medical and surgical procedures are typically realized as single-use components that are replaced between procedures.

While handheld surgical instruments and drill bits are routinely utilized to assist in the performance of a variety of different types of medical and/or surgical procedures, there is a need in the art to continuously improve such drill bits and handheld surgical instruments.

SUMMARY

The present disclosure provides a drill bit comprising a shank extending along an axis between a proximal end and a distal end. The drill bit may further comprise a cutting tip portion adjacent to the distal end of the shank. The drill bit may further comprise an interface arranged between the proximal end and the distal end. The interface may comprise at least two outermost drive portions spaced from one another to define a maximum drive dimension of the interface with the two outermost drive portions each separately spaced at a first interface distance from the axis. The drill bit may further comprise a resilient arm extending from the proximal end of the shank to an arm end. The resilient arm may comprise an outer arm surface facing away from the axis, and a retention surface facing toward the distal end of the shank and radially aligned about the axis with one of the outermost drive portions. The resilient arm may be movable relative to the axis between: a first position where the outer arm surface is spaced from the axis at a first arm distance greater than the first interface distance, and a second position where the outer arm surface is spaced from the axis at a second arm distance less than the first arm distance and less than or equal to the first interface distance.

The present disclosure also provides a drill bit comprising a shank extending along an axis between a proximal end and a distal end. The drill bit may further comprise a cutting tip portion adjacent to the distal end of the shank. The drill bit may further comprise an interface arranged between the proximal end and the distal end. The interface may comprise at least two outermost drive portions spaced from one another to define a maximum drive dimension of the interface with the two outermost drive portions each separately spaced at a first interface distance from the axis. The drill bit may further comprise a resilient arm extending from the proximal end of the shank to an arm end. The resilient arm may comprise an outer arm surface facing away from the axis, and a retention surface facing toward the distal end of the shank. The resilient arm may be movable relative to the axis between: a first position where the outer arm surface is spaced from the axis at a first arm distance greater than the first interface distance, and a second position where the outer arm surface is spaced from the axis at a second arm distance less than the first arm distance and less than or equal to the first interface distance. The retention surface may further comprise a first bisecting plane that intersects the axis to define two equal portions of the retention surface. One of the outermost drive portions comprises a second bisecting plane that intersects the axis to define two equal portions of the outermost drive portion. The second bisecting plane is radially spaced approximately 60 degrees from the first bisecting plane about the axis.

The present disclosure also provides a drill bit comprising a shank extending along an axis between a proximal end and a distal end. The drill bit may further comprise a cutting tip portion adjacent to the distal end of the shank. The drill bit may further comprise an interface arranged between the proximal end and the distal end. The interface may comprise at least two outermost drive portions spaced from one another to define a maximum drive dimension of the interface with the two outermost drive portions each separately spaced at a first interface distance from the axis. The interface may further comprise at least two outer non-drive portions spaced diametrically from one another relative to the axis to define a minimum interface dimension. The two outer non-drive portions being radially spaced from the two outermost drive portions about the axis. The drill bit may further comprise a resilient arm extending from the proximal end of the shank to an arm end. The resilient arm may comprise an outer arm surface facing away from the axis, and a retention surface facing toward the distal end of the shank and radially aligned about the axis with one of the outermost drive portions. The resilient arm may be movable relative to the axis between: a first position where the outer arm surface is spaced from the axis at a first arm distance greater than the first interface distance, and a second position where the outer arm surface is spaced from the axis at a second arm distance less than the first arm distance and less than or equal to the first interface distance.

The present disclosure provides a drill bit comprising a shank extending along an axis between a proximal end and a distal end. The drill bit may further comprise a cutting tip portion adjacent to the distal end of the shank. The drill bit may further comprise an interface arranged between the proximal end and the distal end, and the interface may comprise at least one outermost drive portion spaced at a first interface distance from the axis. The drill bit may further comprise a resilient arm extending from the proximal end of the shank to an arm end. The resilient arm may comprise an outer arm surface facing away from the axis and a retention surface facing toward the distal end of the shank.

The retention surface may be radially aligned about the axis with respect to the outermost drive portion at an angle of approximately 0-degrees, 60-degrees, 120-degrees, or 180-degrees. The resilient arm may be movable relative to the axis between: a first position where the outer arm surface is spaced from the axis at a first arm distance greater than the first interface distance, and a second position where the outer arm surface is spaced from the axis at a second arm distance less than the first arm distance and less than or equal to the first interface distance.

Other features and advantages of the present disclosure will be readily appreciated, as the same becomes better understood, after reading the subsequent description taken in conjunction with the accompanying drawings.

BRIEF DESCRIPTION OF THE DRAWINGS

FIG. 22 is a left-side view of the portions of the drill bit illustrated in FIGS. 20-21.

FIG. 23 is a top-side view of the portions of the drill bit illustrated in FIGS. 20-22.

DETAILED DESCRIPTION

Figure 1:
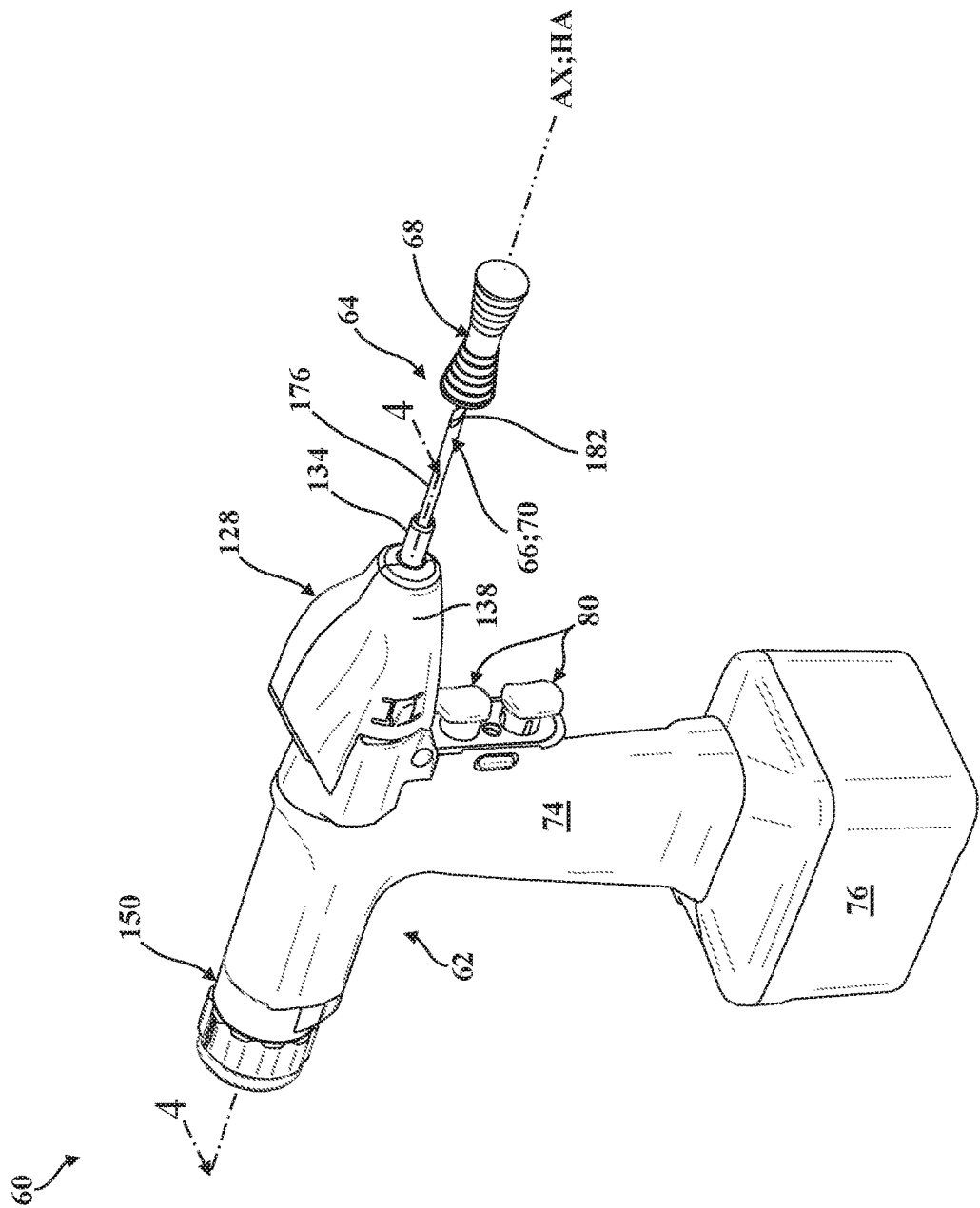
FIG. 1 is perspective view of a surgical system comprising a surgical instrument and end effector assembly, the end effector assembly shown having a drill bit and a tip protector according to one configuration.
Figure 2:
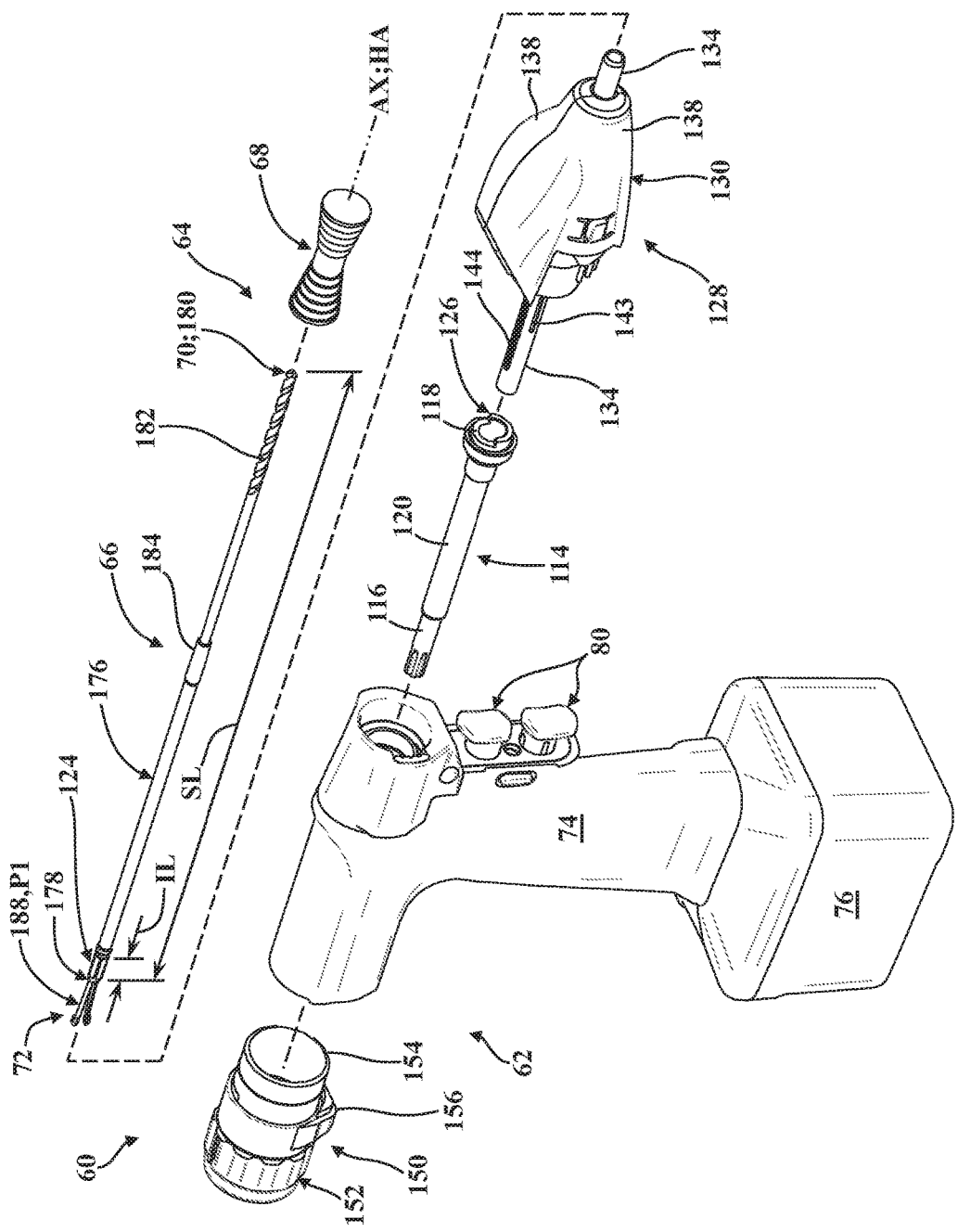
FIG. 2 is a partially-exploded perspective view of the surgical system of FIG. 1, with the surgical instrument shown having a measurement module, a drive assembly, and a release mechanism spaced from a handpiece body, and with the end effector assembly removed from the surgical instrument and shown with the tip protector spaced from a distal cutting tip portion of the drill bit.

With reference to the drawings, where like numerals are used to designate like structure throughout the several views, a surgical system is shown at 60 in FIGS. 1-2 for performing an operational function associated with medical and/or surgical procedures. In the representative configuration illustrated herein, the surgical system 60 is employed to facilitate penetrating tissue of a patient, such as bone. To this end, the illustrated configuration of the surgical system 60 comprises a handheld surgical instrument 62 and an end effector assembly, generally indicated at 64. The end effector assembly 64, in turn, comprises a drill bit 66 and a tip protector 68. As is best depicted in FIG. 2, the drill bit 66 extends generally longitudinally along an axis AX between a cutting tip portion, generally indicated at 70, and an insertion portion, generally indicated at 72. As is described in greater detail below, the cutting tip portion 70 is configured to engage tissue, and the insertion portion 72 is configured to facilitate releasable attachment of the drill bit 66 to the surgical instrument 62.

In order to help facilitate attachment of the drill bit 66 to the surgical instrument 62, in some configurations, the tip protector 68 is configured to releasably secure to the cutting tip portion 70 of the drill bit 66 while concealing at least a portion of the cutting tip portion 70 of the drill bit 66, thereby allowing a user (e.g., a surgeon) of the surgical system 60 to handle and position the drill bit 66 safely during attachment to the surgical instrument 62. Once the end effector assembly 64 has been attached to the surgical instrument 62, the tip protector 68 is subsequently removed from the cutting tip portion 70 of the drill bit 66, and the surgical system 60 can then be utilized to penetrate tissue. Configurations of the tip protector 68 are described in greater detail below in connection with FIGS. 34-46.

Referring now to FIGS. 1-19C, in the representative configuration illustrated herein, the surgical instrument 62 is realized as a handheld drill with a pistol-grip shaped handpiece body 74 which releasably attaches to a battery 76 (battery attachment not shown in detail). However, it is contemplated that the handpiece body can have any suitable shape with or without a pistol grip. While the illustrated surgical instrument 62 employs a battery 76 which is releasably attachable to the handpiece body 74 to provide power to the surgical instrument 62 utilized to rotate the drill bit 66, it will be appreciated that the surgical instrument 62 may be configured in other ways, such as with an internal (e.g., non-removable) battery, or with a tethered connection to an external console, power supply, and the like. Other configurations are contemplated.

Figure 3:
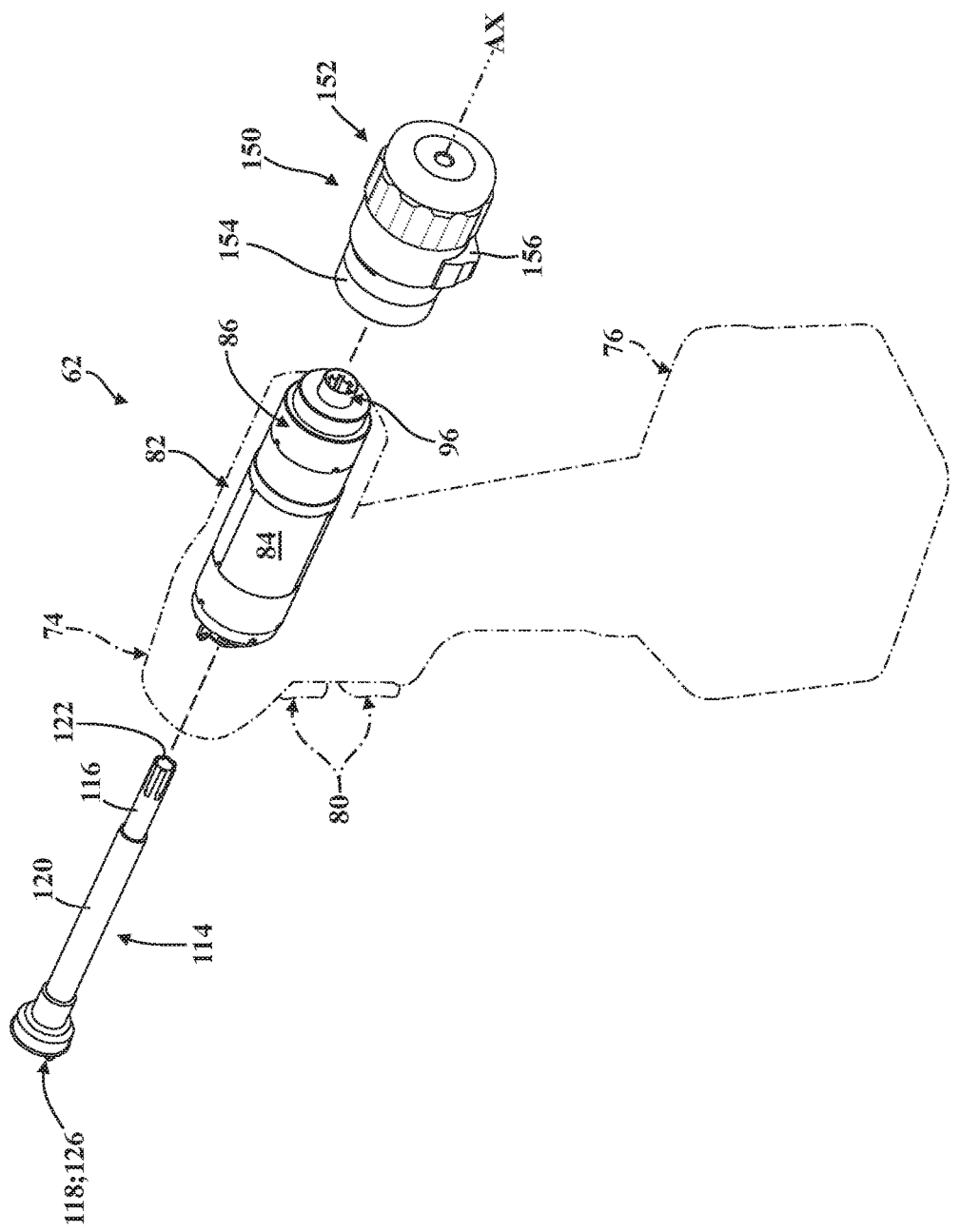
FIG. 3 is a partially-exploded perspective view of portions of the surgical instrument of FIGS. 1-2, shown with the drive assembly and the release mechanism spaced from a phantom outline of the handpiece body to depict an actuator assembly.

In the illustrated configuration, the battery 76 or other power source provides power to a controller 78 (depicted schematically in FIG. 6) which, in turn, is disposed in communication with an input control 80 and an actuator assembly 82 (see also FIG. 3). The input control 80 and the actuator assembly 82 are each supported by the handpiece body 74. The controller 78 is generally configured to facilitate operation of the actuator assembly 82 in response to actuation of the input control 80. The input control 80 has a trigger-style configuration in the illustrated configuration, is responsive to actuation by a user (e.g., a surgeon), and communicates with the controller 78, such as via electrical signals produced by magnets and Hall effect sensors. Thus, when the surgeon actuates the input control 80 to operate the surgical instrument 62, the controller 78 directs power from the battery 76 to the actuator assembly 82 which, in turn, generates rotational torque employed to rotate the drill bit 66, as described in greater detail below. Those having ordinary skill in the art will appreciate that the handpiece body 74, the battery 76, the controller 78, and the input control 80 could each be configured in a number of different ways to facilitate generating rotational torque without departing from the scope of the present disclosure.

Figure 6:
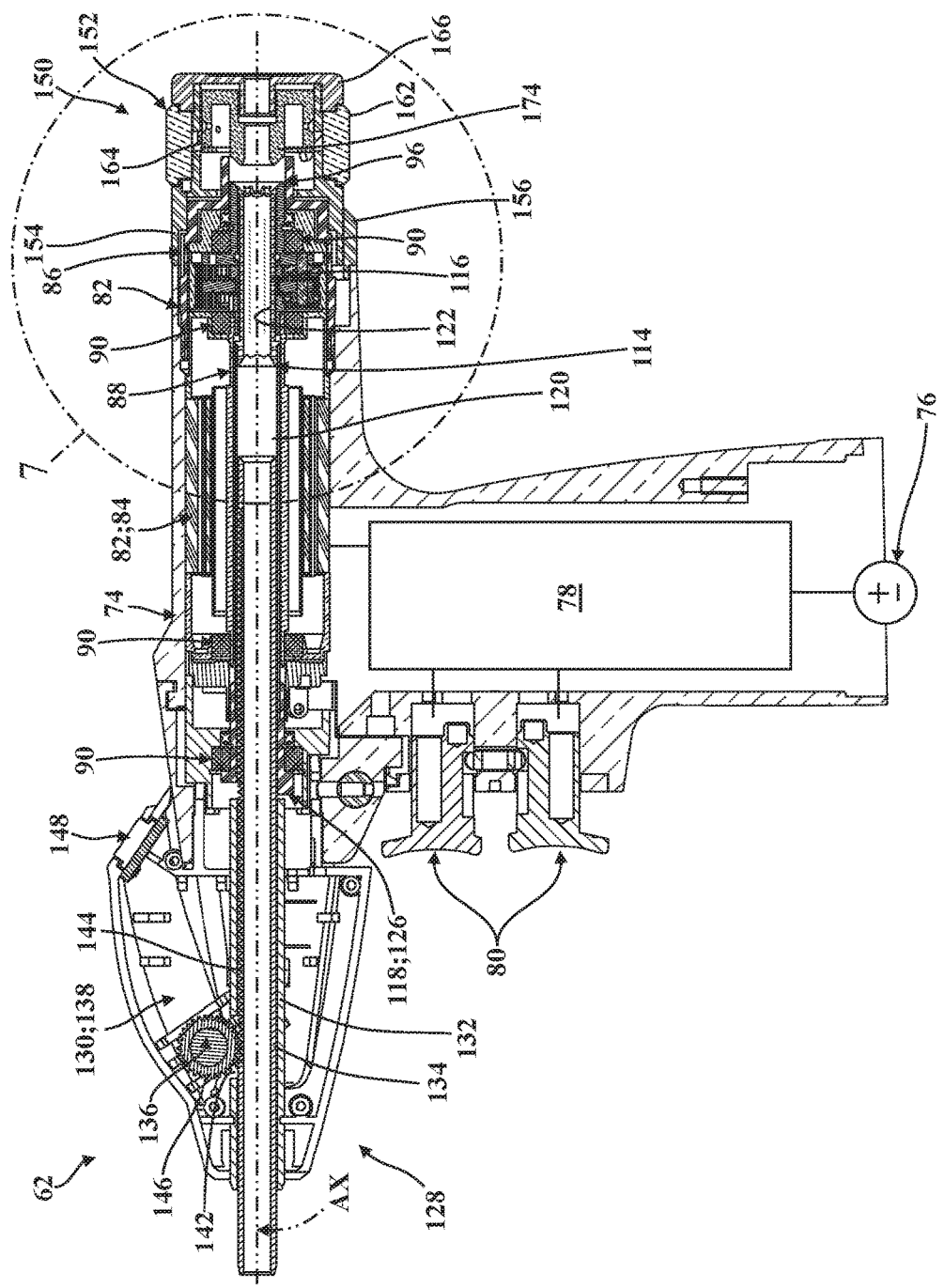
FIG. 6 is a sectional view taken longitudinally through the surgical instrument of FIGS. 1-5, with the end effector assembly removed from the surgical instrument.
Figure 9:
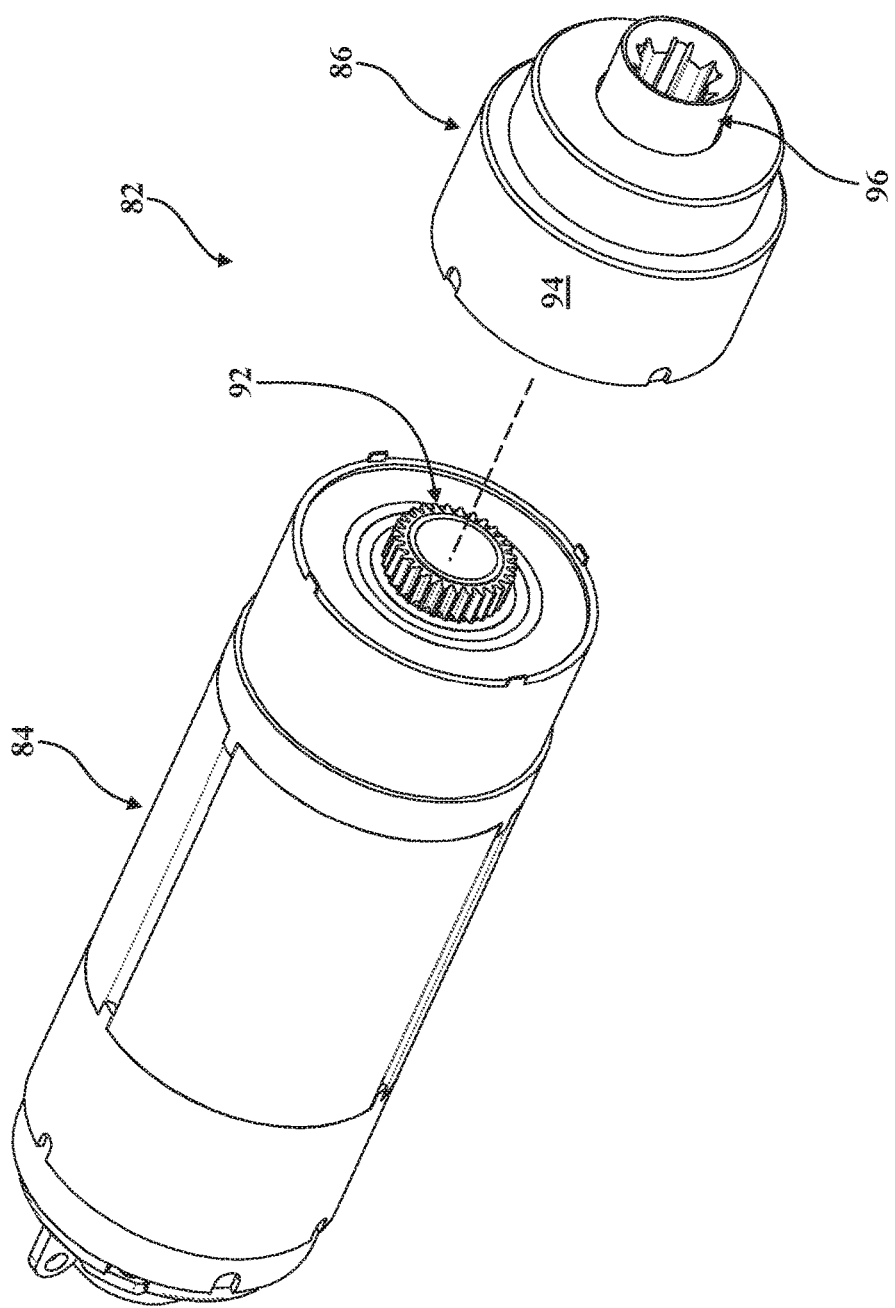
FIG. 9 is a partially-exploded view of the actuator assembly of FIGS. 3-7I, shown having a motor with a drive gear, and a gearset with an output hub.
Figure 10:
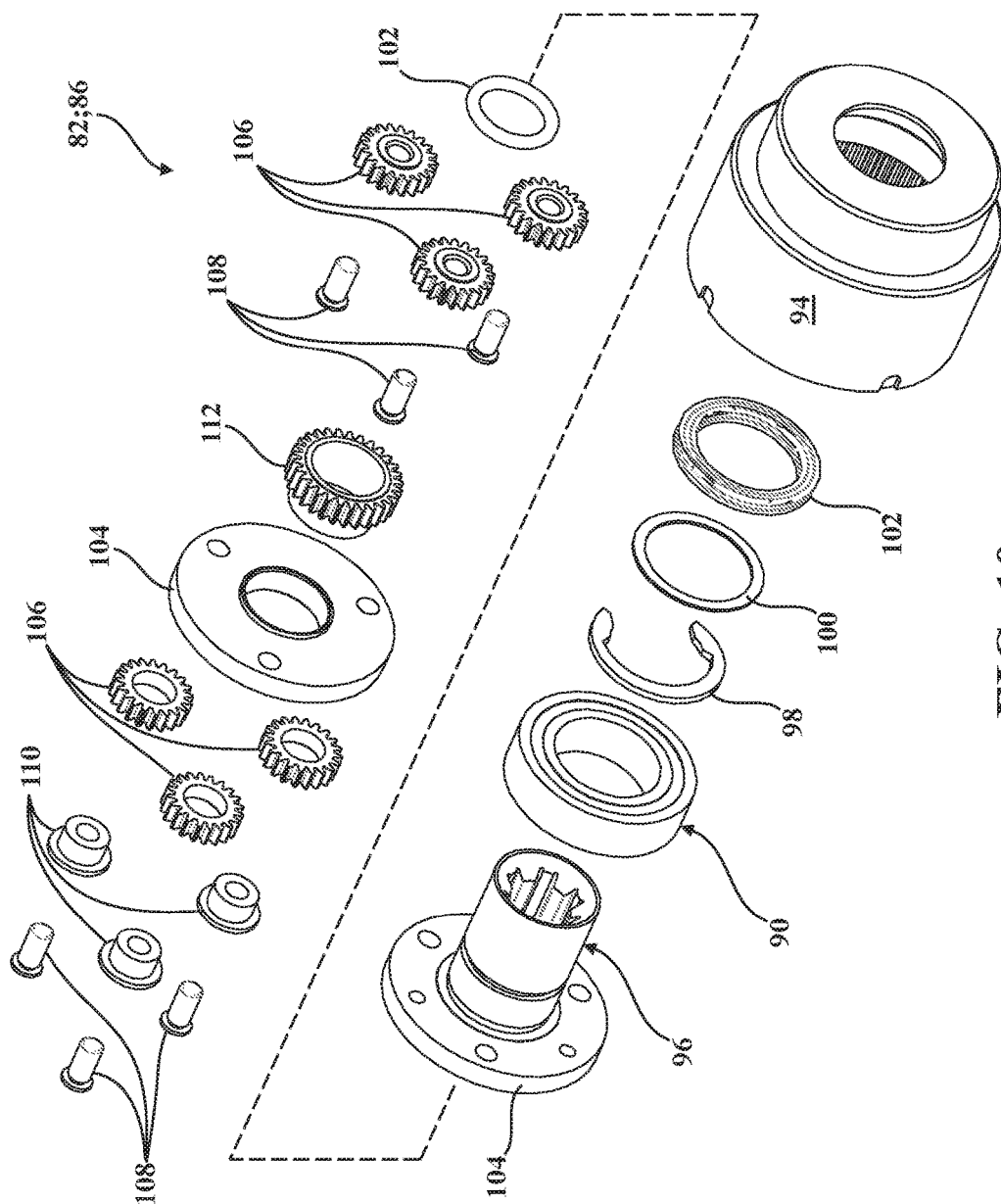
FIG. 10 is an exploded perspective view of the gearset of FIG. 9.
Figure 11:
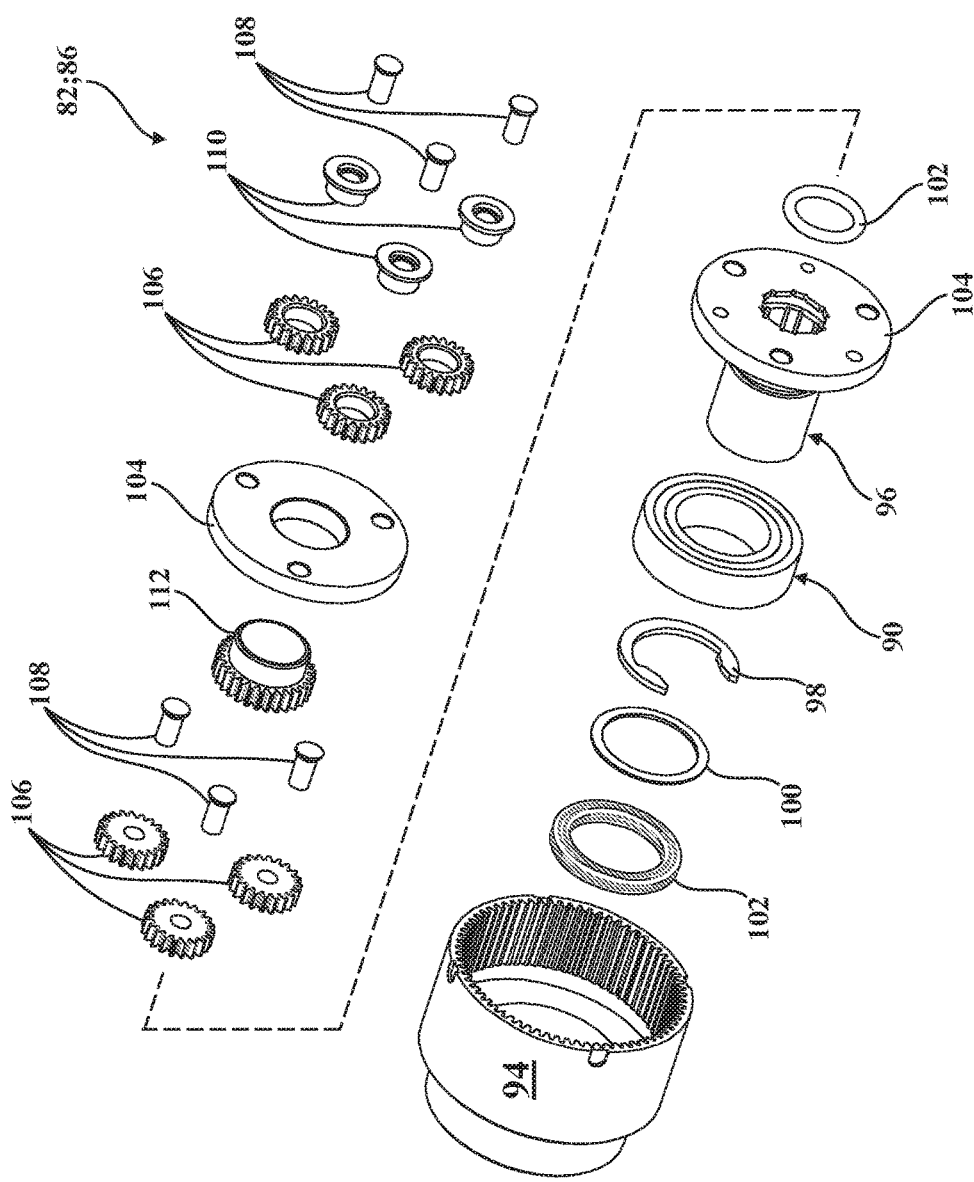
FIG. 11 is another exploded perspective view of the gearset of FIGS. 9-10.

As is best shown in FIG. 9, the actuator assembly 82 generally comprises an electric motor 84 and a gearset 86 which are each supported within the handpiece body 74. The motor 84 is configured to selectively generate rotational torque in response to commands, signals, and the like received from the controller 78. As is best shown in FIG. 6, the motor 84 comprises a rotor cannula 88 supported for rotation about the axis AX by a pair of bearings 90. A drive gear 92 arranged adjacent to the gearset 86 (see FIG. 9) is coupled to and rotates concurrently with the rotor cannula 88, and is employed to transmit rotational torque to the gearset 86. To this end, in the illustrated configuration, and as is shown in FIGS. 10-11, the gearset 86 is realized as two-stage compound planetary arrangement and generally comprises a ring gear housing 94 which, among other things, rotationally supports an output hub 96 via a bearing 90, as well as one or more retaining clips 98, washers 100, and/or seals 102. However, other configurations of the gearset 86 are contemplated.

With continued reference to FIGS. 10-11, in the illustrated configuration, the output hub 96 of the gearset 86 comprises an integrated carrier 104 to which three planet gears 106 are supported via an arrangement of shafts 108 and, in some configurations, bushings 110 interposed between the shafts 108 and the planet gears 106. The planet gears 106 are disposed in meshed engagement with the ring gear housing 94 and also with a sun gear 112. The sun gear 112 rotates concurrently with a second carrier 104 which, in turn, supports an additional three planet gears 106 via respective shafts 108 and bushings 110. These additional planet gears 106 are likewise disposed in meshed engagement with the ring gear housing 94, and are disposed in meshed engagement with the drive gear 92 of the motor 84. Thus, rotation of the drive gear 92 via actuation of the motor 84 effects concurrent rotation of the output hub 96. As is described in greater detail below in connection with FIGS. 15A-15C and 17A-19C, the output hub 96 rotates concurrently with the drill bit 66. Those having ordinary skill in the art will appreciate that the actuator assembly 82 could be configured in other ways without departing from the scope of the present disclosure. By way of non-limiting example, while the illustrated actuator assembly 82 employs a compound planetary arrangement to adjust rotational speed and torque between the drive gear 92 of the motor 84 and the output hub 96, other types of gearsets 86 could be utilized in some configurations. Moreover, while the illustrated actuator assembly 82 employs an electrically-powered brushless DC motor to generate rotational torque, other types of prime movers could be utilized. Other configurations are contemplated.

Figure 8:
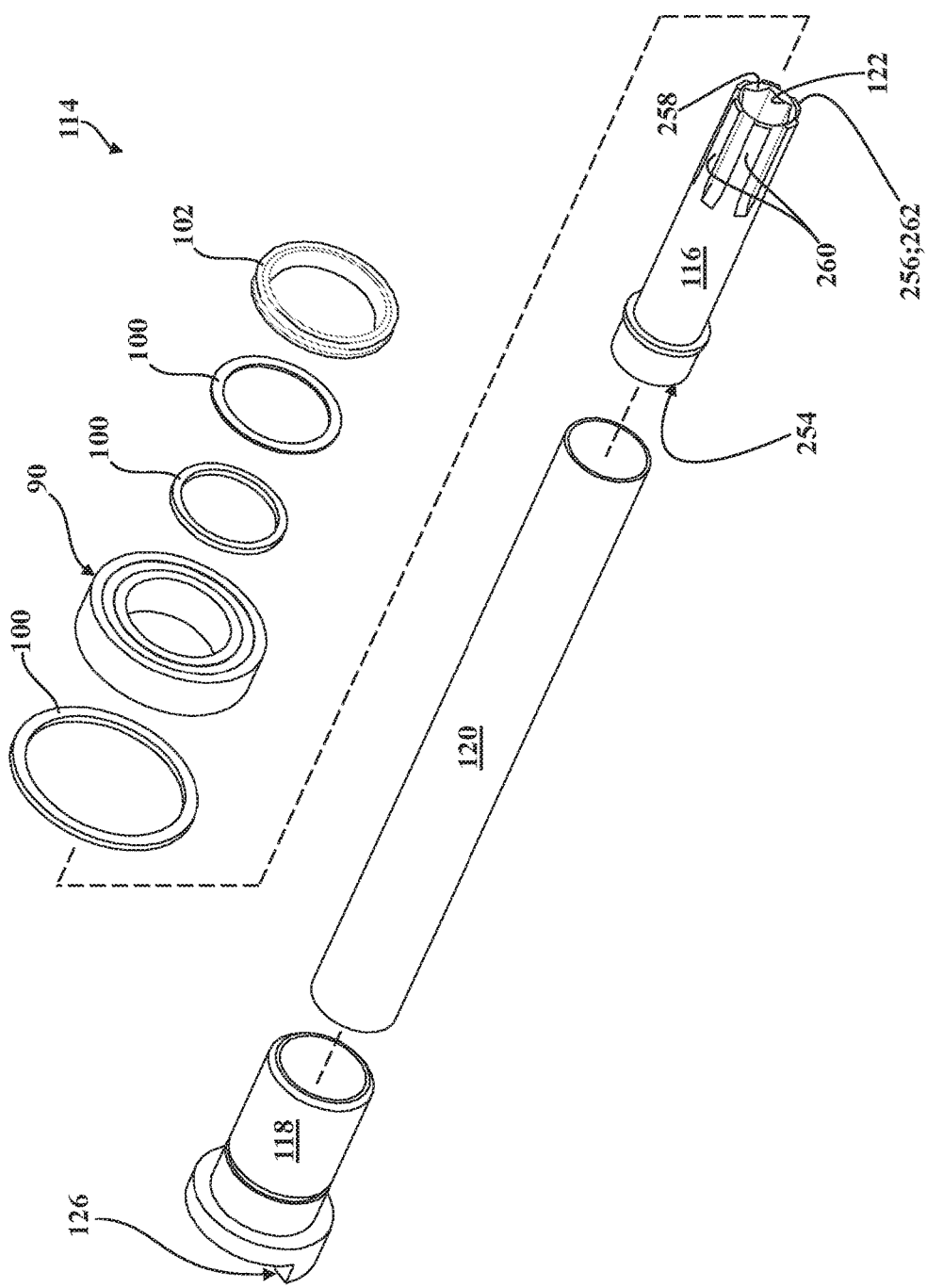
FIG. 8 is an exploded perspective view of the drive assembly of FIGS. 2-7I.

As noted above, rotational torque generated by the motor 84 effects rotation of the output hub 96 which, in turn, rotates concurrently with the drill bit 66. To this end, and as is best shown in FIGS. 2-5 and 8, the surgical instrument 62 further comprises a drive assembly 114 which generally extends through the various cannulated components of the actuator assembly 82 into splined engagement with the output hub 96 of the gearset 86. As is described in greater detail below, the drive assembly 114 is configured to facilitate releasable attachment between the drill bit 66 and the surgical instrument 62. The drive assembly 114 generally comprises a driving cannula 116, a driving head 118, and a driving body 120 which extends between, and rotates concurrently with, the driving cannula 116 and the driving head 118. The drive assembly 114 is supported for rotation about the axis AX within the handpiece body 74 via splined engagement with the output hub 96 adjacent the driving cannula 116, and via an arrangement of bearings 90, snap rings 100, and seals 102 adjacent the driving head 118 (see FIGS. 6 and 8). As is described in greater detail below in connection with FIGS. 15A-33, the driving cannula 116 of the drive assembly 114 comprises a generally hexagonal bore 122 which is employed to receive an interface 124 of the drill bit 66 (see FIG. 2) so as to facilitate concurrent rotation between the drill bit 66 and the drive assembly 114. As will be appreciated from the subsequent description below, the interface 124 is defined by physical structure extending outwardly from the axis AX such that the interface 124 is configured to be driven externally. As is best shown in FIG. 8, the driving body 120 and the driving head 118 each have cylindrical bores. However, other configurations of the driving body and the driving head can have non-cylindrical bores, such as polygonal or oval bore profiles.

In the illustrated configuration, the driving head 118 of the drive assembly 114 comprises a coupling, generally indicated at 126, which is provided to facilitate transmitting rotational torque when the surgical instrument 62 is utilized in connection with other applications besides rotating the drill bit 66 of the present disclosure. More specifically, the illustrated drive assembly 114 is configured such that the surgical instrument 62 can rotate, drive, or otherwise actuate a number of different types of surgical instruments, tools, modules, end effectors, and the like, which can be configured to engage and rotate concurrently with either the bore 122 of the driving cannula 116, or the coupling 126 of the driving head 118. It will be appreciated that this configuration allows the same surgical instrument 62 to be utilized in a broad number of medical and/or surgical procedures. However, it is contemplated that the drive assembly 114 could be configured differently in some configurations, such as to omit a driving head 118 with a coupling 126 in configurations where the surgical instrument 62 configured for dedicated use with the drill bit 66 of the present disclosure.

Figure 4:
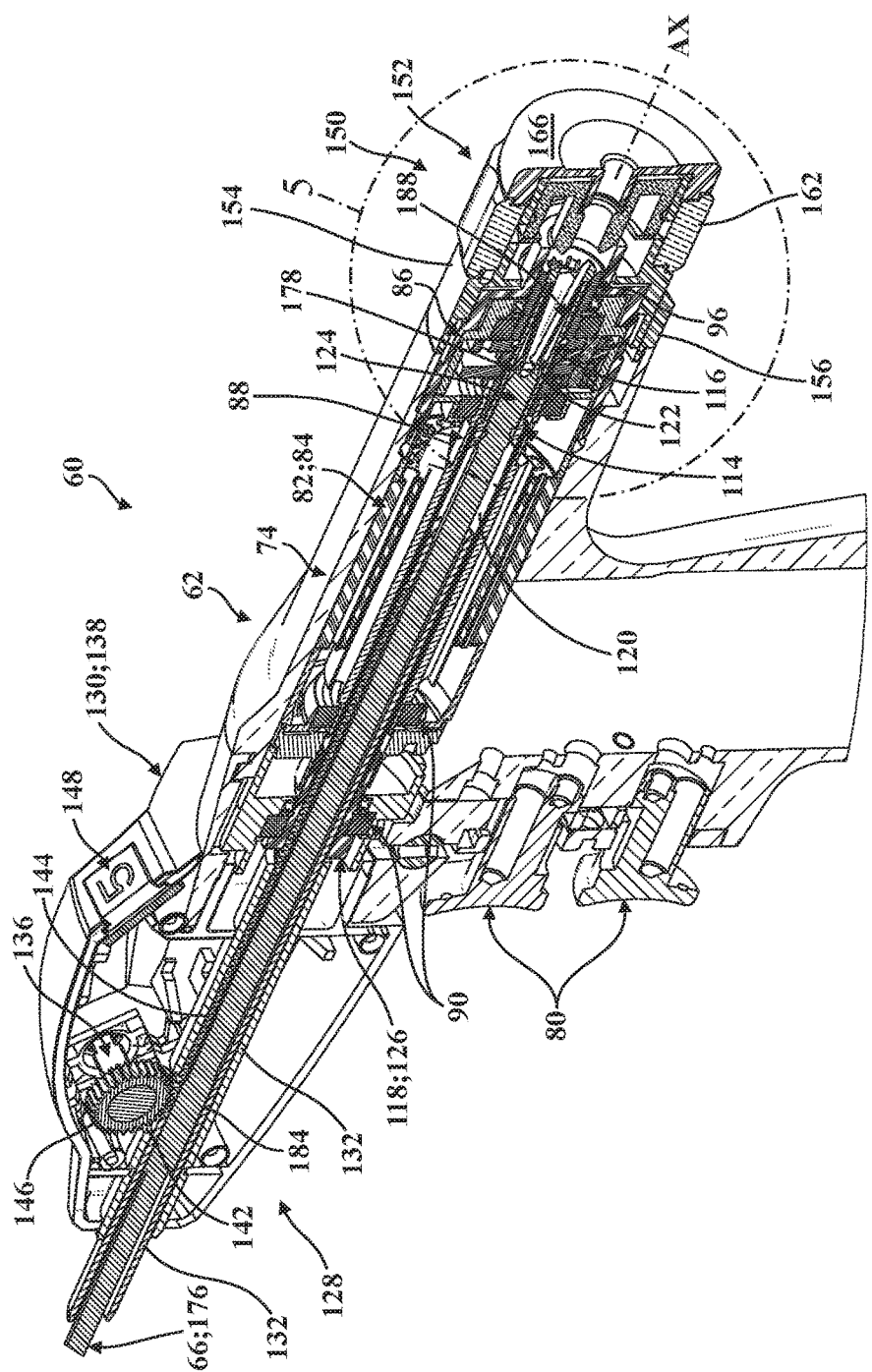
FIG. 4 is a partial isometric sectional view taken along line 4-4 in FIG. 1.
Figure 5:
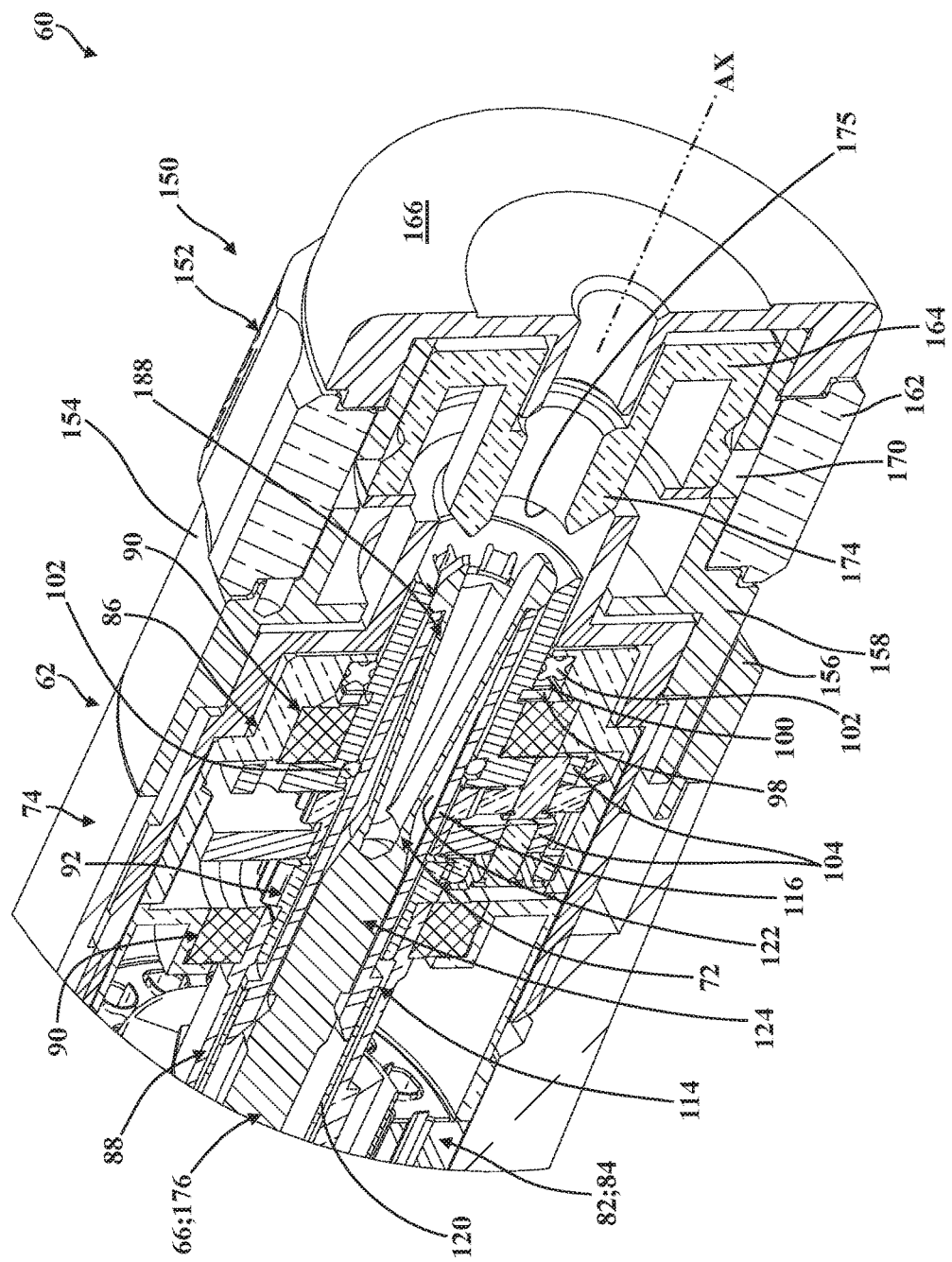
FIG. 5 is an enlarged detail view taken at indicia 5 in FIG. 4.

Referring now to FIGS. 1-2, 4, and 6, the illustrated configuration of the surgical system 60 further comprises a measurement module, generally indicated at 128, which is configured to releasably attach to the surgical instrument 62 to provide the surgeon with measurement functionality during use. To this end, and as is best shown in FIGS. 4 and 6, the measurement module 128 generally comprises a housing 130, a guide bushing 132, a measurement cannula 134, and a sensor assembly 136. The housing 130 is releasably attachable to the surgical instrument 62 and generally supports the various components of the measurement module 128. The illustrated housing 130 is formed as a pair of housing components 138 which interlock or otherwise attach together, and may be configured for disassembly to facilitate cleaning or servicing the measurement module 128. In the illustrated configuration, the housing components 138 and the guide bushing 132 comprise correspondingly-shaped features arranged to prevent relative axial and rotational movement therebetween, such as via notches formed in the guide bushing 132 which fit into webs or ribs formed in the housing components 138 (not shown in detail). The guide bushing 132 further comprises a window 142 for use with the sensor assembly 136 as described in detail below.

The measurement cannula 134 is disposed within the guide bushing 132 and is supported for translational movement along the axis AX. An elongated recessed slot 143 (partially depicted in FIG. 2) is formed transversely into the measurement cannula 134 and extends longitudinally. While not specifically illustrated herein, the elongated recessed slot 143 is shaped and arranged to receive a travel stop element which, in turn, is supported by the housing 130 and likewise extends through an aperture formed transversely through the side of the guide bushing 132; this arrangement serves both to limit how far the measurement cannula 134 can be axially extended or retracted relative to the guide bushing 132, and also prevents the measurement cannula 134 from rotating about the axis AX. However, it will be appreciated that the measurement module 128 could be configured to limit or prevent movement of the measurement cannula 134 in other ways without departing from the scope of the present disclosure.

The measurement cannula 134 further comprises rack teeth 144 which are disposed in meshed engagement with a sensor gear 146 of the sensor assembly 136. As shown in FIG. 6, the window 142 of the guide bushing 132 is arranged adjacent to the sensor assembly 136 to facilitate the meshed engagement between the rack teeth 144 and the sensor gear 146. The sensor assembly 136 is responsive to rotation of the sensor gear 146 resulting from axial movement of the measurement cannula 134, and may be realized with a potentiometer, a rotary encoder, and the like, in order to generate electrical signals representing changes in the position of the measurement cannula 134 along the axis AX. Thus, it will be appreciated that the sensor assembly 136 is able to provide the surgical instrument 62 with enhanced functionality. By way of example, in some configurations, the sensor assembly 136 may be disposed in communication with the controller 78, which may be configured to interrupt or adjust how the motor 84 is driven based on movement of the measurement cannula 134, such as to slow rotation of the drill bit 66 at a specific drilling depth into tissue. The sensor assembly 136 may also be disposed in communication with an output device 148, such as a display screen, one or more light-emitting diodes (LEDs), and the like, to provide the surgeon with information relating to movement of the measurement cannula 134, such as to display a real-time drilling depth, a recorded historical maximum drilling depth, and the like. Other configurations are contemplated. The disclosure of International Patent Application No. PCT US2016049899, entitled "Powered Surgical Drill With Integral Depth Gauge That Includes A Probe That Slides Over A Drill Bit" and filed on Sep. 1, 2016, is hereby incorporated by reference in its entirety.

Those having ordinary skill in the art will appreciate that the various components of the measurement module 128 could be arranged in a number of different ways. Moreover, while the illustrated measurement module 128 attaches to the illustrated surgical instrument 62 and is compatible with the drill bit 66 of the present disclosure, it is contemplated that the surgical instrument 62 could omit the measurement module 128 in some configurations, such as to employ different types of modules, housings, covers, and the like.

Figure 12:
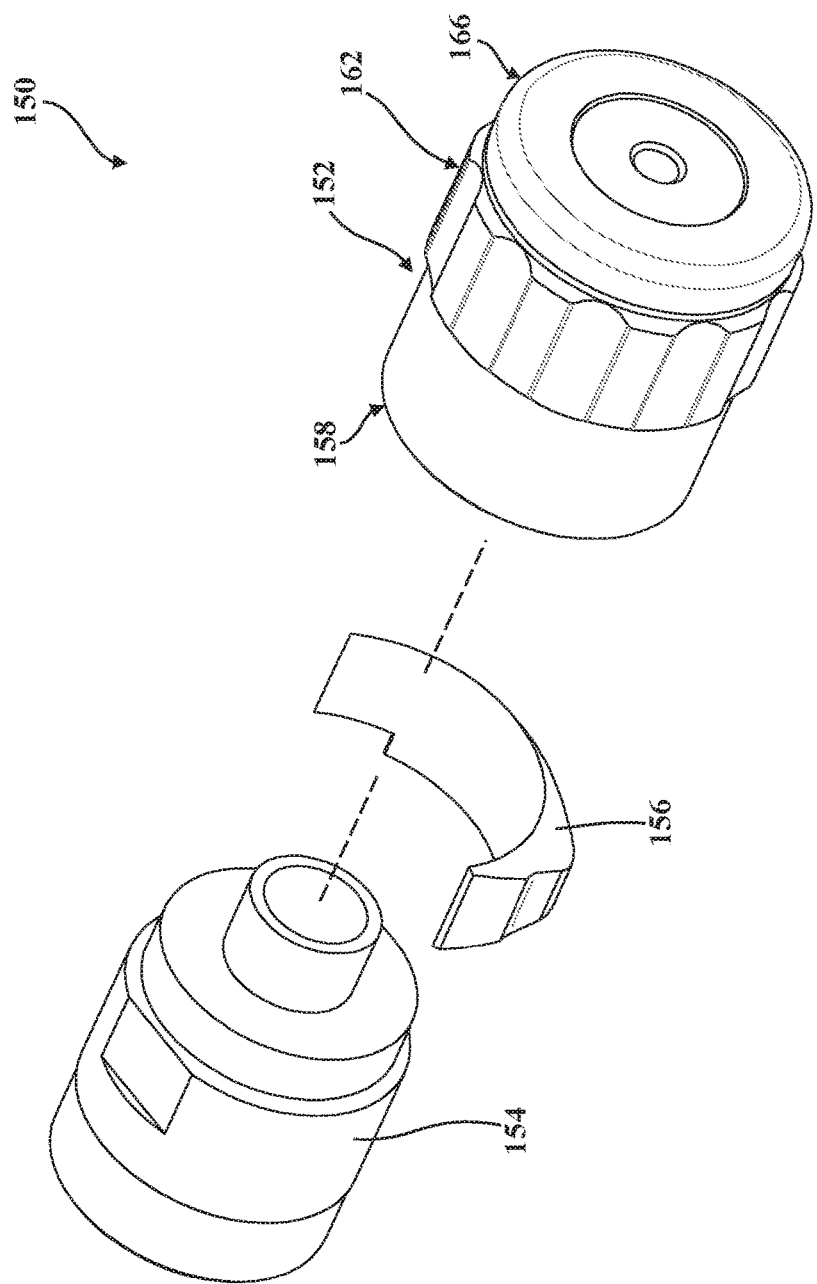
FIG. 12 is a partially-exploded view of the release mechanism of FIGS. 1-7I, shown having a release subassembly spaced from a keeper body and a housing adapter.
Figure 13:
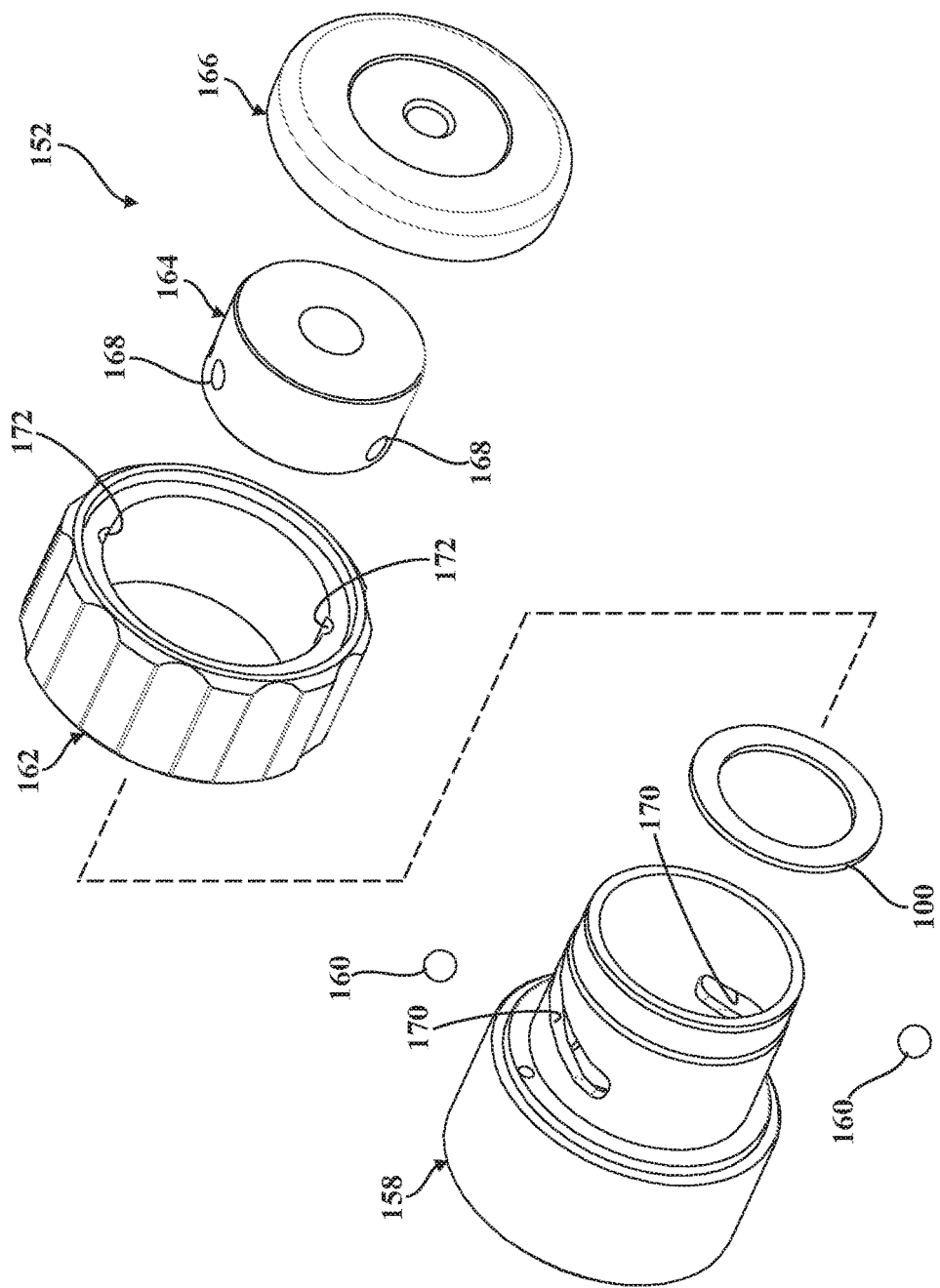
FIG. 13 is an exploded perspective view of the release subassembly of FIG. 12.
Figure 14:
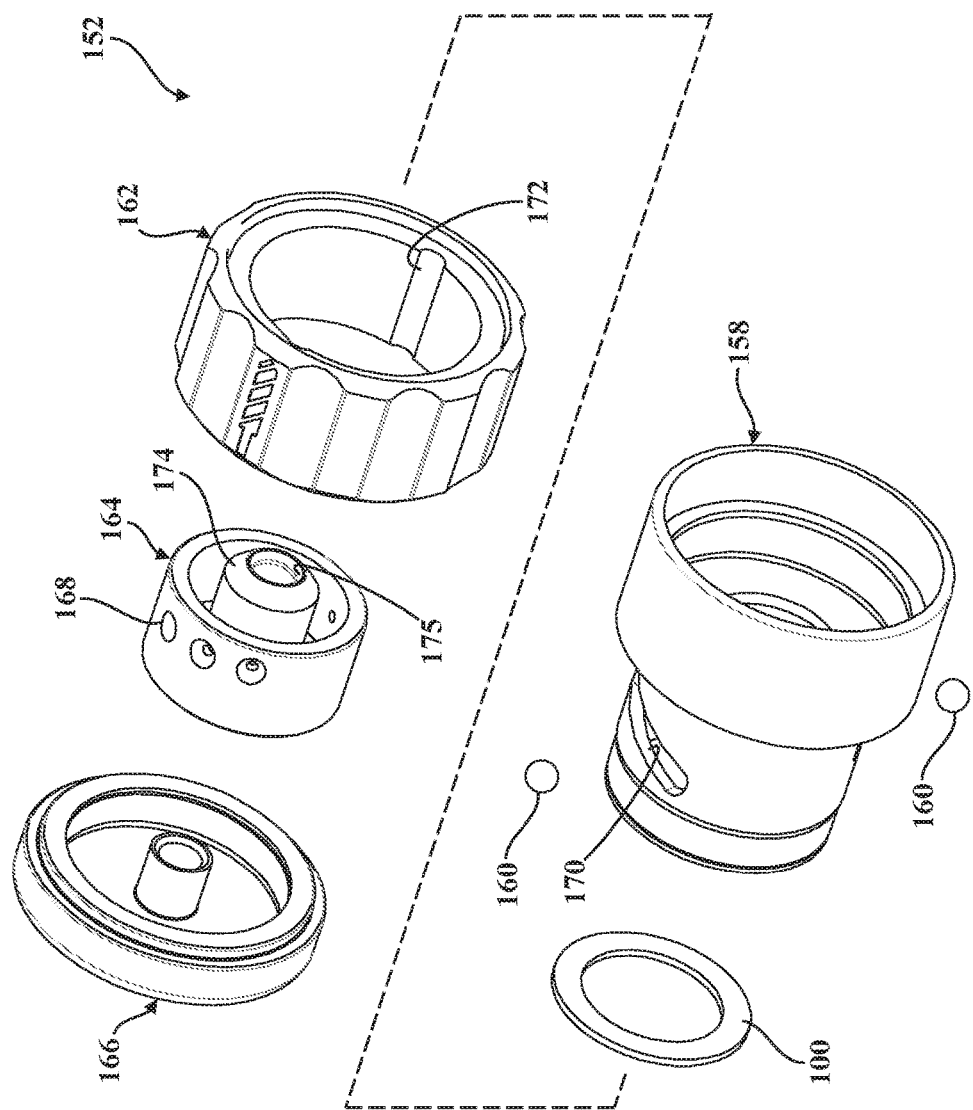
FIG. 14 is another exploded perspective view of the release subassembly of FIGS. 12-13.

Referring now to FIGS. 1-3 and 12-14, the illustrated configuration of the surgical instrument 62 further comprises a release mechanism, generally indicated at 150, configured to facilitate removal of the drill bit 66 as described in greater detail below in connection with FIGS. 7F-7I. As shown in FIG. 12, the release mechanism 150 generally comprises a release subassembly 152, a keeper body 154, and a housing adapter 156. The keeper body 154 and the housing adapter 156 are respectively configured to secure the release subassembly 152 to the actuator assembly 82 and the handpiece body 74, and could be realized with a number of different configurations or could be integrated into other parts of the surgical instrument 62 in some configurations. As shown in FIGS. 13-14, the release subassembly 152 of the release mechanism 150 comprises a release body 158, a washer 100, a pair of spherical guides 160, a collar 162, a slide element 164, and a cap 166. The spherical guides 160 are supported within pockets 168 formed in the slide element 164, ride along respective helical slots 170 formed in the release body 158, and move along respective collar channels 172 formed in the collar 162. This arrangement allows the slide element 164 to translate distally and proximally along the axis AX in response to rotation of the collar 162 (see FIGS. 7F-7I). As is described in greater detail below, the slide element 164 comprises an actuating element 174 which defines a tapered inner surface 175 and which is configured to engage the insertion portion 72 of the drill bit 66, in response to rotation of the collar 162 which causes the slide element 164 to translate distally along the axis AX, to facilitate removing the drill bit 66 from the drive assembly 114 of the surgical instrument 62. A biasing element such as a compression spring (not shown) may be interposed between the release body 158 and the slide element 164, along with one or more washers 100, to urge the slide element 164 toward the cap 166. Other suitable biasing elements and/or fasteners could be employed to facilitate urging the slide element toward the cap and/or axially retaining the slide element relative to the release subassembly.

As noted above, the drill bit 66 of the present disclosure generally extends along the axis AX between the cutting tip portion 70 and the insertion portion 72, and is configured for releasable attachment to the surgical instrument 62 described herein and illustrated throughout the drawings via engagement between the interface 124 of the drill bit 66 and the bore 122 of the driving cannula 116 of the drive assembly 114. The driving cannula 116, in turn, cooperates with the output hub 96 of the gearset 86 of the actuator assembly 82 to facilitate rotating the drill bit 66 about the axis AX. The drill bit 66, the driving cannula 116, and the output hub 96, as well as the cooperation therebetween, will each be described in greater detail below.

Referring now to FIGS. 2 and 20-24B, the drill bit 66 comprises a shank, generally indicated at 176, which extends along the axis AX between a proximal end 178 and a distal end 180 (shown in FIG. 2). The distal end 180 of the shank 176 is provided with flutes 182 which are helically disposed about the axis AX and extend to the tip of the drill bit 66 to promote tissue penetration (see FIG. 2). In the illustrated configuration, the drill bit 66 is also provided with a bearing region 184 coupled to the shank 176 between the proximal end 178 and the distal end 180 (see FIG. 2). The bearing region 184 is sized so as to be received within and rotate relative to the measurement cannula 134 of the measurement module 128 (see FIG. 4). Here, the bearing region 184 essentially defines a "stepped" outer region of the shank 176 that affords rotational support along the length of the drill bit 66, and has a larger diameter than adjacent distal and proximal regions of the shank 176 in the illustrated configuration. However, it will be appreciated that the bearing region 184 of the shank 176 of the drill bit 66 could configured in other ways without departing from the scope of the present disclosure. Furthermore, while described as a drill bit 66 in the present disclosure, it is also contemplated that the drill bit 66 could have similar features and be configured as another suitable end effector, or rotary end-effector, such as a bur or reamer.

In the illustrated configuration, the drill bit 66 is formed as a single-piece component such that the distal end 180 of the shank 176 corresponds to or is otherwise disposed adjacent the cutting tip portion 70 of the drill bit 66. However, it will be appreciated that the drill bit 66 could be manufactured in other ways, such as where the cutting tip portion 70 of the drill bit 66 is formed as a separate component from the shank 176 which is subsequently attached to the distal end 180 of the shank 176. Nevertheless, for the purposes of clarity and consistency, the cutting tip portion 70 introduced above corresponds with the distal end 180 of the shank 176 in the illustrated configuration described herein.

FIGS. 20-23 generally depict the insertion portion 72 of the drill bit 66 which, as noted above, is configured to facilitate releasable attachment to the surgical instrument 62. To this end, the interface 124 of the drill bit 66 is coupled to the shank 176 adjacent to but spaced distally from the proximal end 178 of the shank 176. As is described in greater detail below, the interface 124 of the shank 176 is configured to facilitate rotationally locking the drill bit 66 to the surgical instrument 62 so that the surgical instrument 62 can rotate the drill bit 66 upon attachment. In order to axially lock the drill bit 66 to the surgical instrument 62, the drill bit 66 further comprises a stop 186 and one or more resilient arms, generally indicated at 188. The stop 186 is coupled to the shank 176 adjacent to and spaced distally from the interface 124, and defines a stop surface 190 which has a tapered, generally frustoconical profile. As shown in FIGS. 7F and 17C, the stop surface 190 is shaped and arranged to abut a correspondingly-shaped, tapered seat surface 192 of the driving cannula 116 of the drive assembly 114 to limit how far the drill bit 66 can be advanced axially into the surgical instrument 62. However, it will be appreciated that the drill bit 66 of the present disclosure could be configured in other ways sufficient to limit how far the drill bit 66 can be axially advanced into the surgical instrument 62. As is described in greater detail below, the resilient arm 188 is configured to axially retain the drill bit 66 to the driving cannula 116.

With reference to FIGS. 22-23, the interface 124 of the drill bit 66 extends along the axis AX between a distal interface end 194 and a proximal interface end 196. For the purposes of clarity and consistency, the distal interface end 194 and the proximal interface end 196 are defined herein as discrete locations along the length of the drill bit 66 between which the interface 124 has a generally consistent cross-sectional profile. However, it is contemplated that the distal interface end 194 and the proximal interface end 196 could be defined in other ways in some configurations. By way of illustrative example, it is conceivable that the interface 124 could comprise multiple discrete "interface regions" each having the same or different cross-sectional profiles which are delineated and spaced axially from each other along the shank 176, such as with cylindrical portions of the shank 176 extending therebetween. Other configurations are contemplated.

In the configuration of the drill bit 66 illustrated in FIGS. 22-23, a transition region 198 extends from the proximal interface end 196 to the proximal end 178 of the shank 176. Here, the transition region 198 effectively chamfers or "rounds-off" a portion of the interface 124 adjacent to the proximal end 178 of the shank 176 with a generally frusto-conical profile to define the proximal interface end 196. For the purposes of clarity and consistency, the proximal end 178 of the shank 176 illustrated herein is defined by the reduced diameter portion of the transition region 198 from which the resilient arms 188 extend. Put differently, the resilient arms 188 extend from the proximal end 178 of the shank 176 to respective arm ends 200, and the proximal end 178 of the shank 176 is distal from the arm ends 200. The resilient arms 188 will be described in greater detail below.

As noted above, the illustrated configuration of the bore 122 of the driving cannula 116 of the drive assembly 114 of the surgical instrument 62 has a generally rounded, hexagonal profile defined by six bore flats 122F and six bore corners 122C (see FIG. 18A), and the interface 124 of the drill bit 66 is configured to be received within the bore 122 to promote concurrent rotation between the drill bit 66 and the driving cannula 116 about the axis AX. To this end, the interface 124 of the drill bit 66 comprises at least one outermost drive portion 202 which is spaced from the axis AX at a first interface distance 204 (depicted schematically in FIGS. 29-33). In some configurations, the outermost portion 202 of the interface 124 is defined by an outer drive surface 206 facing away from the axis AX. Regardless, for the purposes of clarity and consistency, the first interface distance 204 and the outermost drive portion 202 are defined by whichever edge, apex, point, or surface of the interface 124 is spaced furthest from the axis AX. In some configurations, the interface 124 comprises a first outermost drive portion spaced from the axis AX at a first interface distance and a second outermost drive portion spaced from the axis AX at a second interface distance to define a maximum drive dimension 208 of the interface 124 (depicted schematically in FIGS. 29-33). In these configurations, the maximum drive dimension 208 is the "widest" portion of the interface 124. The first and second interface distances may comprise a common distance at which each of the first and second outermost drive portions is spaced from the axis AX, such that the arrangement of the first and second outermost drive portions relative to the axis AX is symmetrical. However, in other configurations, the first and second interface distances may not be equal to one another, such that the arrangement of the first and second outermost drive portions may be asymmetrical relative to the axis AX.

In some configurations, the interface 124 comprises at least one outer non-drive portion 210 which is spaced from the axis AX at a third interface distance 212 (depicted schematically in FIGS. 29-33). Further still, in some configurations, the outer non-drive portion 210 of the interface 124 is defined by an outer non-drive surface 214 which, in some configurations, may be defined as a planar interface surface. Regardless, for the purposes of clarity and consistency, the third interface distance 212 and the outer non-drive portion 210 are defined by whichever edge, apex, point, or surface of the interface 124 is spaced closest to the axis AX. In some configurations, the interface 124 comprises a first outer non-drive portion spaced from the axis AX at a third interface distance 212 and a second outer non-drive portion spaced from the axis AX at a fourth interface distance 212 to define a minimum interface dimension 216 of the interface 124 (depicted schematically in FIGS. 29-33). In these configurations, the minimum interface dimension 216 is the "narrowest" portion of the interface 124. The third and fourth interface distances may comprise a common distance at which each of the first and second outer non-drive portions is spaced from the axis AX, such that the arrangement of the first and second outer non-drive portions relative to the axis AX is symmetrical. However, in other configurations, the third and fourth interface distances may not be equal to one another, such that the arrangement of the first and second outer non-drive portions may be asymmetrical relative to the axis AX. Further still, two outer non-drive portions 210 are radially spaced about the axis AX from two outermost drive portions 202. However, as will be appreciated from the subsequent description below, the interface 124 could be configured in other ways sufficient to be received within and rotate concurrently with the bore 122 of the driving cannula 116.

Figure 29:
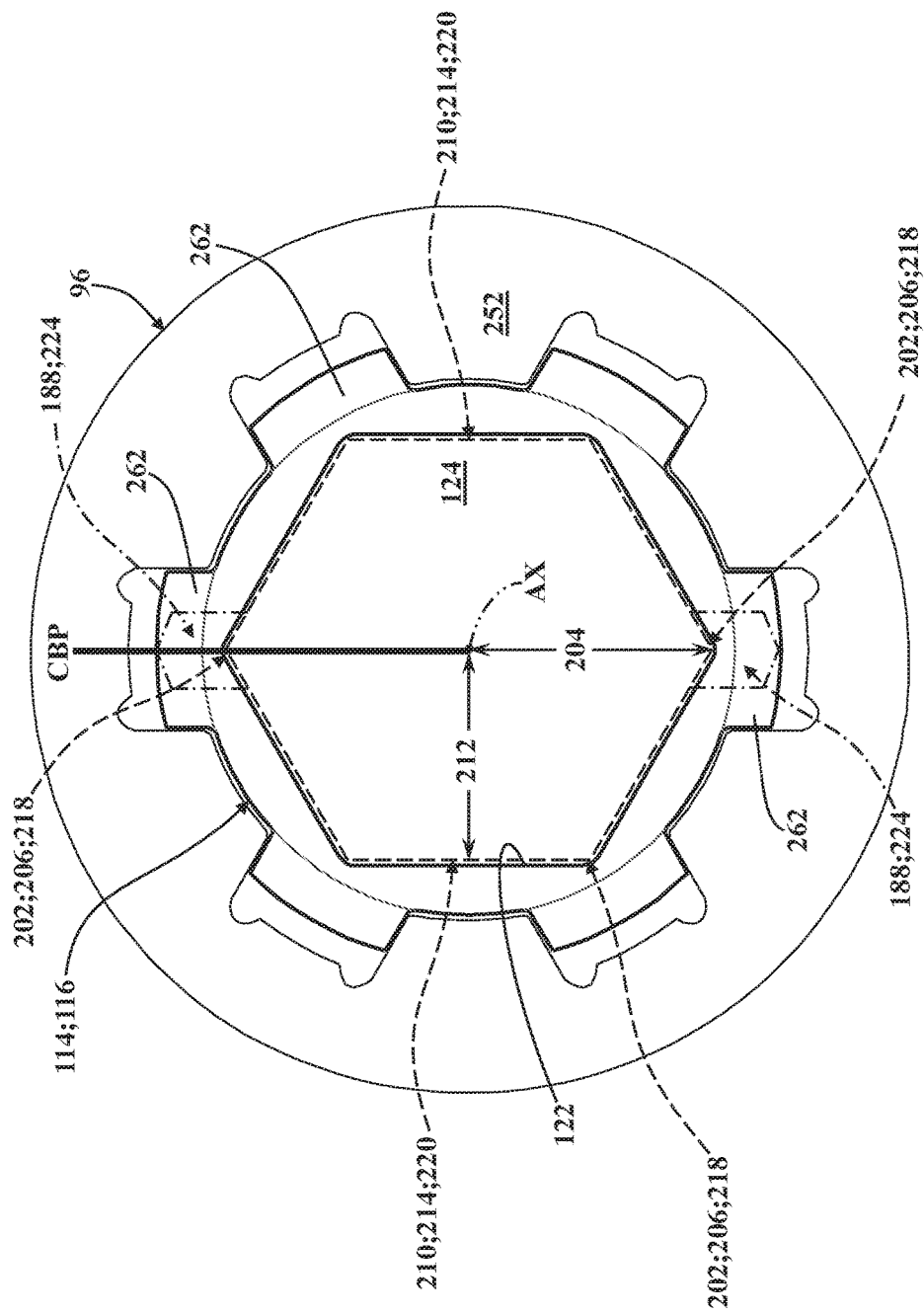
FIG. 29 is a front-side schematic view representing the driving cannula, the output hub, and the drill bit arranged as depicted in FIG. 15C, the schematic view showing the arrangement of the lock surfaces of the driving cannula delineated from one another by the splined engagement between the driving cannula and the output hub, the schematic view further showing the profile of the interface of the drill bit with dash-dash lines disposed within the bore of the driving cannula, and the schematic view still further showing the arrangement of the resilient arms with dash-dot-dash lines to illustrate abutment with the lock surfaces of the driving cannula as well as radial alignment of the retention surfaces of the resilient arms with respect to the profile of the interface.
Figure 30:
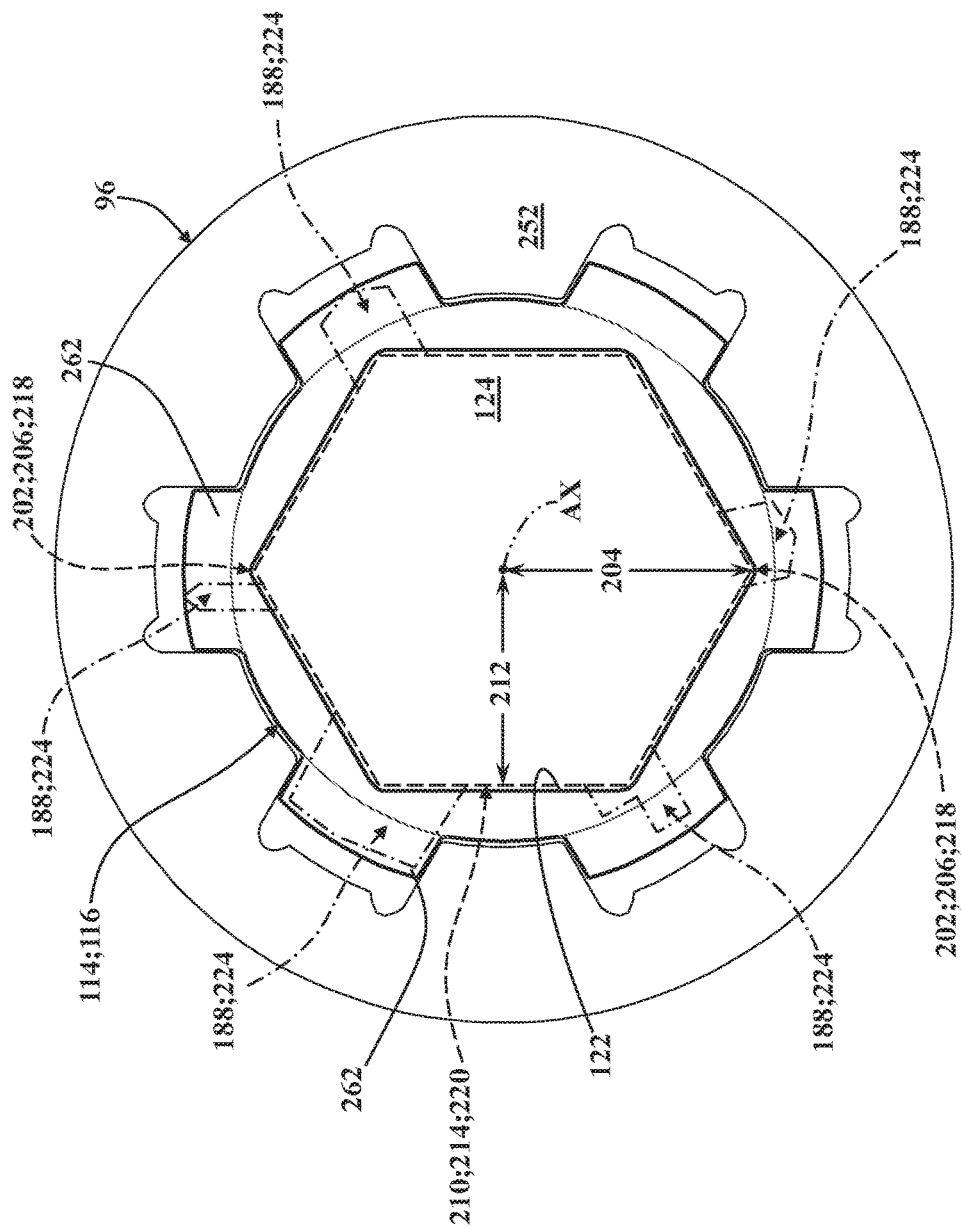
FIG. 30 is another front-side schematic view representing the driving cannula and the output hub of FIG. 29 with a configuration of a drill bit having resilient arms shown sized, shaped, and arranged in abutment with the lock surfaces of the driving cannula.

By way of illustrative example of the features of the interface 124 introduced above, the interface 124 of the configuration of the drill bit 66 depicted in FIGS. 18C and 20-24B, and depicted schematically in FIGS. 29 and 30, has a generally rounded hexagonal profile comprising a total of six outermost drive portions 202 and a total of six outer non-drive portions 210. Here, the six outermost drive portions 202 are each respectively defined by an outer drive surface 206 which is rounded to define a corner 218. Thus, in this configuration, the maximum drive dimension 208 is defined between the apexes of two diametrically opposed corners 218. Furthermore, in this configuration, the six outer non-drive portions 210 are each respectively defined by an outer non-drive surface 214 which is substantially flat to define a planar surface 220. Thus, in this configuration, the minimum interface dimension 216 is defined between the midpoints of two diametrically opposed planar surfaces 220.

As is described in detail below in connection with FIGS. 29-33, the interface 124 of the drill bit 66 of the present disclosure could have a number of different cross-sectional profiles or configurations sufficient to be received within and rotate concurrently with the bore 122. Thus, while the illustrated configurations of the interface 124 depicted in FIGS. 2, 4-5, 7C-7I, 15B, 17C, 18B-18C, and 20-30 have a generally rounded hexagonal profile which is complimentary to the profile of the bore 122 as described above, other configurations are contemplated by the present disclosure, including without limitation: other generally polygonal profiles such as a rectangle (see FIG. 31) or a star (see FIG. 32), irregular polygons, and/or other profiles and/or shapes which can be removably received within and rotate concurrently with the hexagonal bore 122 of the driving cannula 116 (see FIG. 33).

As noted above, the drill bit 66 of the present disclosure comprises one or more resilient arms 188 which extend from the proximal end 178 of the shank 176 to respective arm ends 200. The resilient arms 188 of the drill bit 66 are provided to, among other things, facilitate axially retaining the drill bit 66 to the surgical instrument 62 when the stop surface 190 of the drill bit 66 abuts the seat surface 192 of the driving cannula 116. As will be appreciated from the subsequent description below, the resilient arms 188 could be formed integrally with the shank 176 and could be machined, bent, and the like, or the resilient arms 188 could be formed separately from and subsequently attached to the shank 176, such as via welding, brazing, adhering, bonding, or any suitable process sufficient to operatively attach the resilient arms 188 to the shank 176.

With reference to FIGS. 20-23, the illustrated configuration of the insertion portion 72 of the drill bit 66 comprises resilient arms 188 which each have an outer arm surface 222 facing away from the axis AX, and a retention surface 224 facing toward the distal end 180 of the shank 176 (see FIG. 23). As is described in greater detail below in connection with FIGS. 29-33, the retention surface 224 of the resilient arm 188 is arranged so as to be radially aligned about the axis AX with one of the outermost drive portions 202 of the interface 124. Furthermore, as is described in greater detail below in connection with FIGS. 7A-7I, 15A-19C, and 29-33, the resilient arm 188 is configured so as to be movable relative to the axis AX between a first position P1 (see FIGS. 7B and 22) and a second position P2 (see FIGS. 7D-7E). In the first position P1, the outer arm surface 222 is spaced from the axis AX at a first arm distance 226 which is greater than the first interface distance 204. In the second position P2, the outer arm surface 222 is spaced from the axis AX at a second arm distance 228 which is less than the first arm distance 226 and, in some configurations, is less than or equal to the first interface distance 204. Put differently, the outer arm surface 222 of the resilient arm 188 is spaced further from the axis AX than any portion of the interface 124, and the resilient arm 188 is deflectable relative to the axis AX from the first position P1 toward the second position P2, and is resiliently biased toward the first position P1. As is described in greater detail below, this configuration helps facilitate releasable axial retention of the drill bit 66 to the surgical instrument 62 and, in some configurations, also affords self-aligning functionality to the drill bit 66 so as to index the interface 124 to the bore 122 by promoting rotation of the drill bit 66 about the axis AX during attachment to the surgical instrument 62 (see FIGS. 24A-24B, described in greater detail below).

Continuing the previous example above where the interface 124 comprises first and second outermost drive portions, the retention surface may be radially aligned with the first outermost drive portion. The outer arm surface 222 of the resilient arm 188 in the first position P1 may be spaced from the axis AX at the first arm distance, which may be greater than the first interface distance at which the first outermost drive portion is spaced from the axis AX. Furthermore, the outer arm surface 222 of the resilient arm 188 in the second position P2 may be spaced from the axis AX at the second arm distance, which may be less than the first arm distance and less than or equal to the first interface distance.

In another configuration, where the interface 124 comprises first and second outermost drive portions, the retention surface may not be radially aligned with the first outermost drive portion. Rather, the retention surface may be radially aligned with the second outermost drive portion. The outer arm surface 222 of the resilient arm 188 in the first position P1 may be spaced from the axis AX at a first arm distance, which in this configuration is greater than the second interface distance at which the second outermost drive portion is spaced from the axis AX. Furthermore, the outer arm surface 222 of the resilient arm 188 in the second position P2 may be spaced from the axis AX at a second arm distance, which is less than the first arm distance and less than or equal to the second interface distance.

As is best shown in FIG. 23, the outer arm surface 222 in the illustrated configuration is generally rectangular in profile, when viewed from the top, and is arranged between the arm end 200 and the retention surface 224. However, it will be appreciated that the outer arm surface 222 could be realized with outer configurations, profiles, arrangements, and the like. For the purposes of clarity and consistency, the outer arm surface 222 is defined by whichever surface, face, edge, apex, or point of the resilient arm 188 that is spaced furthest from the axis AX when the resilient arm 188 is in the first position P1.

With continued reference to FIGS. 20-23, the resilient arm 188 further comprises a ramp surface 230 which extends distally from the arm end 200 and merges with the outer arm surface 222. The ramp surface 230 is shaped and arranged so as to deflect the resilient arm 188 relative to the axis AX in response to engagement, contact, abutment, and the like. By way of example, in the illustrated configuration, the ramp surface 230 is shaped and arranged to engage against the tapered seat surface 192 of the driving cannula 116 of the drive assembly 114 (see FIG. 7C) in order to move the resilient arm 188 from the first position P1 to the second position P2 as the drill bit 66 is attached to the surgical instrument 62 (sequentially compare FIGS. 7B-7D). Similarly, in the illustrated configuration, the ramp surface 230 is shaped and arranged to engage the actuating element 174 of the release mechanism 150 (see FIGS. 7G-7H) as the slide element 164 translates distally along the axis AX in order to move the resilient arm 188 toward the second position P2 to facilitate removing the drill bit 66 from the surgical instrument 62 (sequentially compare FIGS. 7F-7I).

Referring now to FIGS. 20-24B, the illustrated configuration of the resilient arm 188 comprises an arm body 232 and a finger portion, generally indicated at 234. In one exemplary configuration, the arm body 232 has a generally linear profile with a generally arcuate portion which merges with the proximal end 178 of the shank 176. As best shown in FIG. 22, the arm body 232 extends away from the proximal end 178 of the shank 176. In the illustrated configuration, this configuration places the retention surface 224 at an arm position angle 236 (see FIG. 22) defined relative to the axis AX, which is generally oblique when the resilient arm 188 is in the first position P1 and which is generally perpendicular when the resilient arm 188 is in the second position P2. However, as will be appreciated from the subsequent description of the interaction between the insertion portion 72, the driving cannula 116, and the output hub 96, the retention surface 224 could be arranged or configured in other ways, such as to be at a non-perpendicular angle relative to the axis AX when the resilient arm 188 is in the second position P2. Other configurations are contemplated. Furthermore, while the arm body 232 extends away from the axis AX toward the arm end 200 in the illustrated configuration, it is conceivable that the arm body 232 could extend generally parallel with the axis AX in alternate configurations of the drill bit 66. In other configurations, the retention surface 224 can be arranged or configured relative to the resilient arm 188, such that the retention surface 224 is arranged at an 80-degree angle relative to the resilient arm 188. However, the retention surface can instead by arranged at any suitable angle above or below 80 degrees relative to the resilient arm.

The finger portion 234 of the resilient arm 188 is formed at the arm end 200 and, in the illustrated configurations, provides or otherwise defines the outer arm surface 222, the retention surface 224, and the ramp surface 230. As shown in FIG. 22, the finger portion 234 protrudes generally away from the axis AX to the outer arm surface 222. As shown in FIG. 23, the finger portion 234 defines a pair of outer finger surfaces 238 which are spaced at a finger width 240 from one another and are generally perpendicular to the retention surface 224. However, it will be appreciated that the finger portions 234 could be configured in a number of different ways, such as with a triangular profile, a rectangular profile, a rounded profile, a pentagonal profile, or other suitable profiles.

In the illustrated configuration, the finger portion 234 further comprises an aligning element, generally indicated at 242, arranged adjacent to the arm end 200. The aligning element 242 may be positioned at different locations on the resilient arm 188 besides the finger portion 234. Furthermore, fewer than all of the resilient arms 188 may include the aligning element 242. As will be appreciated from the subsequent description below, the aligning element 242 may comprise at least a portion of the outer arm surface 222, at least a portion of the ramp surface 230, and/or one or more planar arm surfaces 244 arranged adjacent to the outer arm surface 222 and to the ramp surface 230 (see FIGS. 20-23. Here, the planar arm surfaces 244 are arranged so as to be generally coplanar with respective planar surfaces 220 of outer non-drive surfaces 214 of the interface 124 when the resilient arm 188 is in the second position P2 (see FIG. 24B). In some configurations, the aligning element 242 may comprise a single planar arm surface 244. Moreover, while the illustrated configuration of the aligning element 242 employs a generally planar outer arm surface 222 arranged between two planar arm surfaces 244, it will be appreciated that other configurations are contemplated. By way of non-limiting example, the outer arm surface 222 could be realized as a discrete edge or point defined by a non-planar arm surface, formed such as with a wedge shape, where the discrete edge or point is arranged in radial alignment (e.g., co-linear with) one of the outermost drive portions 202 of the interface 124 when the resilient arm 188 is in the second position P2. In some configurations, such as those illustrated throughout the drawings, the aligning element 242 is shaped so as to mimic, mirror, or otherwise compliment the interface 124 when the resilient arm 188 is in the second position P2. Other configurations are contemplated, such as where the interface 124 is configured with a star-shaped profile with a plurality of drive lobes 245 spaced about the axis AX, such as the configuration illustrated in FIG. 32, the aligning element 242 may have a profile which at least partially replicates or otherwise compliments one of the drive lobes 245 (e.g., a triangular profile).

Figure 24A:
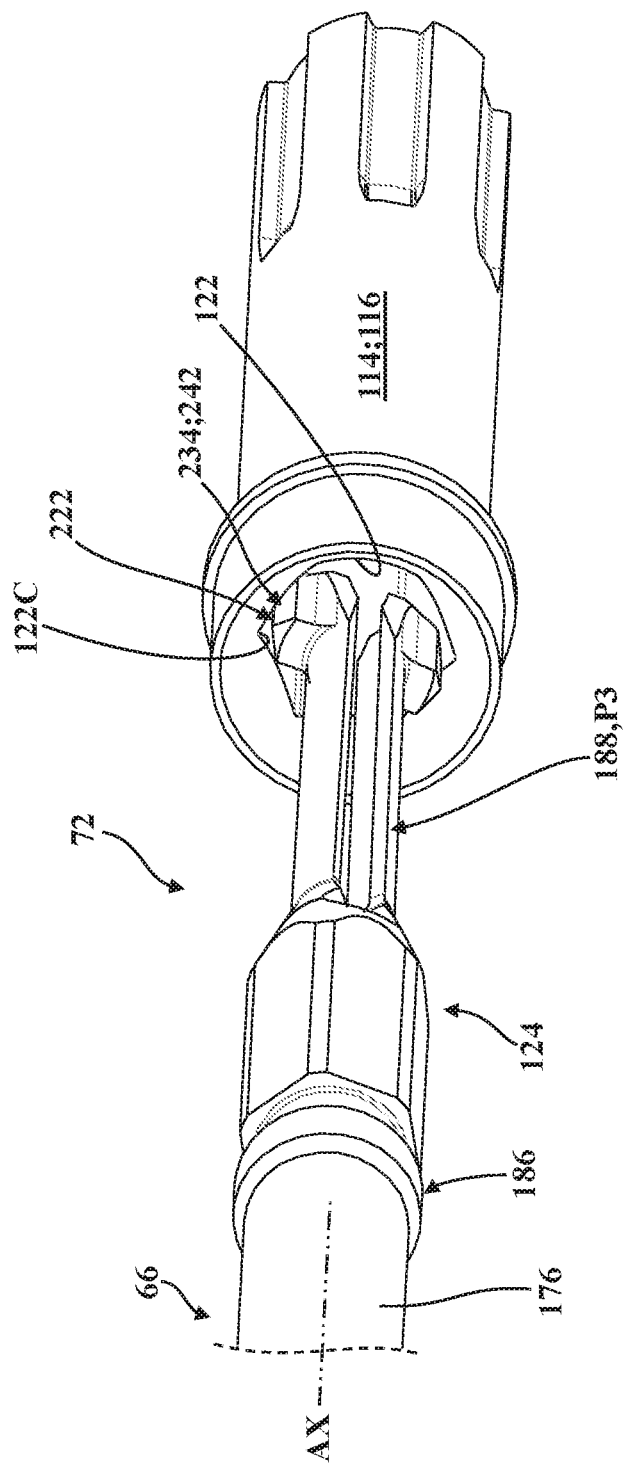
FIG. 24A is a partial perspective view of the drill bit of FIGS. 1-2, 4-5, 7B-7I, and 15B-15C and the driving cannula of FIGS. 15A-15B, shown with the interface of the drill bit misaligned with the bore of the driving cannula.
Figure 24B:
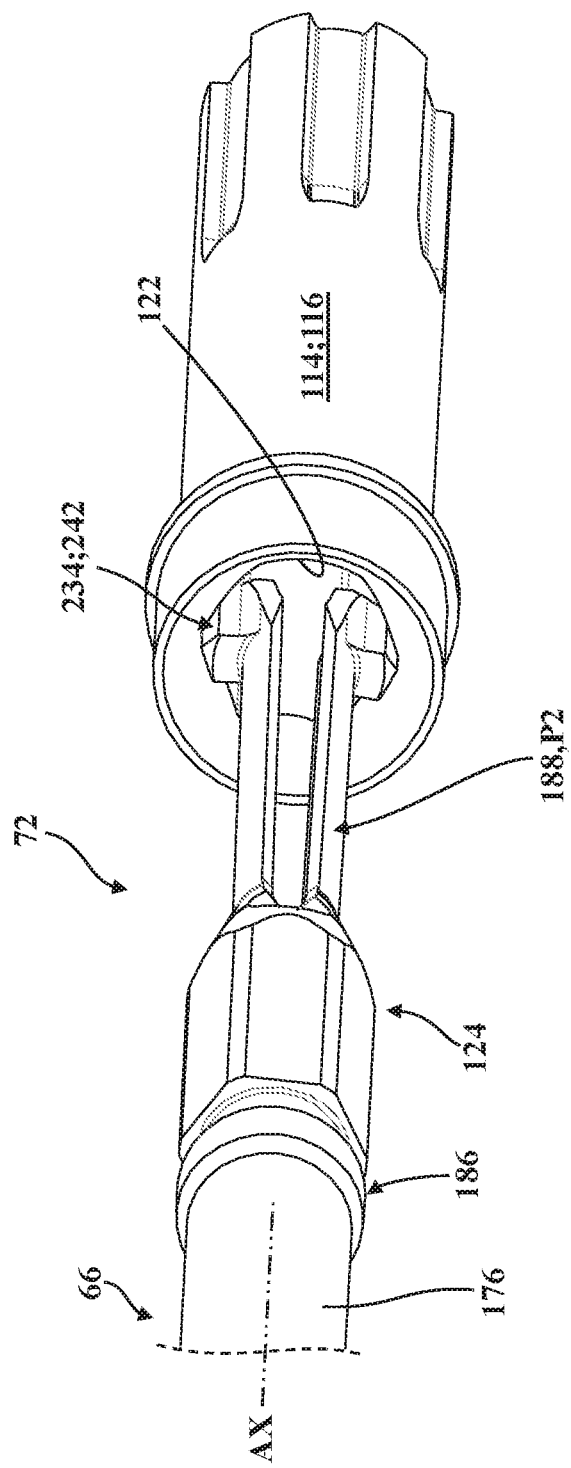
FIG. 24B is another partial perspective view of the drill bit and the driving cannula of FIG. 24A, shown with the interface of the drill bit subsequently aligned with the bore of the driving cannula.
Figure 25:
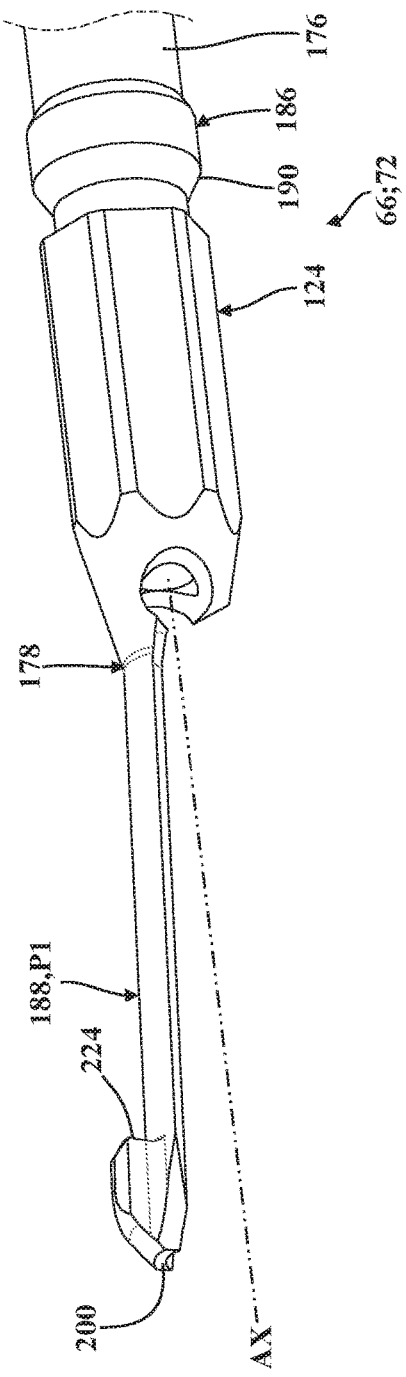
FIG. 25 is a partial perspective view of another drill bit configuration, shown having a single resilient arm.
Figure 26:
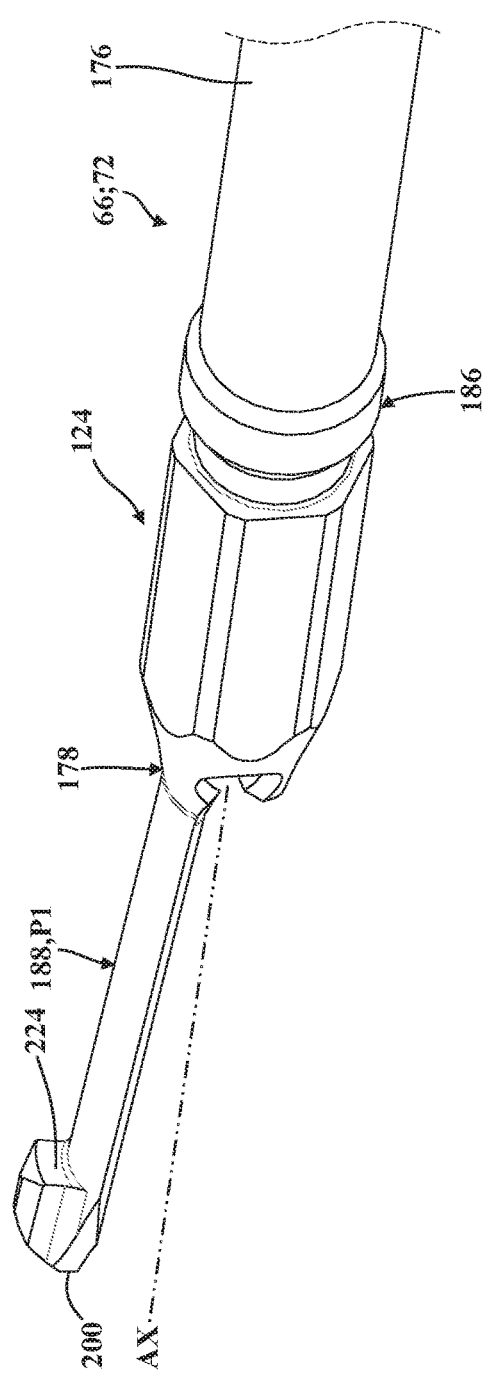
FIG. 26 is another partial perspective view of the configuration of the drill bit illustrated in FIG. 25.
Figure 27:
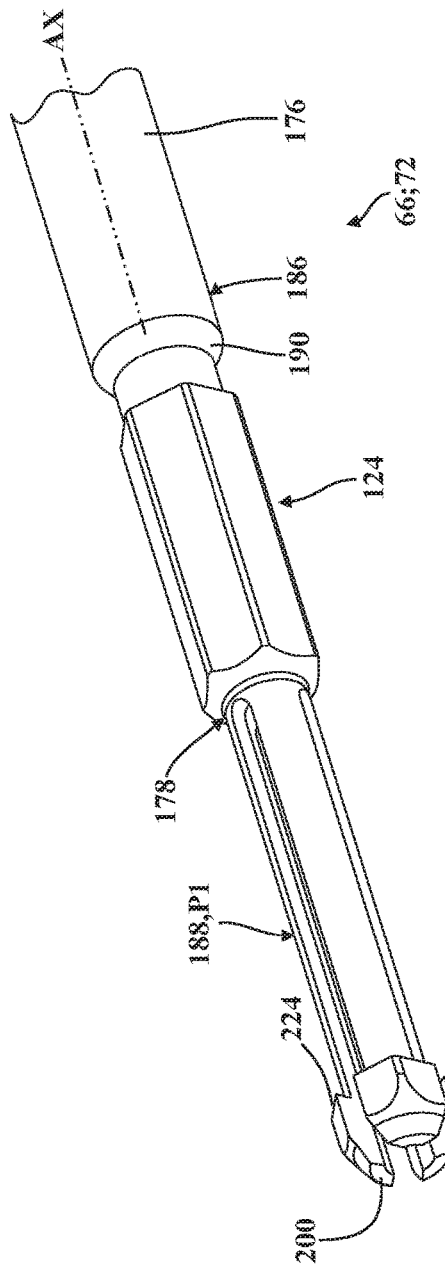
FIG. 27 is a partial perspective view of another drill bit configuration, shown having three resilient arms.
Figure 28:
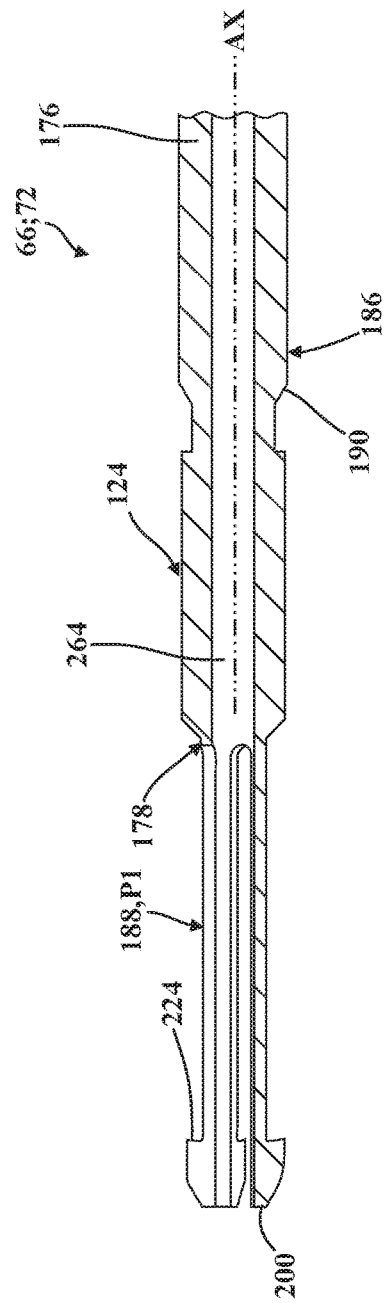
FIG. 28 is a partial longitudinal sectional view of the configuration of the drill bit illustrated in FIG. 27, shown having a cannulated shank.

The aligning element 242 is employed to facilitate at least partial rotation of the drill bit 66 about the axis AX as the resilient arm 188 moves from the first position P1 to the second position P2 in response to force applied to the drill bit 66 along the axis AX during attachment to the surgical instrument 62. More specifically, as shown in FIGS. 24A-24B, as the resilient arm 188 moves toward the second position P2 in response to engagement with the tapered seat surface 192 of the driving cannula 116, one or more portions of the aligning element 242 are disposed in abutment with the tapered seat surface 192. Here, because potential energy is stored in the resilient arm 188 when deflected away from the first position P1, the abutment between the tapered seat surface 192 and one or more portions of the aligning element 242 promotes at least partial rotation of the drill bit 66 relative to the driving cannula 116 as the aligning element 242 is advanced from the tapered seat surface 192 of the driving cannula 116 into the bore 122 of the driving cannula 116. Thus, as the resilient arm 188 enters the bore 122, the drill bit 66 "self-aligns" with the bore 122 in that the rotation of the drill bit 66 about the axis AX is caused by the outer arm surface 222 being urged toward one of the bore corners 122C, and the planar arm surfaces 244 of the aligning element 242 are brought into respective engagement with the adjacent bore flats 122F (compare FIGS. 24A-24B).

In this configuration, the resilient arm 188 moves from the first position P1 at the first arm distance relative to the axis AX indirectly to the second position P2 (FIG. 24B) at the second arm distance relative to the axis AX. More specifically, the resilient arm 188 can move from the first position P1 directly to a third position P3 (FIG. 24A) at a third distance relative to the axis AX and from the third position P3 directly to the second position P2 (FIG. 24B). The first arm distance relative to the axis AX may be greater than the first interface distance 204 between the outermost drive portion 202 and the axis AX. The third arm distance relative to the axis AX may be less than each of the first arm distance and the first interface distance 204. The second arm distance relative to the axis AX may be greater than the third arm distance and less than or equal to the first interface distance 204.

When the resilient arm 188 is disposed in the third position, the outer arm surface 222 engages one of the bore flats 122F. Because the resilient arm 188 is urged away from the axis AX, movement of the outer arm surface 222 from the bore flat 122F to one of the bore corners 122C causes the resilient arm 188 to move from the third position (FIG. 24A) to the second position P2 (FIG. 24B) which, in turn, causes the drill bit to rotate into alignment with the bore. However, it is contemplated that, when the drill bit is already aligned with the bore prior to insertion into the bore and force is applied to the drill bit 66 along the axis AX, the resilient arm can move from the first position P1 directly to the second position P2.

Because the planar arm surfaces 244 are generally coplanar with planar surfaces 220 of the interface 124 when the resilient arm 188 is in the second position P2, the rotation described above "indexes" the interface 124 of the drill bit 66 with the bore 122 of the driving cannula 116 once the finger portion 234 is received within the bore 122 and the outer arm surface 222 is received in one of the bore corners 122C. While this configuration affords advantages in connection with attaching the end effector assembly 64 to the surgical instrument 62, by "self-aligning" the interface 124 of the drill bit 66 with the bore 122 of the driving cannula 116, it will be appreciated that the drill bit 66 could be configured in other ways, such as with different types of aligning elements 242 and/or finger portions 234. By way of non-limiting example, the drill bit 66 could omit the aligning element 242 and/or the finger portions 234 in some configurations. Other configurations are contemplated.

Figure 15A:
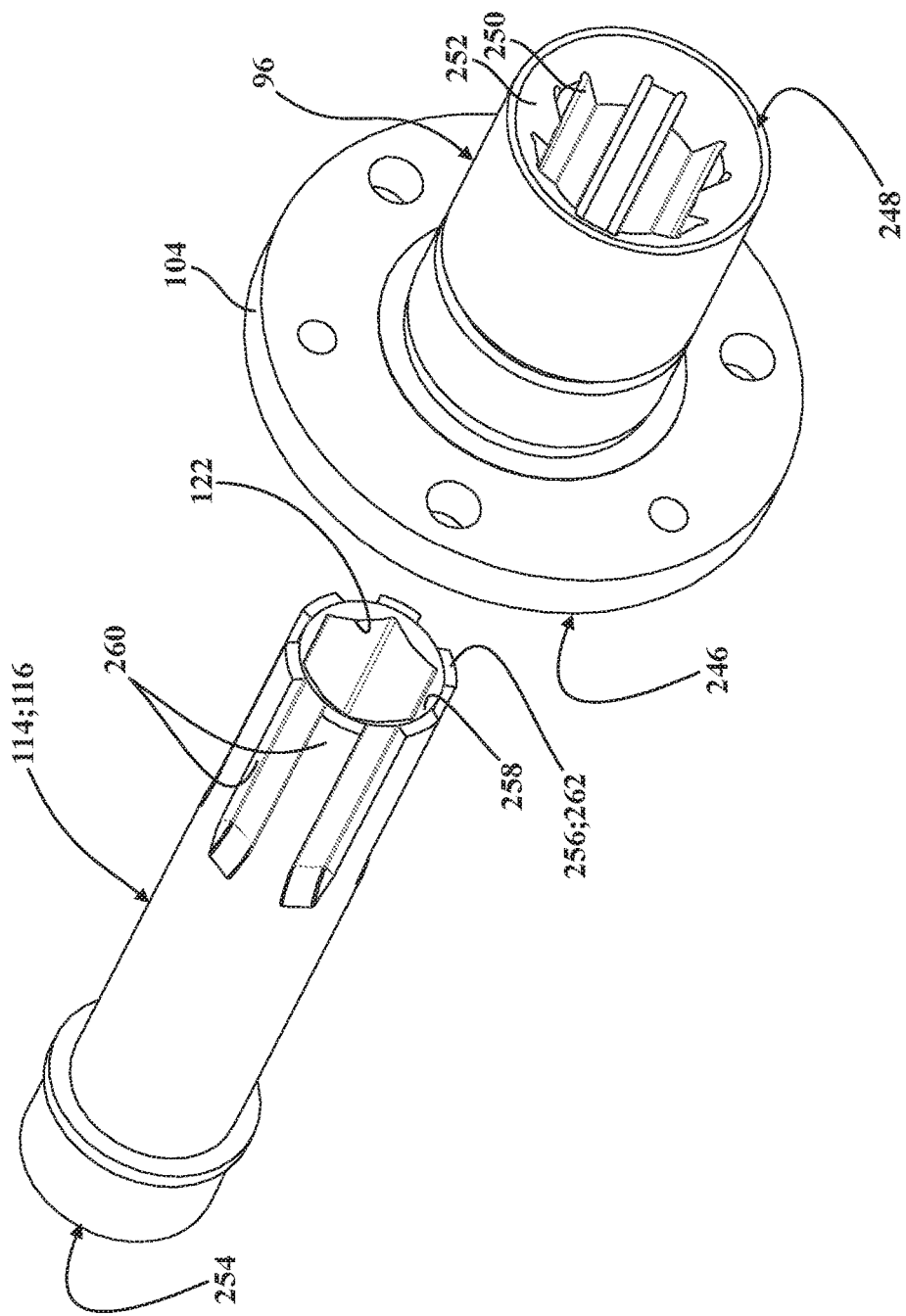
FIG. 15A is a perspective view showing the driving cannula of the drive assembly depicted in FIGS. 2-8 positioned adjacent to the output hub of the gearset depicted in FIGS. 3-7I and 9-11.

Referring now to FIGS. 15A-19C, as noted above, the driving cannula 116 of the drive assembly 114 cooperates with the output hub 96 of the actuator assembly 82 to facilitate rotating the drill bit 66 about the axis AX via splined engagement between the output hub 96 and the driving cannula 116. As is best shown in FIGS. 15A and 17A, the output hub 96 extends between a distal hub end 246 and a proximal hub end 248, and comprises one or more internal splines 250 which extend from the distal hub end 246, adjacent to the integrated carrier 104, toward but spaced from the proximal hub end 248. Here, the output hub 96 is provided with a lockout taper 252 which has a generally frustoconical profile extending internally to merge with the internal splines 250 such that the internal splines 250 terminate distal from the proximal hub end 248.

Figure 17A:
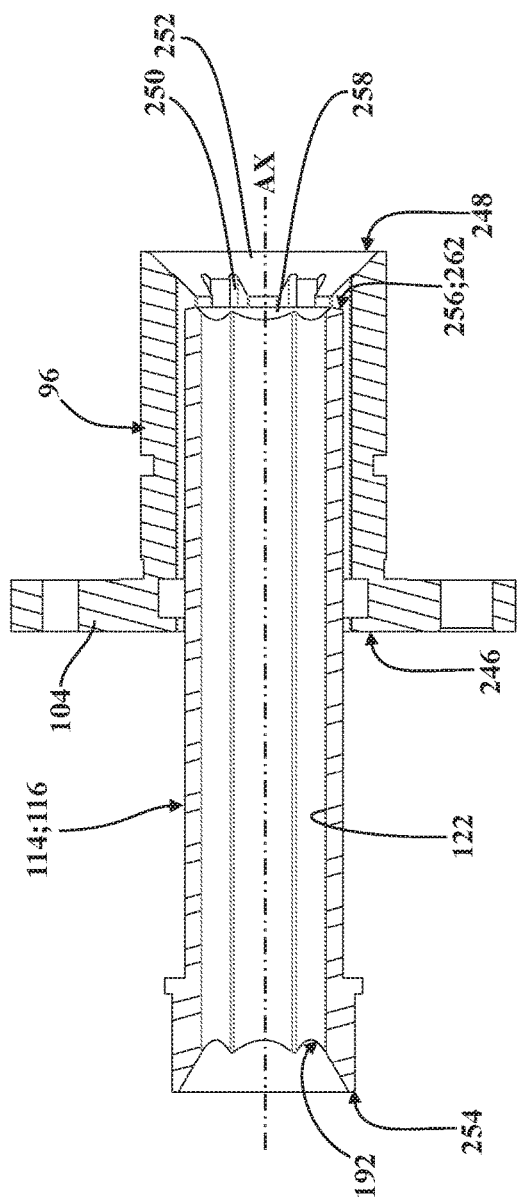
FIG. 17A is a sectional view taken along line 17-17 in FIG. 16, depicting the driving cannula disposed within the output hub as illustrated in FIG. 15B.
Figure 19A:
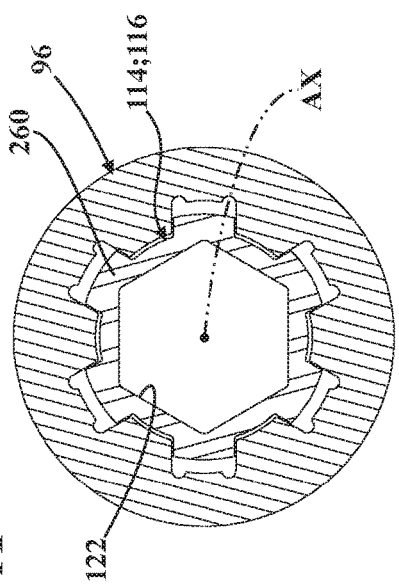
FIG. 19A is a sectional view taken along line 19-19 in FIG. 16, depicting splined engagement between the driving cannula and the output hub adjacent to the lock surfaces of the driving cannula.
Figure 18A:
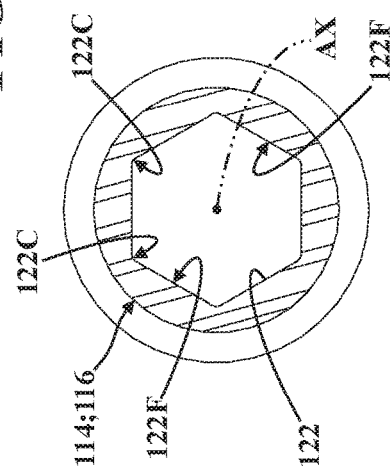
FIG. 18A is a sectional view taken along line 18-18 in FIG. 16, depicting the profile of the bore of the driving cannula.
Figure 17B:
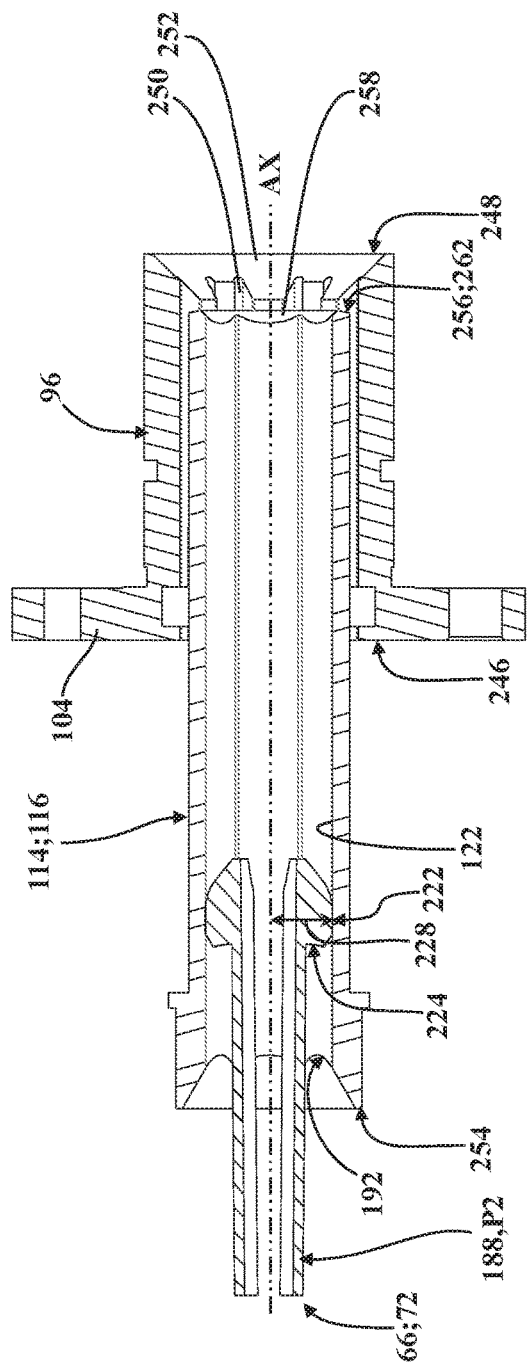
FIG. 17B is another sectional view of the driving cannula and the output hub of FIG. 17A, shown with the resilient arms of the drill bit of FIGS. 1-2, 4-5, 7B-7I, and 15B-15C disposed within the bore of the driving cannula.
Figure 18B:
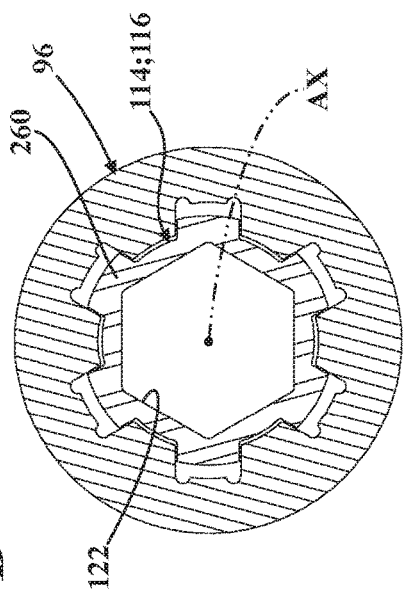
FIG. 18B is another sectional view of the driving cannula of FIG. 18A, shown with the resilient arms of the drill bit of FIGS. 1-2, 4-5, 7B-7I, and 15B-15C disposed within and abutting against the bore of the driving cannula, the drill bit being arranged as illustrated in FIG. 17B.
Figure 19B:
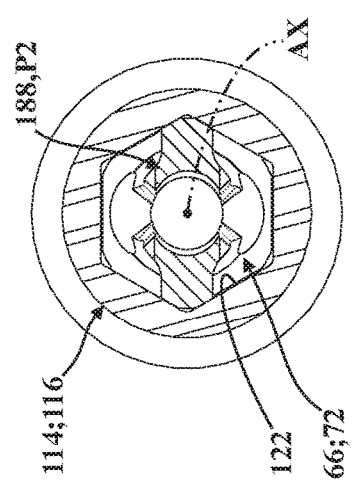
FIG. 19B is another sectional view of the driving cannula and the output hub.
Figure 17C:
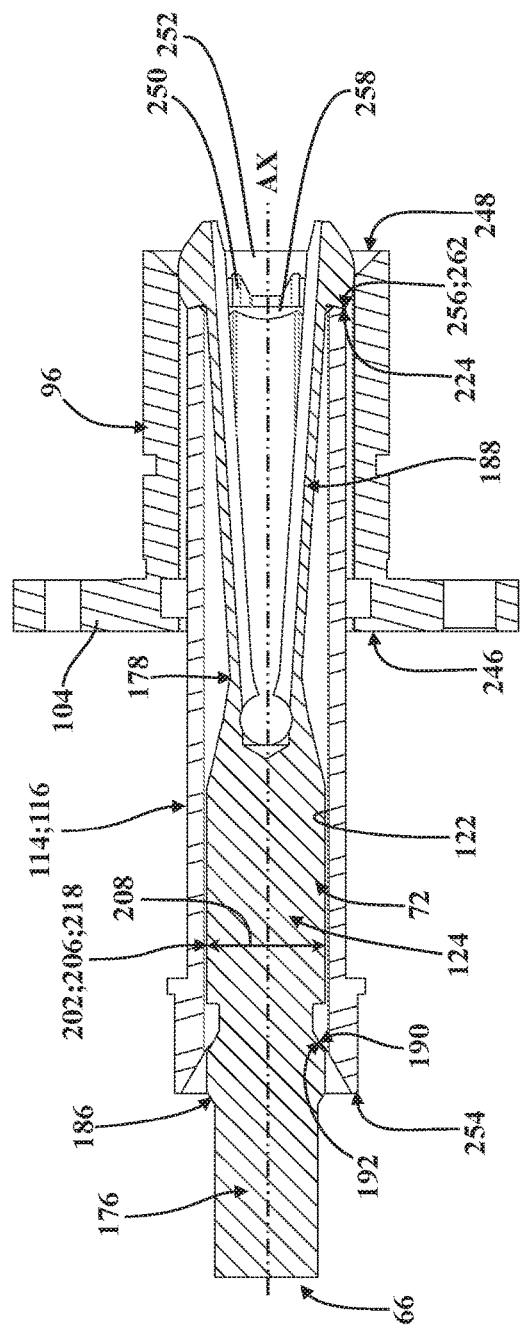
FIG. 17C is another sectional view of the driving cannula, the output hub, and the drill bit of FIG. 17B, shown with the resilient arms of the drill bit disposed in abutment with the lock surfaces of the driving cannula as illustrated in FIG. 15C.
Figure 19C:
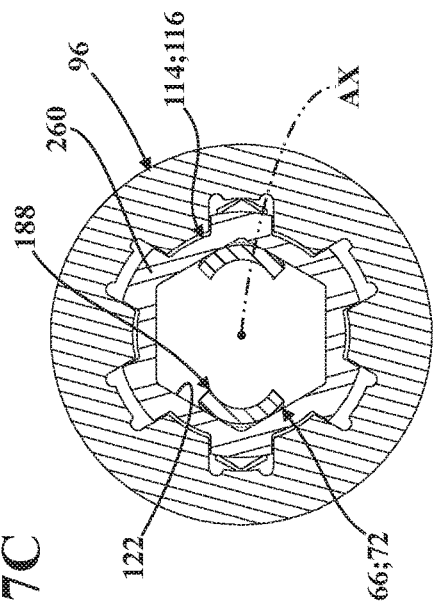
FIG. 19C is another sectional view of the driving cannula and the output hub of FIGS. 19A-19B, shown with portions of the resilient arms of the drill bit disposed within and abutting against the bore of the driving cannula, the drill bit being arranged as illustrated in FIG. 17C.
Figure 18C:
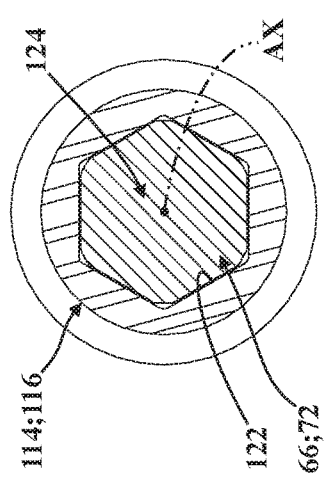
FIG. 18C is another sectional view of the driving cannula and the drill bit of FIG. 18B, shown with the interface disposed within the bore of the driving cannula.
Figure 20:
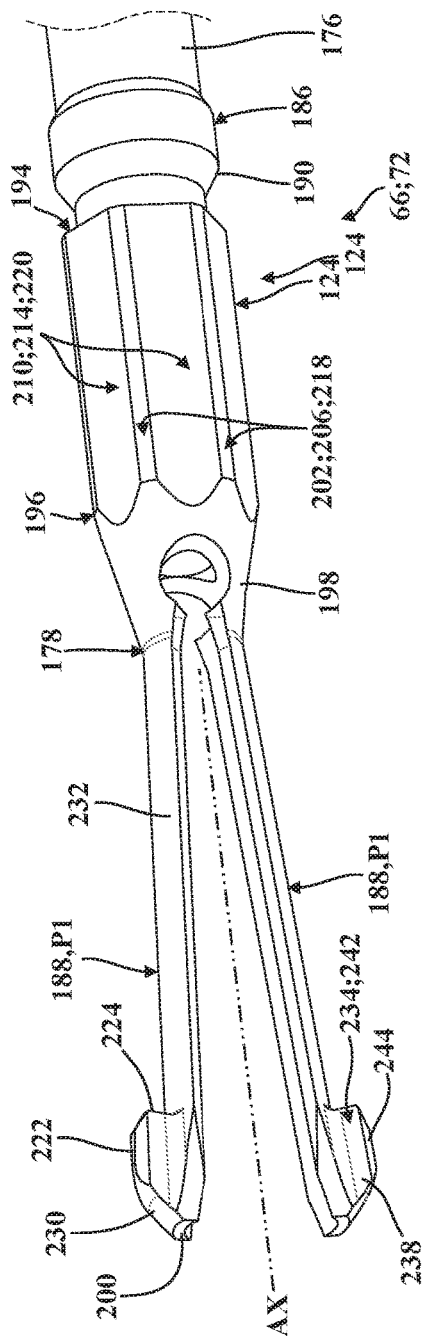
FIG. 20 is a partial perspective view of the drill bit of FIGS. 1-2, 4-5, 7B-7I, 15B-15C, 17B-17C, and 19B-19C showing additional detail of the resilient arms, the interface, and the stop adjacent to the proximal end of the shank.
Figure 21:
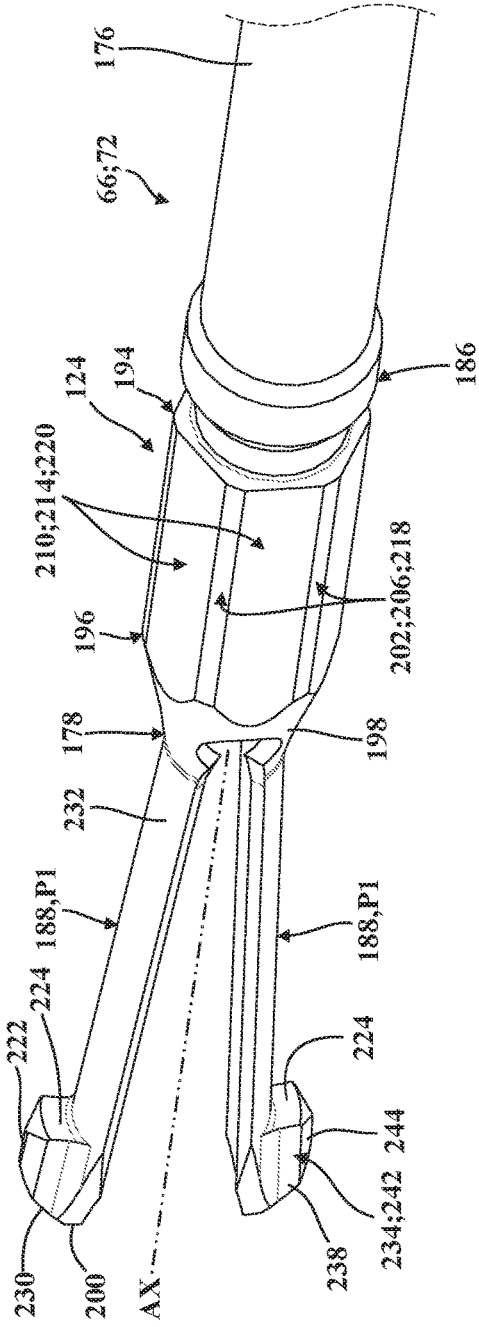
FIG. 21 is another partial perspective view of the portions of the drill bit illustrated in FIG. 20.

With continued reference to FIGS. 15A and 17A, the driving cannula 116 extends between a distal driving cannula end 254 and a proximal driving cannula end 256. Here, the tapered seat surface 192 is formed at the distal driving cannula end 254 and tapers internally into the hexagonal bore 122, as noted above. The bore 122, in turn, extends along the axis AX toward the proximal driving cannula end 256. In order to help facilitate releasing the drill bit 66 from the surgical instrument, the driving cannula 116 is provided with a release taper 258 which similarly tapers internally into the hexagonal bore 122 (see FIG. 17A). The driving cannula 116 further comprises external splines 260 which are formed extending from the proximal driving cannula end 256 toward but spaced from the distal driving cannula end 254. At the proximal driving cannula end 256, the external splines 260 define lock surfaces 262 adjacent to the release taper 258. The lock surfaces 262 are arranged to abut the retention surface 224 of the resilient arm 188 to axially lock the drill bit 66 to the surgical instrument 62. The specific shape and arrangement of the internal splines and external splines can be adjusted to different arrangements or geometries so long as the lock surfaces are still present and arranged relative to the bore in a way that makes the lock surfaces accessible to the retention surfaces of the bit when the drive interface is received in the bore.

Figure 15B:
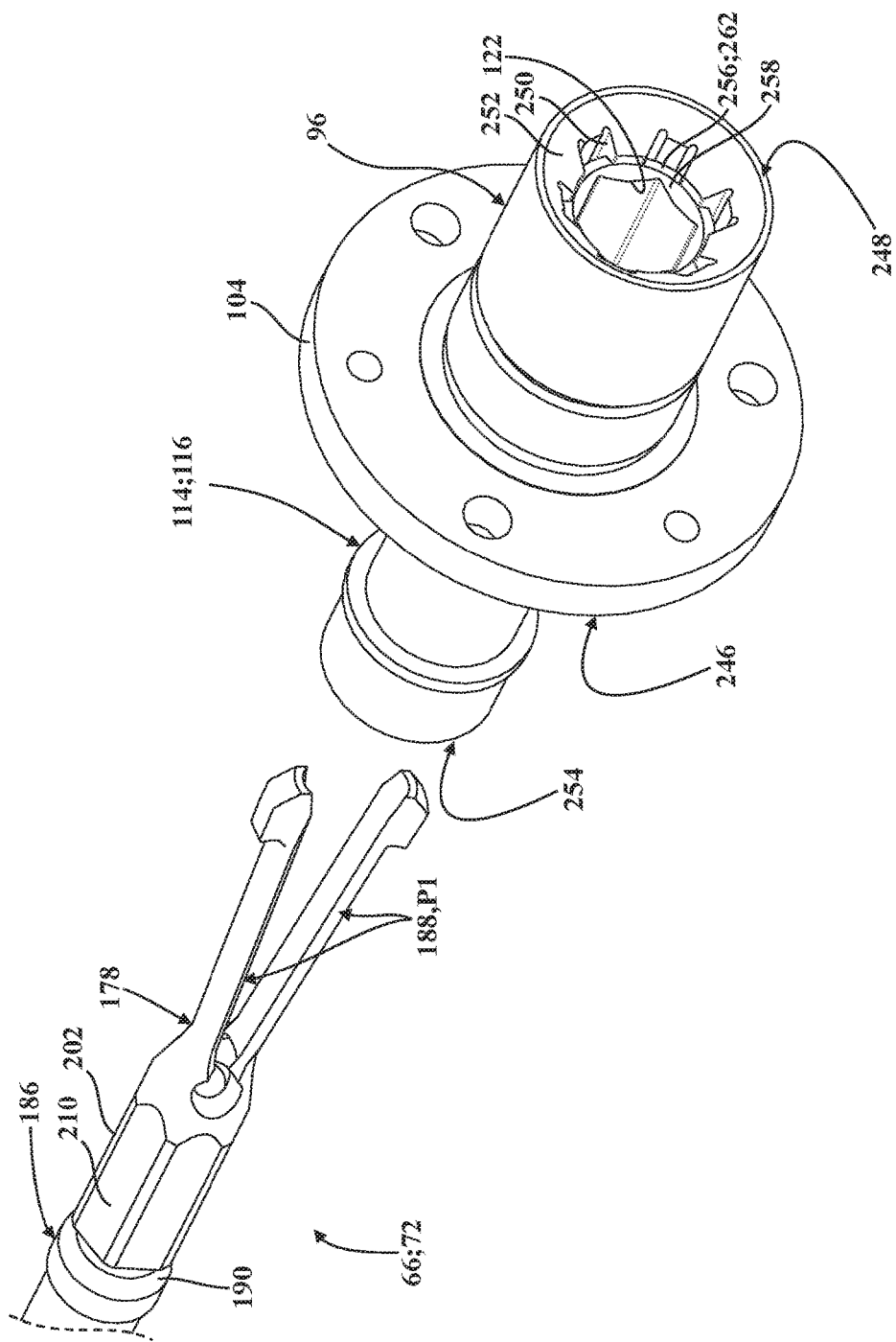
FIG. 15B is a perspective view of the driving cannula and the output hub of FIG. 15A assembled for concurrent rotation via splined engagement, shown positioned adjacent to the resilient arms extending from the proximal end of the shank of the drill bit of FIGS. 1-2, 4-5, and 7B-7I.
Figure 15C:
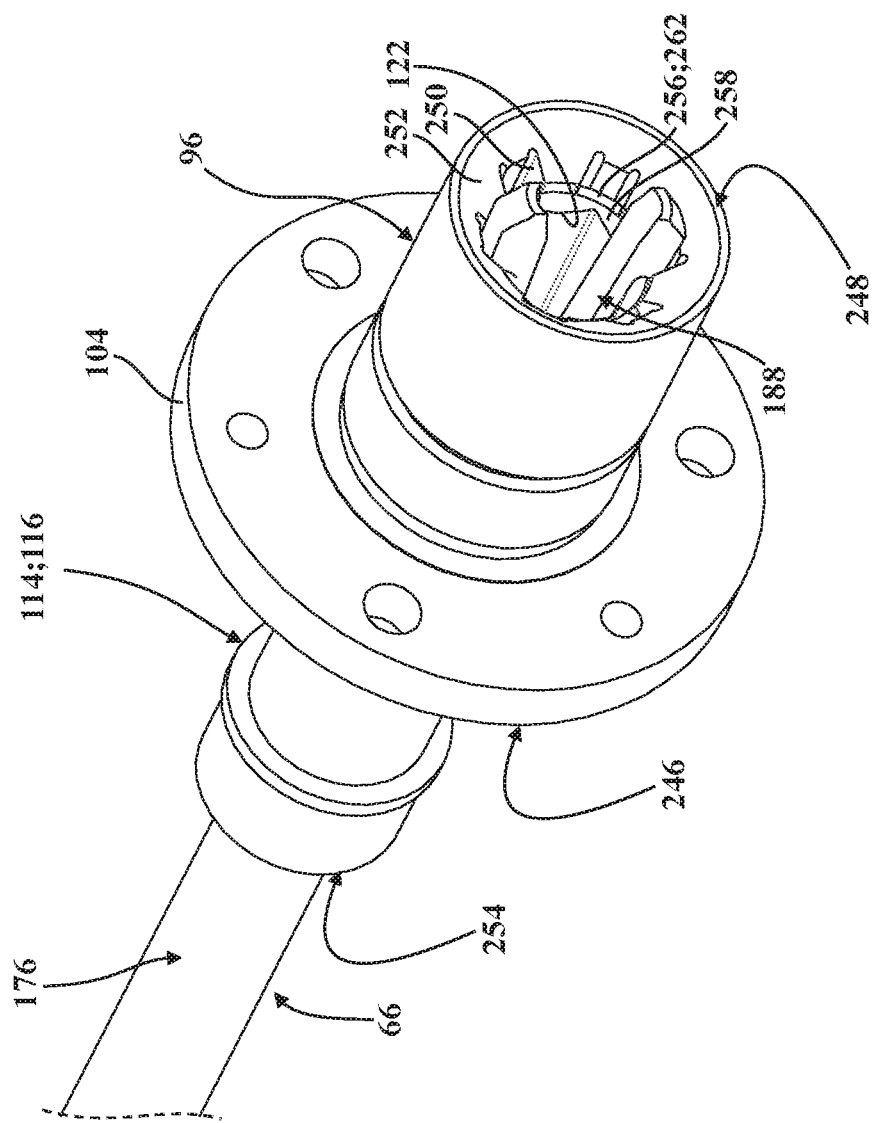
FIG. 15C is another perspective view of the driving cannula, the output hub, and the drill bit of FIG. 15B, shown with the resilient arms of the drill bit disposed in abutment with the lock surfaces of the driving cannula.
Figure 16:
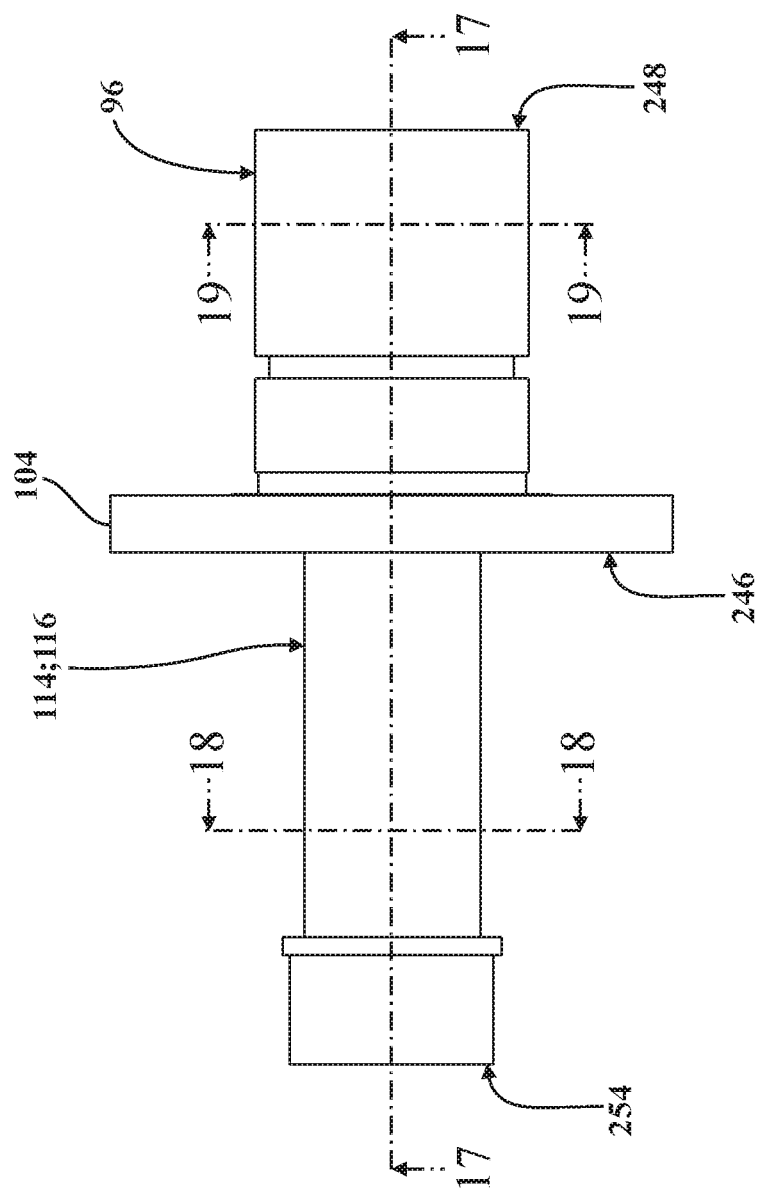
FIG. 16 is a top-side view of the driving cannula and the output hub assembled as depicted in FIG. 15B.

As shown best in FIGS. 15B, 17A, and 17C, because the proximal driving cannula end 256 is spaced distally from the proximal hub end 248 of the output hub 96, the lock surfaces 262 of the driving cannula 116 are likewise spaced distally from the proximal hub end 248 and, in the illustrated configuration, the lock surfaces 262 are also spaced distally from the lockout taper 252 of the output hub 96. This configuration ensures that axial retention of the drill bit 66 is effected via engagement between the retention surface 224 of the resilient arm 188 and one of the lock surfaces 262 of the driving cannula 116, and not with other portions of the driving cannula 116 or the output hub 96. Put differently, the lockout taper 252 of the output hub 96 and the release taper of the driving cannula 116 are arranged and configured not to remain in abutting engagement with the retention surface 224 of the resilient arm 188 in a way that would allow the drill bit 66 to be axially retained. Moreover, as is generally depicted in FIGS. 17A-19C, the external splines 260 of the driving cannula 116 are radially arranged about the axis AX relative to the bore 122. Thus, because the external splines 260 of the driving cannula 116 define the lock surfaces 262 and are radially arranged with the bore 122 adjacent to the bore corners 120C, the retention surface 224 of the resilient arm 188 needs to be radially aligned about the axis with the outermost drive portion 202 of the interface 124 in order to engage one of the lock surfaces 262.

As will be appreciated from the subsequent description below, the insertion portion 72 of the drill bit 66 may be configured in different ways sufficient to releasably attach to the surgical instrument. By way of non-limiting example, in some of the illustrated configurations, such as those depicted in FIGS. 20-23, the insertion portion 72 comprises a pair of generally identical, diametrically opposed resilient arms 188, each having respective retention surfaces 224 radially aligned with respective outermost drive portions 202 of the interface 124. However, it will be appreciated that other configurations are contemplated. By way of non-limiting example, it is conceivable that the insertion portion 72 could comprise two resilient arms 188 which are radially spaced from outermost drive portions 202 about the axis AX at 60 degrees, or at intervals thereof (generally illustrated schematically in FIGS. 30 and 32-33). Other intervals are contemplated, such as 15 degrees, 30 degrees, 45 degrees, or intervals of each. In some configurations, the resilient arm 188 and one of the outermost drive portions 202 are positioned within 15 degrees of one another relative to the axis AX.

Furthermore, it is conceivable that the insertion portion 72 could comprise a plurality of resilient arms 188 with different or similar configurations from one another, such as with differently shaped, sized, or angled retention surfaces 224, finger portions 234, aligning elements 242, and the like (illustrated schematically in FIG. 30). Further still, it will be appreciated that the insertion portion 72 could comprise a single resilient arm 188, such as is depicted in the configuration illustrated in FIGS. 25-26, or could comprise more than two resilient arms 188, such as is depicted in the configuration illustrated in FIGS. 27-28 which comprises three resilient arms 188. Furthermore, the configurations of the interface 124 illustrated schematically in FIGS. 32-33 could each have between one and six resilient arms 188. Moreover, while some of the configurations of the interface 124 comprise resilient arms 188 which are diametrically spaced from each other about the axis AX and have similar or identical profiles, other arrangements are contemplated. By way of example, the interface 124 illustrated schematically in FIG. 30 is shown as being able to comprise five resilient arms 188 of various configurations (e.g., with retention surfaces 224 of different profiles and orientations). Other configurations are contemplated.

While the illustrated drill bit 66 is configured as a twist drill with helical flutes 182 to promote tissue penetration, other types of cutting tip portions 70 could be employed in some configurations. For example, the cutting tip portion 70 could be realized as a burr, a reamer, a tap, a screw driver, and the like. Moreover, as shown in the configuration illustrated in FIG. 28, the drill bit 66 may further comprise a drill cannula 264 extending along the axis AX such that the drill bit 66 is cannulated in some configurations.

As noted above, the interface 124 of the drill bit 66 of the present disclosure could have a number of different cross-sectional profiles or configurations sufficient to be received within and rotate concurrently with the bore 122. In some configurations, the interface 124 may comprise different numbers of planar surfaces 220. By way of illustration, the configurations of the interface 124 illustrated in FIGS. 29-32 each comprise at least four planar surfaces 220: six in the configurations illustrated in FIGS. 29-30, four in the configuration illustrated in FIG. 31, and twelve in the configuration illustrated in FIG. 32. However, other configurations may employ fewer than four planar surfaces 220, such as the configuration illustrated in FIG. 33 which comprises two planar surfaces. It will be appreciated that other arrangements and configurations of the interface 124 and/or the planar surfaces 220 are contemplated.

Figure 31:
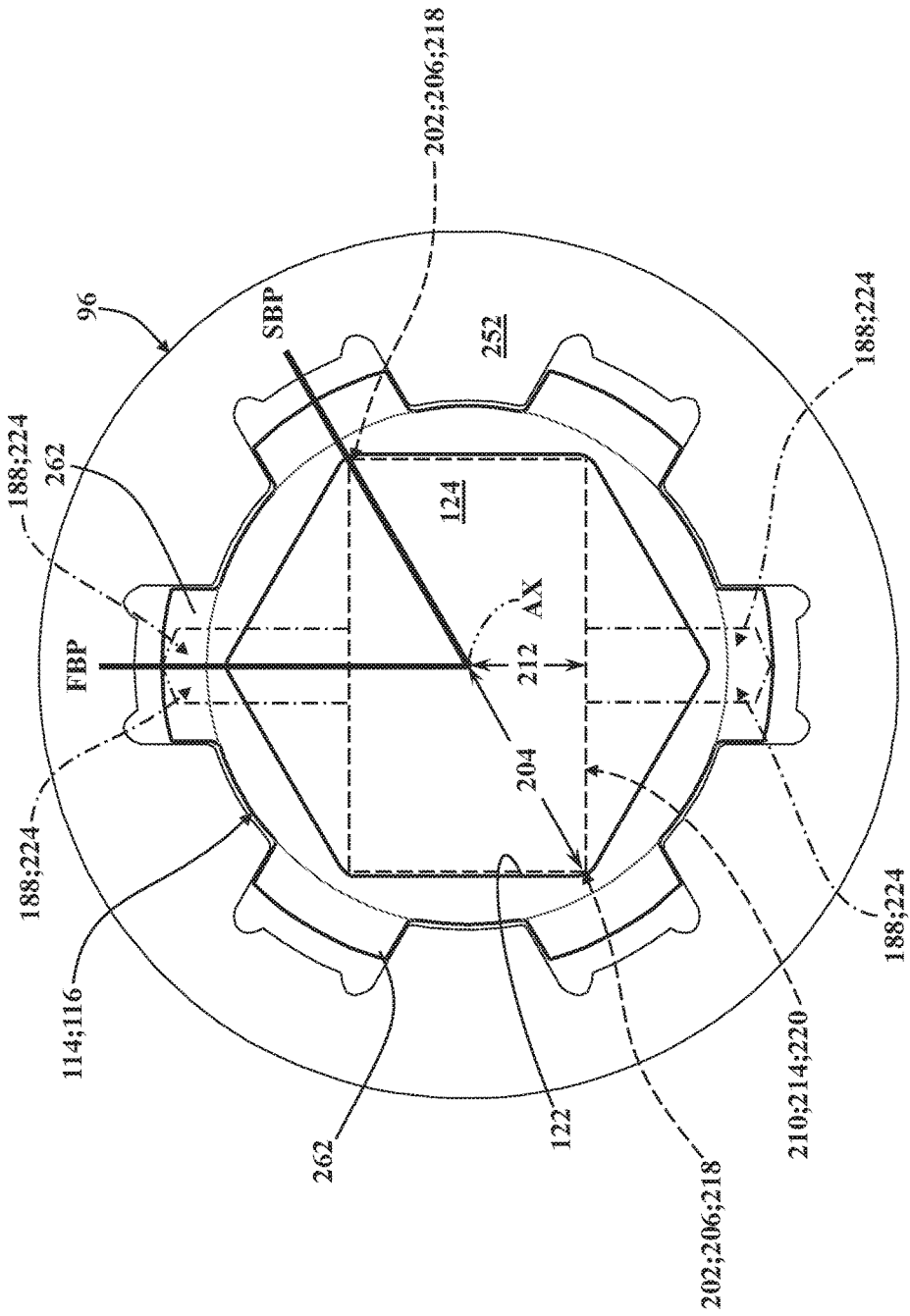
FIG. 31 is another front-side schematic view representing the driving cannula and the output hub of FIGS. 29-30 with a configuration of a drill bit having an interface shown with a generally rectangular profile.
Figure 32:
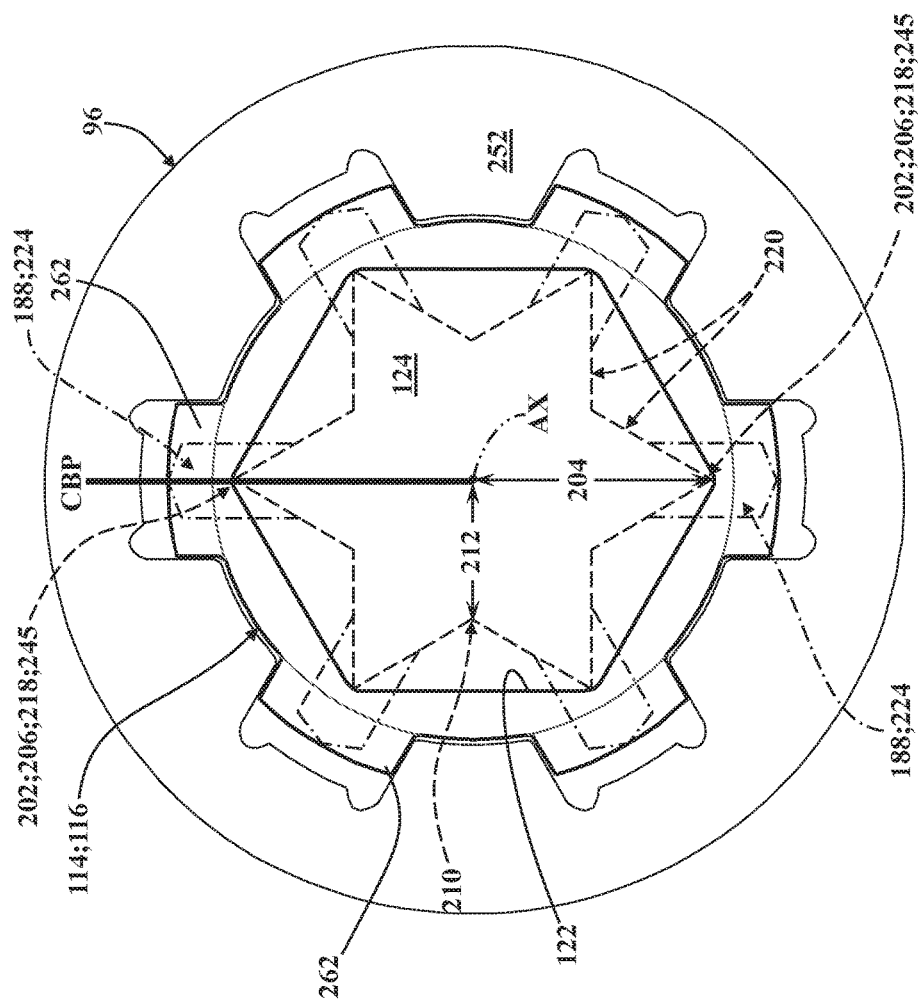
FIG. 32 is another front-side schematic view representing the driving cannula and the output hub of FIGS. 29-31 with a configuration of a drill bit having an interface shown with a generally star-shaped profile.
Figure 33:
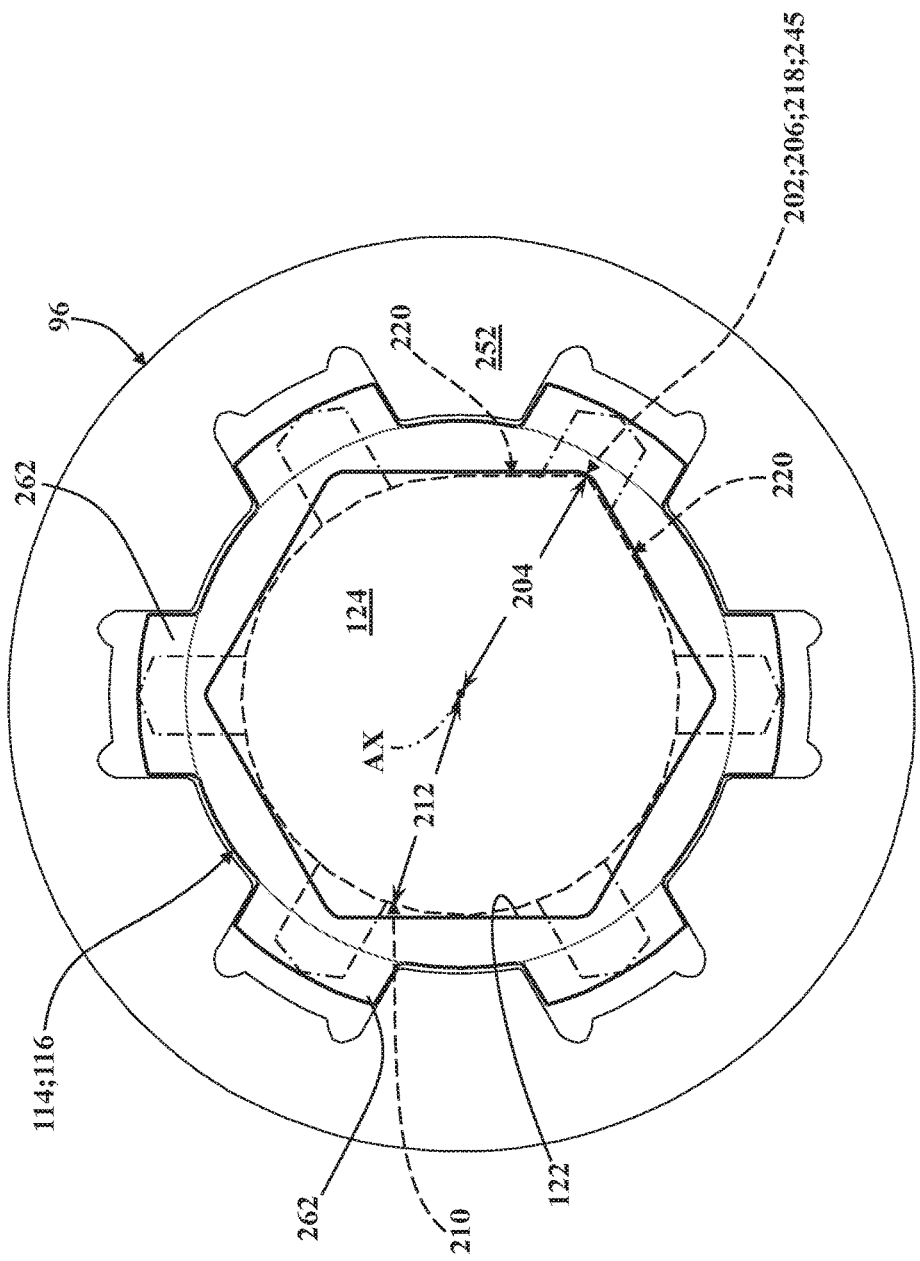
FIG. 33 is another front-side schematic view representing the driving cannula and the output hub of FIGS. 29-32 with a configuration of a drill bit having an interface shown with an irregularly-shaped profile.

In some configurations, the interface 124 may comprise different numbers of corners 218 which define the outermost drive portions 202. By way of illustration, the configurations of the interface 124 illustrated in FIGS. 29-30 are generally hexagonal and each comprise six corners 218 which define outermost drive portions 202. The interface 124 illustrated in FIG. 31 is generally rectangular and comprises four corners 218 which define outermost drive portions 202. The interface 124 illustrated in FIG. 32 is generally star-shaped and comprises six drive lobes 245, each of which comprises a corner 218 which defines an outermost drive portion 202. In configurations where the interface 124 comprises drive lobes 245 which terminate at corners 218 defined such as by points or apexes, at least two drive lobes 245 may define outermost drive portions 202. However, as noted above, other configurations are contemplated, such as where the interface 124 comprises three drive lobes 245, more than four drive lobes 245, and the like. The interface illustrated in FIG. 33 comprises an irregular shape which comprises a single corner 218 defining an outermost drive portion 202. It will be appreciated that other arrangements and configurations of the corners 218 and/or the outermost drive portions 202 are contemplated.

Referring now to the configuration of the insertion portion 72 of the drill bit 66 depicted schematically in FIG. 29, one of the retention surfaces 224 of the resilient arms 188 and one of the outer drive surfaces 206 of the outermost drive portions 202 of the interface 124 comprise, define, or are otherwise aligned with a common bisecting plane CBP intersecting the axis AX to define two equal portions of the retention surface 224 and the resilient arm 188 and two equal portions of the outer drive surface 206 and the outermost drive portion 202. It will be appreciated that the symmetrical relationship described above is exemplary, and other configurations are contemplated.

Referring now to the configuration of the insertion portion 72 of the drill bit 66 depicted schematically in FIG. 32, one of the retention surfaces 224 of one of the resilient arms 188 and one of drive lobes 245 comprise, define, or are otherwise aligned with a common bisecting plane CBP intersecting the axis AX to define two equal portions of the retention surface 224 of the resilient arm 188 and two equal portions of the outermost drive portion 202 (here, defined by the apexes of the triangular drive lobes 245). Here too, it will be appreciated that the symmetrical relationship described above is exemplary, and other configurations are contemplated.

Referring now to the configuration of the insertion portion 72 of the drill bit 66 depicted schematically in FIG. 31, one of the retention surfaces 224 of the resilient arms 188 comprises, defines, or is otherwise aligned with a first bisecting plane FBP that intersects the axis AX to define two equal portions of the retention surface 224. Furthermore, one of the outermost drive portions 202 of the interface 124 comprises, defines, or is otherwise aligned with a second bisecting plane SBP that intersects the axis AX to define two equal portions of the outermost drive portion 202 (here, defined by the apexes of two of the corners 218 of the rectangular profile). In this configuration, the second bisecting plane SBP is radially spaced approximately 60 degrees from the first bisecting plane FBP about the axis AX. Thus, as noted above, the retention surface 224 of the resilient arm 188 may be radially aligned with the outermost drive portion 202 of the interface 124 at intervals of approximately 60 degrees. Here too, other configurations are contemplated.

Referring now to FIG. 2, in one configuration, the interface 124 has an interface length IL defined between the distal interface end 194 and the proximal interface end 196, and the shank 176 has a shank length SL defined between the distal end 180 and the proximal end 178, with the shank length SL being greater than or equal to three times the interface length IL. However, those having ordinary skill in the art will appreciate that other configurations are contemplated for the drill bit 66, such as with a shank length SL is five or more times the interface length IL. Referring now to FIG. 22, in the illustrated configuration, the retention surface 224 is spaced from the proximal interface end 196 at a retention distance RD that is greater than or equal to the interface length IL. Here too, other configurations are contemplated.

Figure 34:
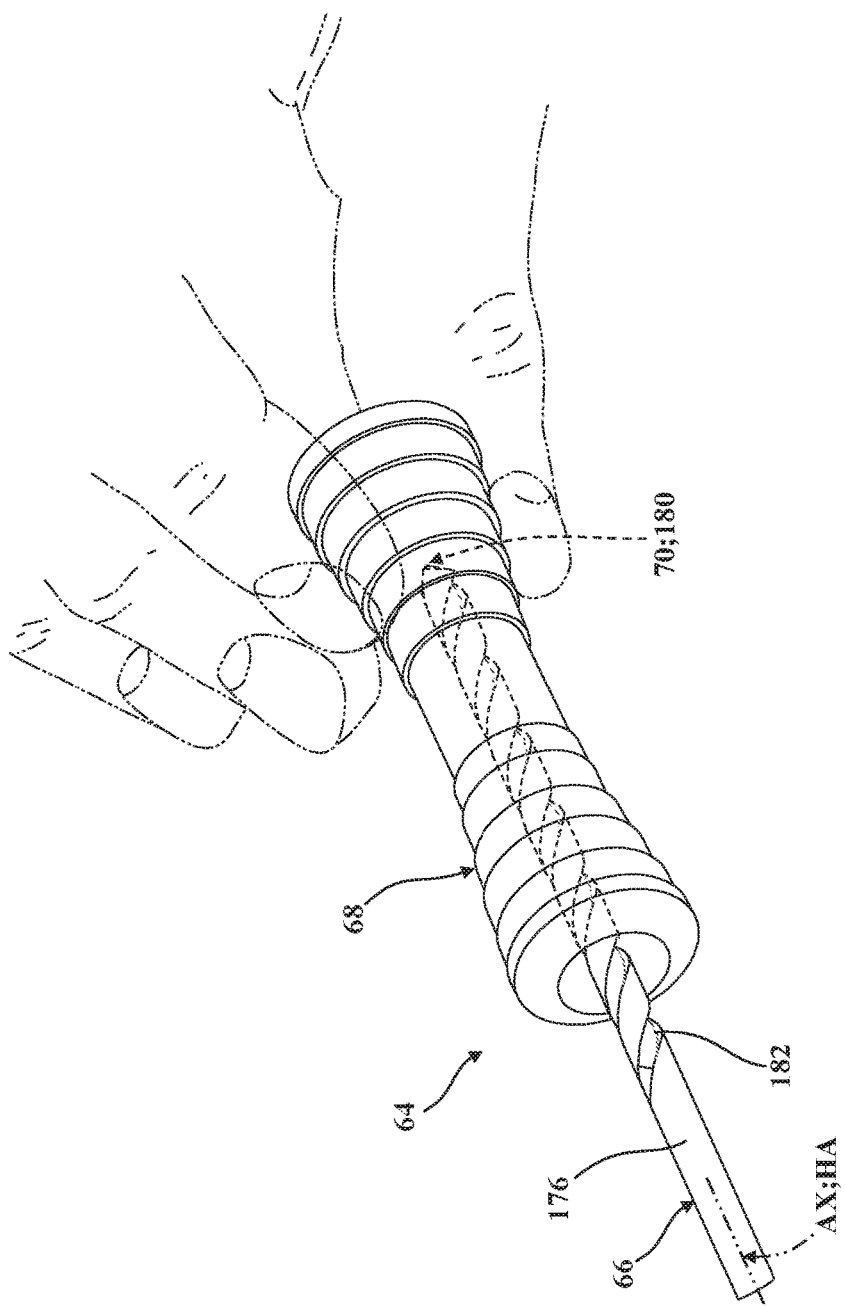
FIG. 34 is a partial perspective view of the end effector assembly of FIGS. 1-2, shown with the distal cutting tip portion of the drill bit disposed within the tip protector.
Figure 35:
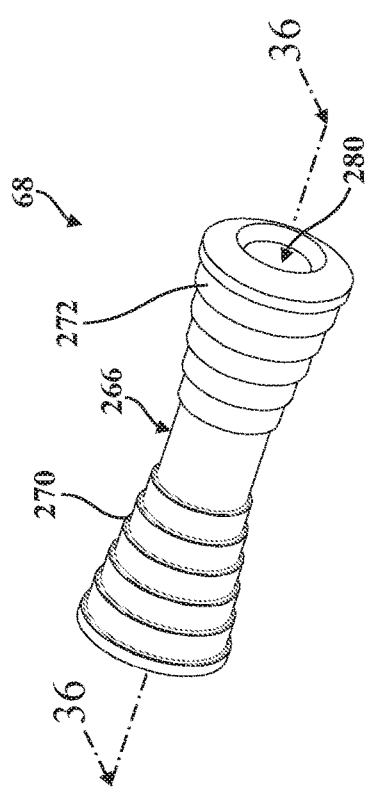
FIG. 35 is a perspective view of the tip protector of the end effector assembly illustrated in FIGS. 1-2 and 34.

Referring now to FIGS. 1-2 and 34, as noted above, in some configurations, the tip protector 68 of the end effector assembly 64 is provided to facilitate releasably attaching the drill bit 66 to the drive assembly 114 of the surgical instrument 62 such that the tip protector 68 at least partially conceals the cutting tip portion 70 of the drill bit 66. Thus, a user can grasp the tip protector 68 and thereby handle the drill bit 66 to facilitate attachment with the surgical instrument 62, without contacting the cutting tip portion 70, before subsequently removing the tip protector 68 from the cutting tip portion 70. To this end, as shown in FIG. 36, the tip protector 68 generally comprises a handle 266 configured to be grasped by the user, and a receptacle 268 capable of receiving the cutting tip portion 70 of the drill bit 66.

Figure 36:
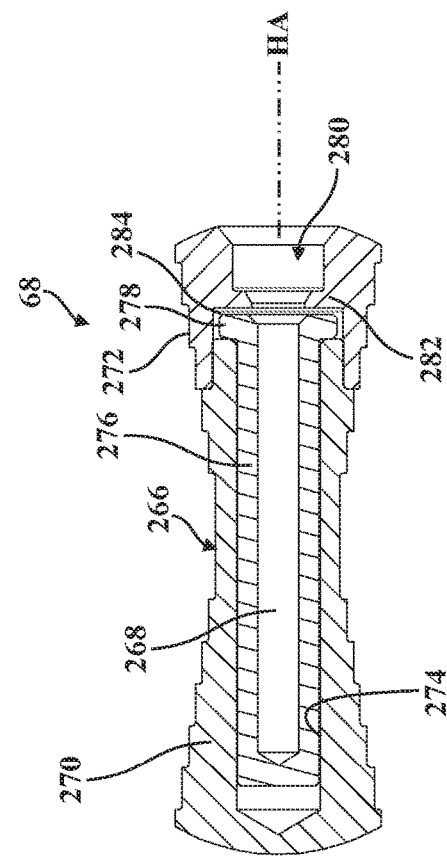
FIG. 36 is a sectional view taken along line 36-36 in FIG. 35.
Figure 37:
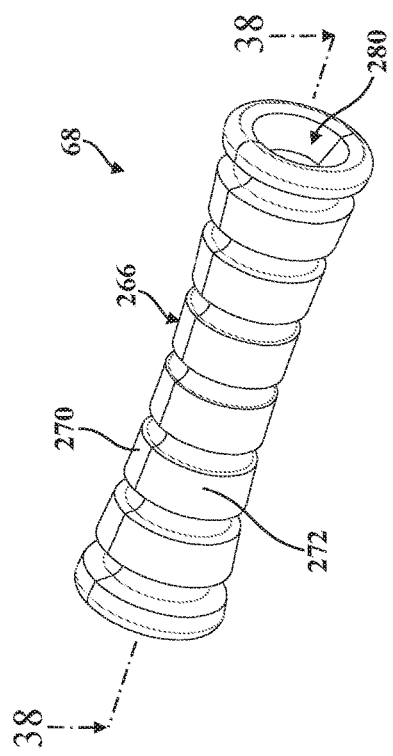
FIG. 37 is a perspective view of another tip protector configuration of the end effector assembly.
Figure 38:
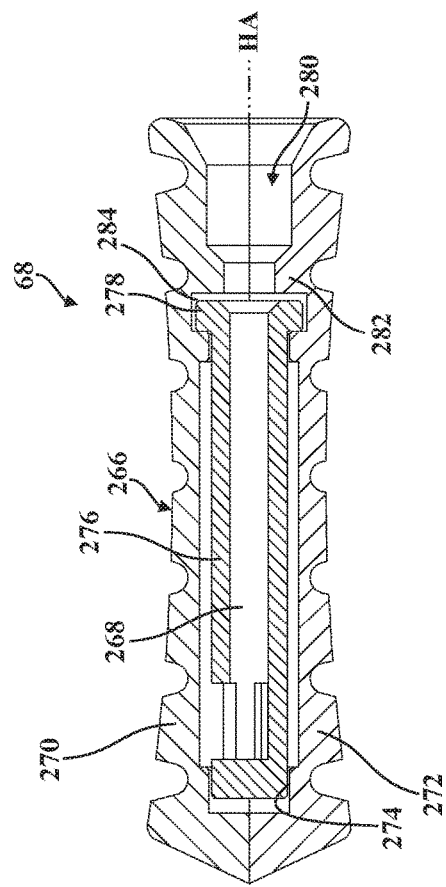
FIG. 38 is a sectional view taken along line 38-38 in FIG. 37.

In the configuration of the tip protector 68 illustrated in FIGS. 1-2 and 34-36, and as is best depicted in FIG. 36, the handle 266 comprises a first handle body 270 and a second handle body 272 which are operatively attached together axially, such as via a press-fit engagement. The first handle body 270 defines a handle bore 274 extending along a handle axis HA. A receiver 276 is rotatably supported within the handle bore 274 and comprises the receptacle 268 which is capable of receiving the cutting tip portion 70 of the drill bit 66, such as via a friction-fit engagement. In this configuration, the receiver 276 comprises a flange 278 which abuts a portion of the first handle body 270 adjacent to the second handle body 272. The second handle body 272 comprises an inlet mouth 280 which tapers inwardly to a stepped region 282 which, in turn, is disposed adjacent to the flange 278 of the receiver 276 to define a recess 284 between the first handle body 270 and the stepped region 282. The flange 278 is disposed within the recess 284 such that the receiver 276 constrained form translating along the handle axis HA and out of the handle bore 274. Thus, the receiver 276 is able to rotate about the handle axis HA within the handle bore 274 without rotating the handle 266.

When the cutting tip portion 70 is disposed within the receptacle 268, the drill bit 66 effectively rotates concurrently with the receiver 276 about the handle axis HA. Here, the user can grasp the handle 266 and attach the drill bit 66 to the surgical instrument 62 without contacting the cutting tip portion 70. Moreover, the relative rotation afforded between the handle 266 and the drill bit 66 in this configuration compliments the "self-aligning" features of drill bit 66 described above in connection with FIGS. 24A-24B. Specifically, the indexing of the interface 124 relative to the bore 122 via the aligning element 242 can occur without translating rotation back to the handle 266 in this configuration, which promotes attachment of the drill bit 66 to the surgical instrument 62 in an efficient manner.

As noted above, the tip protector 68 can be configured in a number of different ways to promote handling of the drill bit 66. For example, in the configuration of the tip protector 68 depicted in FIGS. 37-38, the first handle body 270 and the second handle body 272 of the handle 266 are operatively attached together laterally, such as via interlocking features, adhesion, bonding, and the like. In this configuration, the recess 284 is likewise provided to accommodate the flange 278 so as to restrict axial movement of the receiver 276 relative to the handle 266, and the receptacle 268 is similarly configured to releasably secure to the cutting tip portion 70 of the drill bit, such as by frictional engagement.

Figure 39:
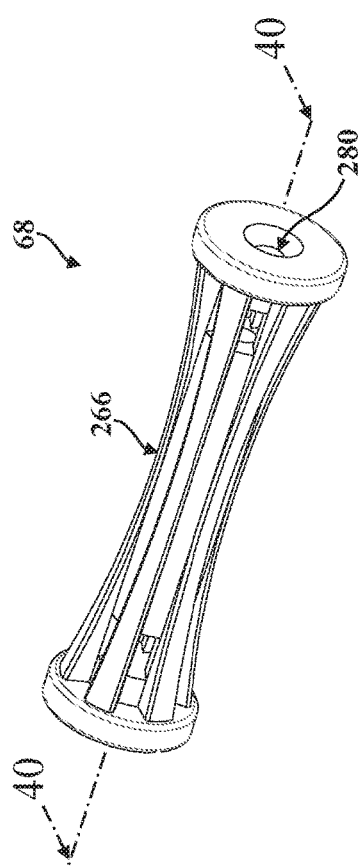
FIG. 39 is a perspective view of another tip protector configuration of the end effector assembly.
Figure 40:
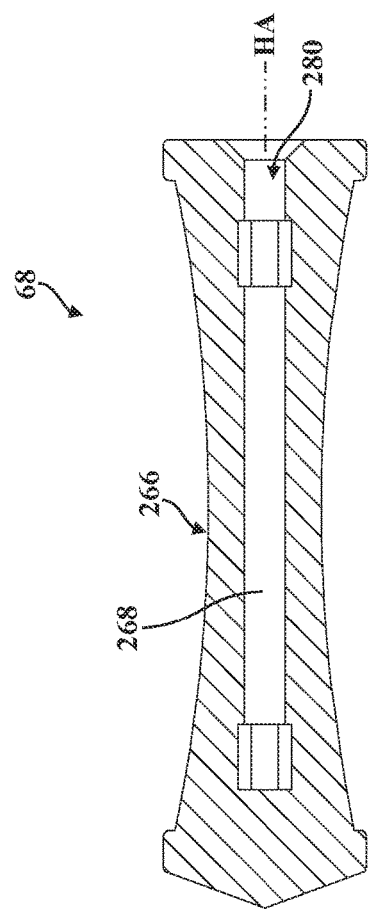
FIG. 40 is a sectional view taken along line 40-40 in FIG. 39.

The configuration of the tip protector 68 depicted in FIGS. 39-40 is realized as a unitary, one-piece component such that the handle 266 defines the receptacle 268, which may be utilized in connection with configurations where relative rotation between the handle 266 and the drill bit 66 is undesirable or unnecessary. In some configurations, such as those comprising single-piece tip protectors 68, at least a portion of the tip protector 68 may be resiliently deformable, may be tapered or stepped to accommodate cutting tip portions 70 of different sizes, and the like. It will be appreciated that these features could also be utilized in connection with other types of tip protectors 68 illustrated herein.

Figure 41:
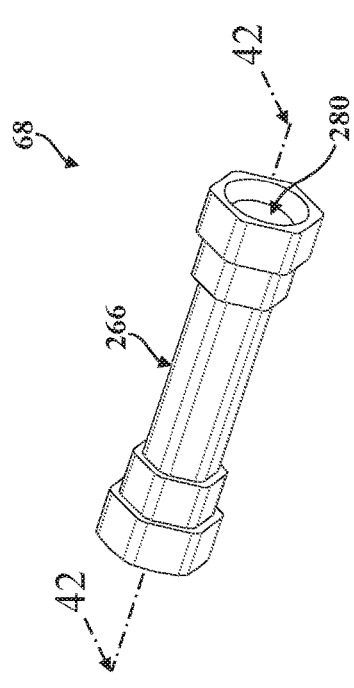
FIG. 41 is a perspective view of another tip protector configuration of the end effector assembly.
Figure 42:
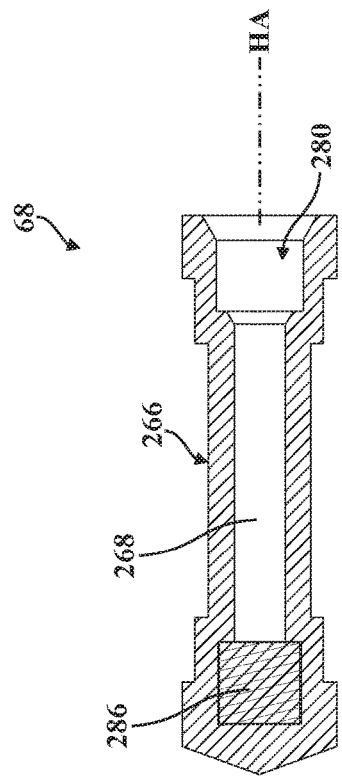
FIG. 42 is a sectional view taken along line 42-42 in FIG. 41.

The configuration of the tip protector 68 depicted in FIGS. 41-42 employs a unitary, one-piece handle 266 in which a magnet 286 is disposed. Here, the receptacle 268 is likewise defined by the handle 266, and extends along the handle axis HA between the magnet 286 and the inlet mouth 280. Where the drill bit 66 is manufactured from a ferromagnetic material, the magnet 286 will attract the cutting tip portion 70 to promote releasable retention between the tip protector 68 and the drill bit 66. Here, it will be appreciated that the receptacle 268 may be sized so as to permit a looser fit with the drill bit 66 and thereby facilitate relative rotation between the drill bit 66 and the handle 266 while axially retaining the drill bit 66 via the magnet 286. In some configurations, such as where the magnet 286 is relatively strong, the receptacle 268 may be sized to receive cutting tip portions 70 of various sizes, diameters, and the like.

Figure 43:
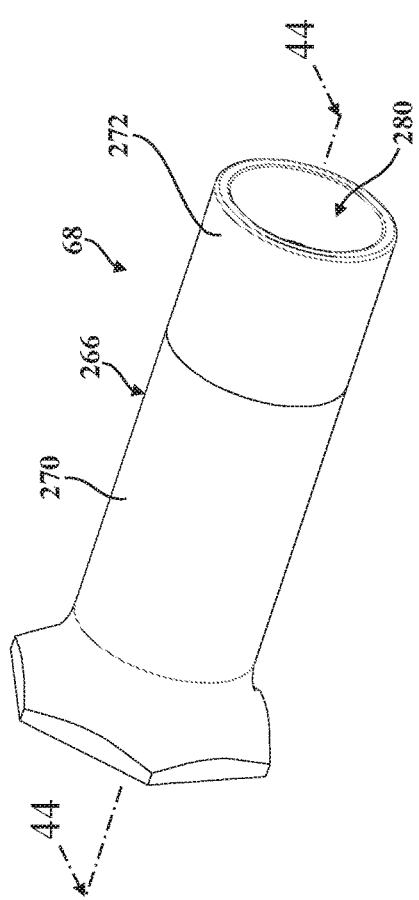
FIG. 43 is a perspective view of another tip protector configuration of the end effector assembly.
Figure 44:
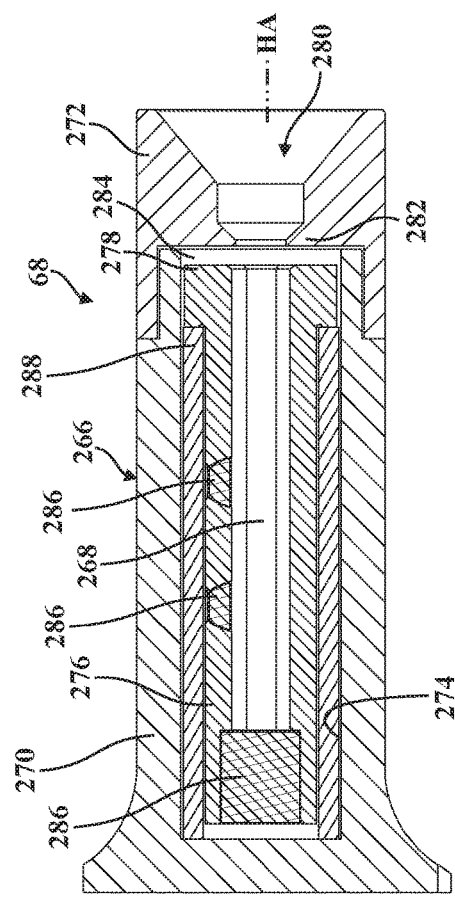
FIG. 44 is a sectional view taken along line 44-44 in FIG. 43.

The configuration of the tip protector 68 depicted in FIGS. 43-44 employs a handle 266 which is configured similarly to the configuration of the tip protector 68 described above in connection with FIGS. 35-36. In this configuration, however, a sleeve 288 is supported in the first handle body 270. Here, the sleeve 288 rotatably supports the receiver 276 and cooperates with the second handle body 272 to define the recess 284 in which the flange 278 is disposed. Similar to the configuration of the tip protector 68 described above in connection with FIGS. 41-42, magnets 286 are likewise employed to help retain the cutting tip portion 70 of the drill bit 66. In this configuration, however, magnets 286 are also disposed radially about the handle axis HA to provide further magnetic attraction to the drill bit 66 and, in some configurations, to facilitate retaining cutting tip portions 70 of various sizes, diameters, and the like. By way of illustrative example, a cutting tip portion 70 with a diameter that is smaller than the receptacle 268 of the receiver 276 may be retained both axially and laterally by this arrangement of magnets 286.

Figure 45:
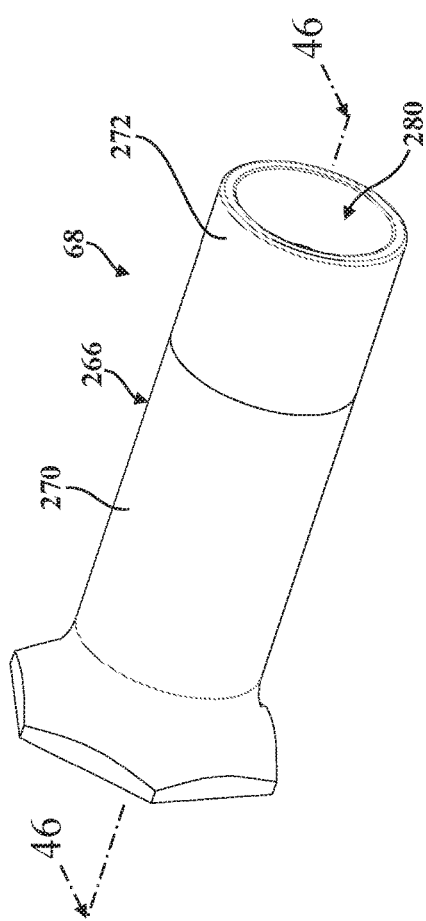
FIG. 45 is a perspective view of another tip protector configuration of the end effector assembly.
Figure 46:
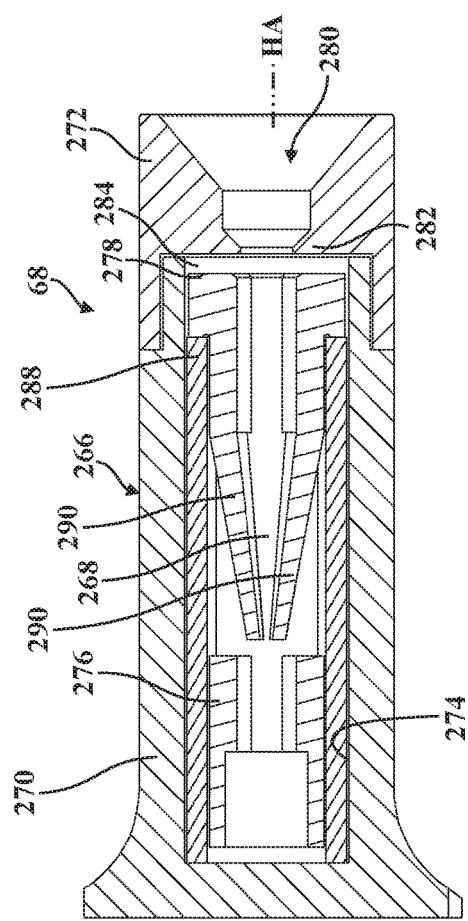
FIG. 46 is a sectional view taken along line 46-46 in FIG. 45.

The configuration of the tip protector 68 depicted in FIGS. 45-46 employs a handle 266, a first handle body 270, a second handle body 272, and a sleeve 288 which are similar to the configuration of the tip protector 68 described above in connection with FIGS. 43-44. However, in this configuration, the receiver 276 comprises one or more resilient tabs 290 which extend inwardly toward the handle axis HA. Here, when the cutting tip portion 70 is inserted into the receptacle 268, the resilient tabs 290 contact and exert force on the cutting tip portion 70. Thus, it will be appreciated that this configuration of the tip protector 68 can likewise be employed to releasably attach to cutting tip portions 70 of various sizes, diameters, and the like.

Figure 7A:
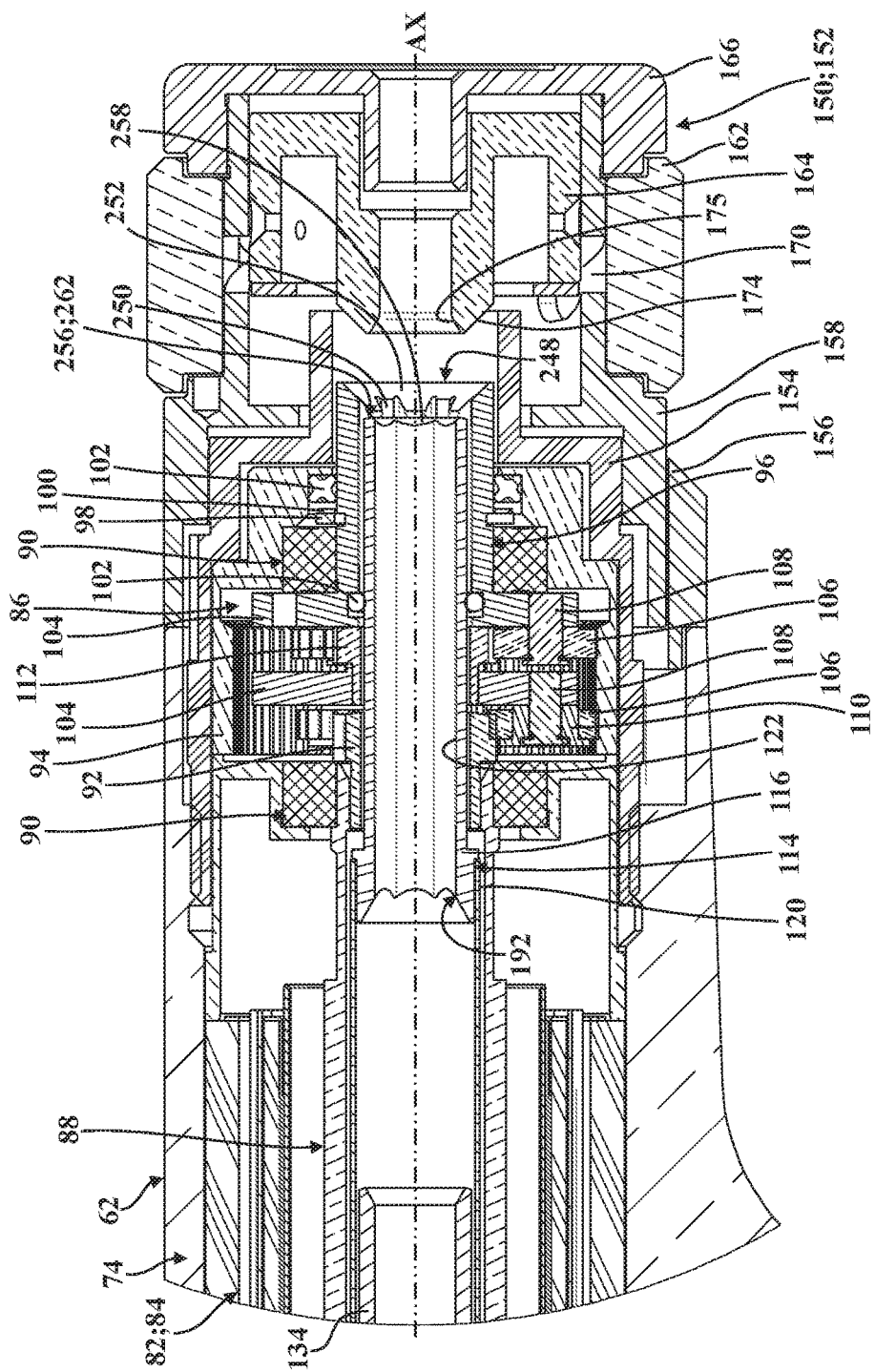
FIG. 7A is an enlarged detail view taken at indicia 7 in FIG. 6, shown depicting portions of the measurement module, the drive assembly, the release mechanism, and the actuator assembly within the handpiece body.
Figure 7B:
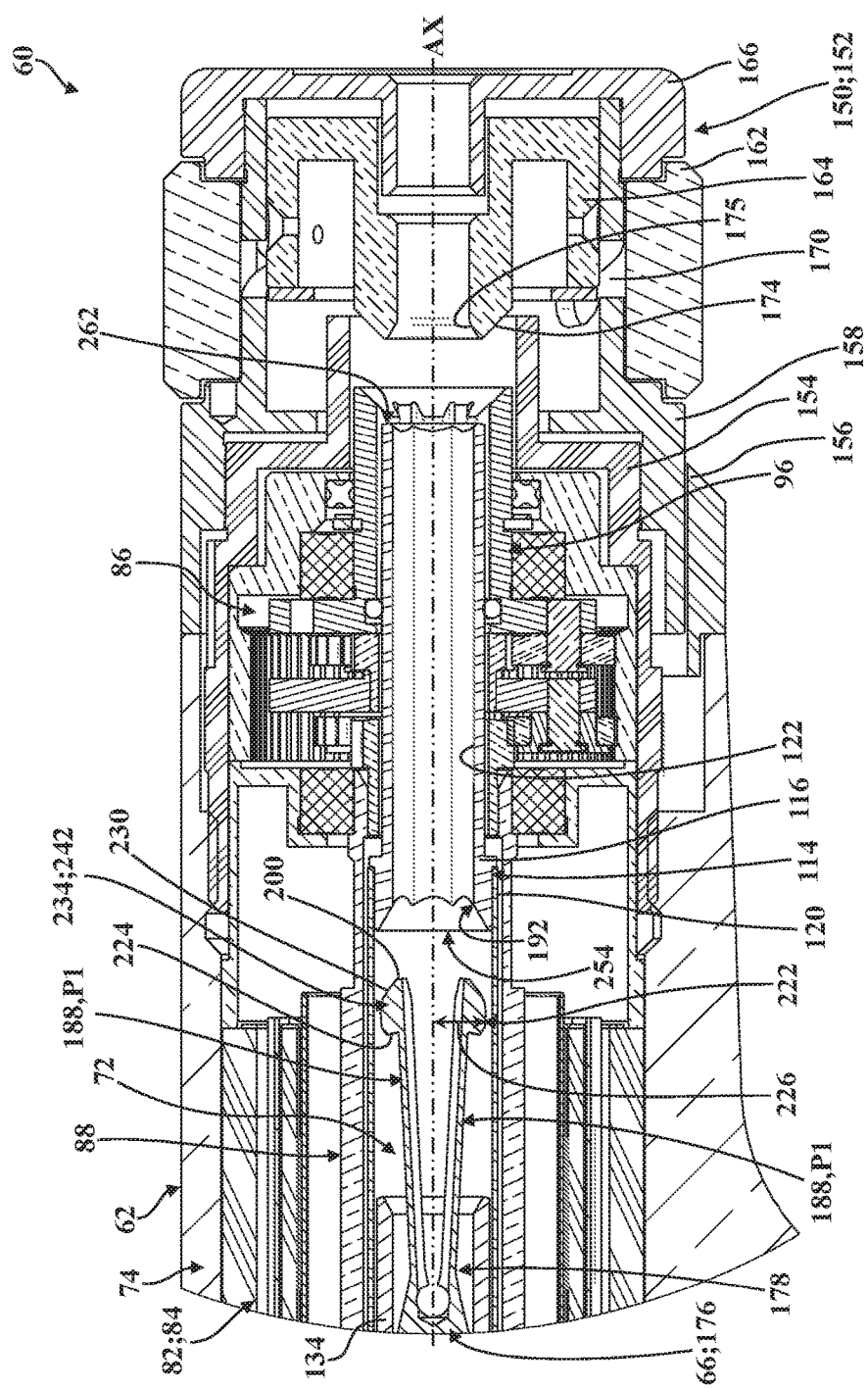
FIG. 7B is another enlarged detail view of the surgical system of FIGS. 1 and 7A, shown with a pair of resilient arms arranged at a proximal end of the drill bit approaching a driving cannula of the drive assembly.
Figure 7C:
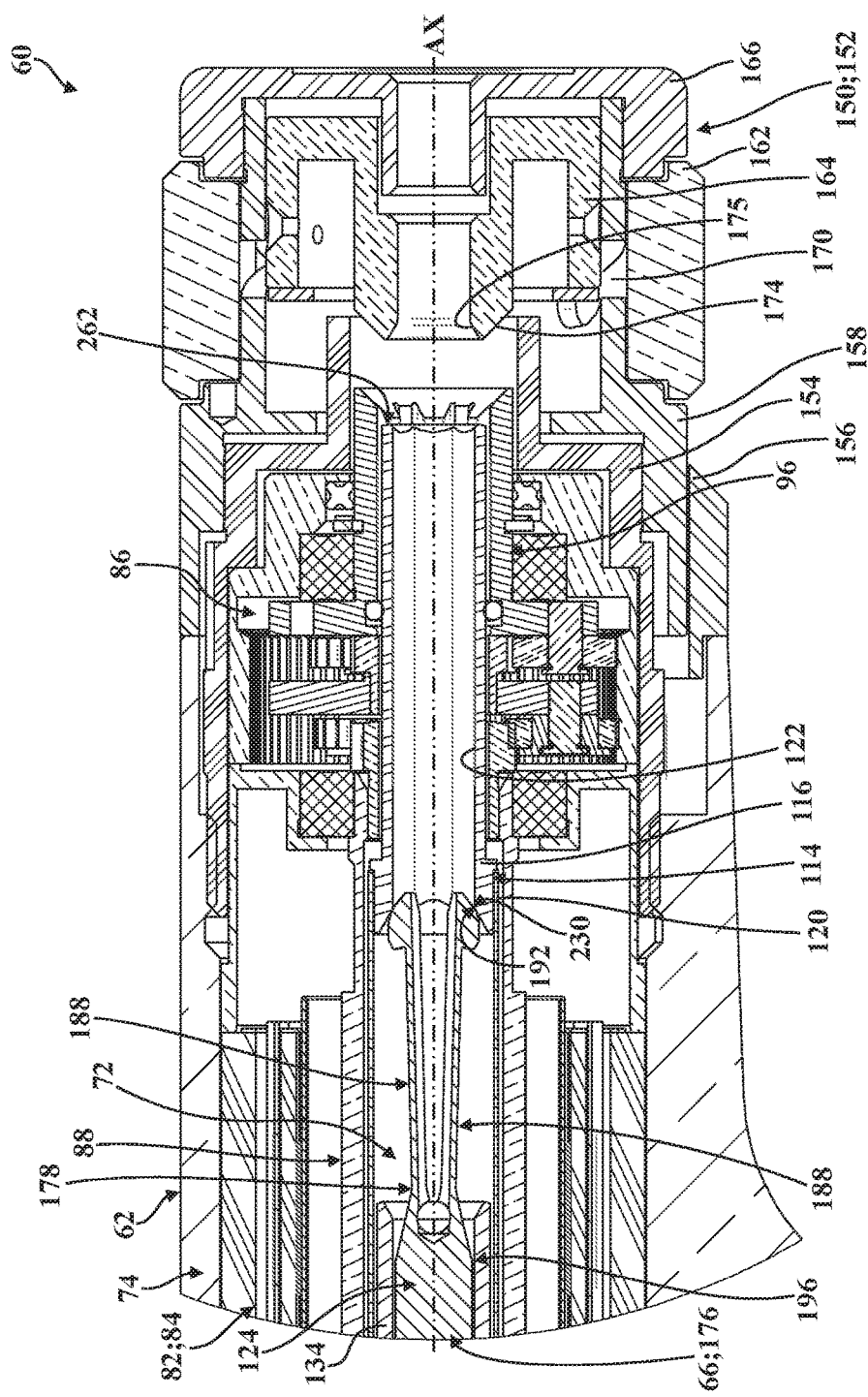
FIG. 7C is another enlarged detail view of the surgical system of FIGS. 7A-7B, shown with the resilient arms of the drill bit engaging against a seat surface of the driving cannula and deflecting towards each other.
Figure 7D:
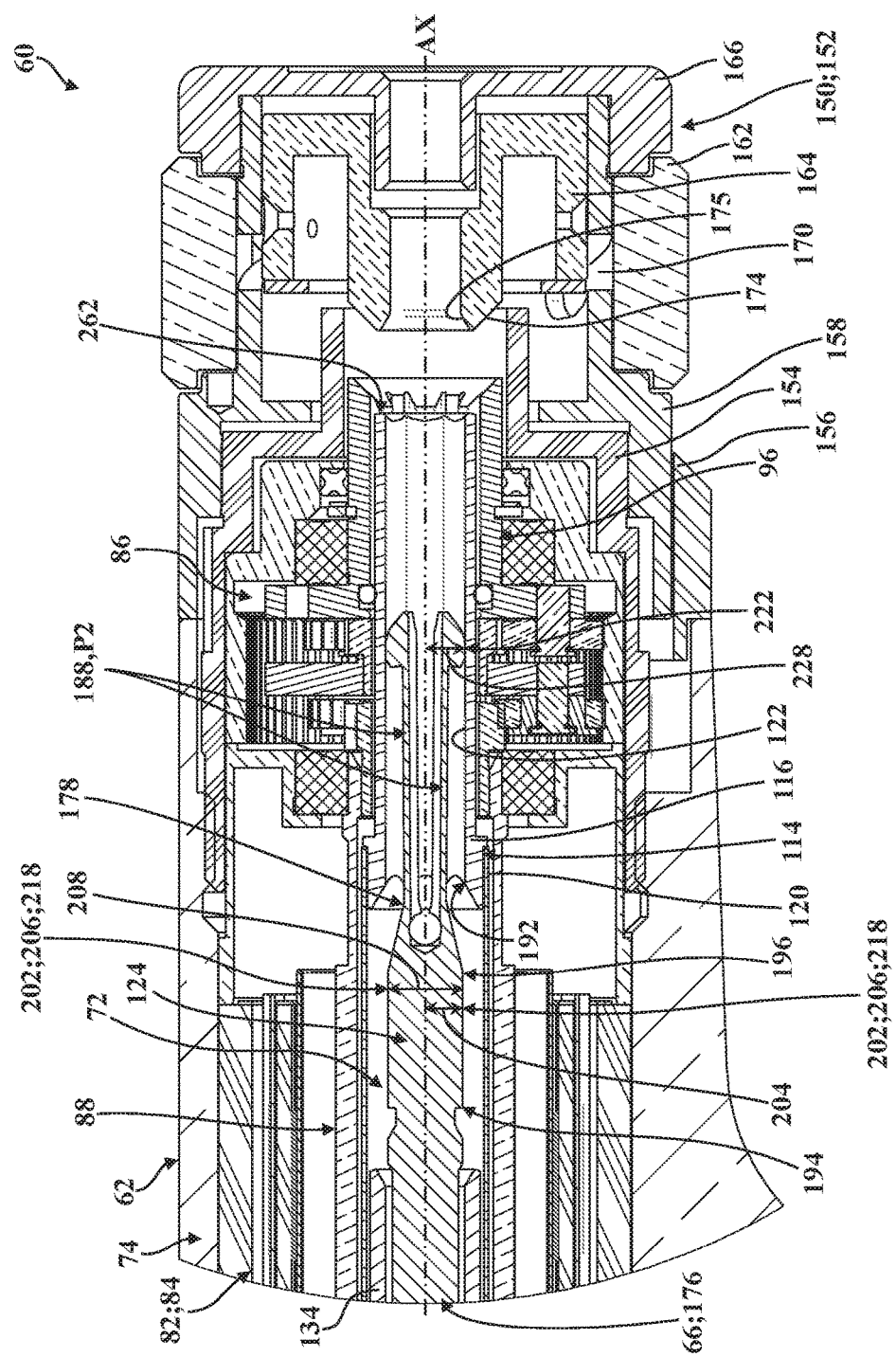
FIG. 7D is another enlarged detail view of the surgical system of FIGS. 7A-7C, shown with the resilient arms of the drill bit disposed within a bore of the driving cannula, the drill bit shown having a shank with a proximal end from which the resilient arms extend, a stop coupled to the shank, and an interface coupled to the shank and interposed between the stop and the proximal end.
Figure 7E:
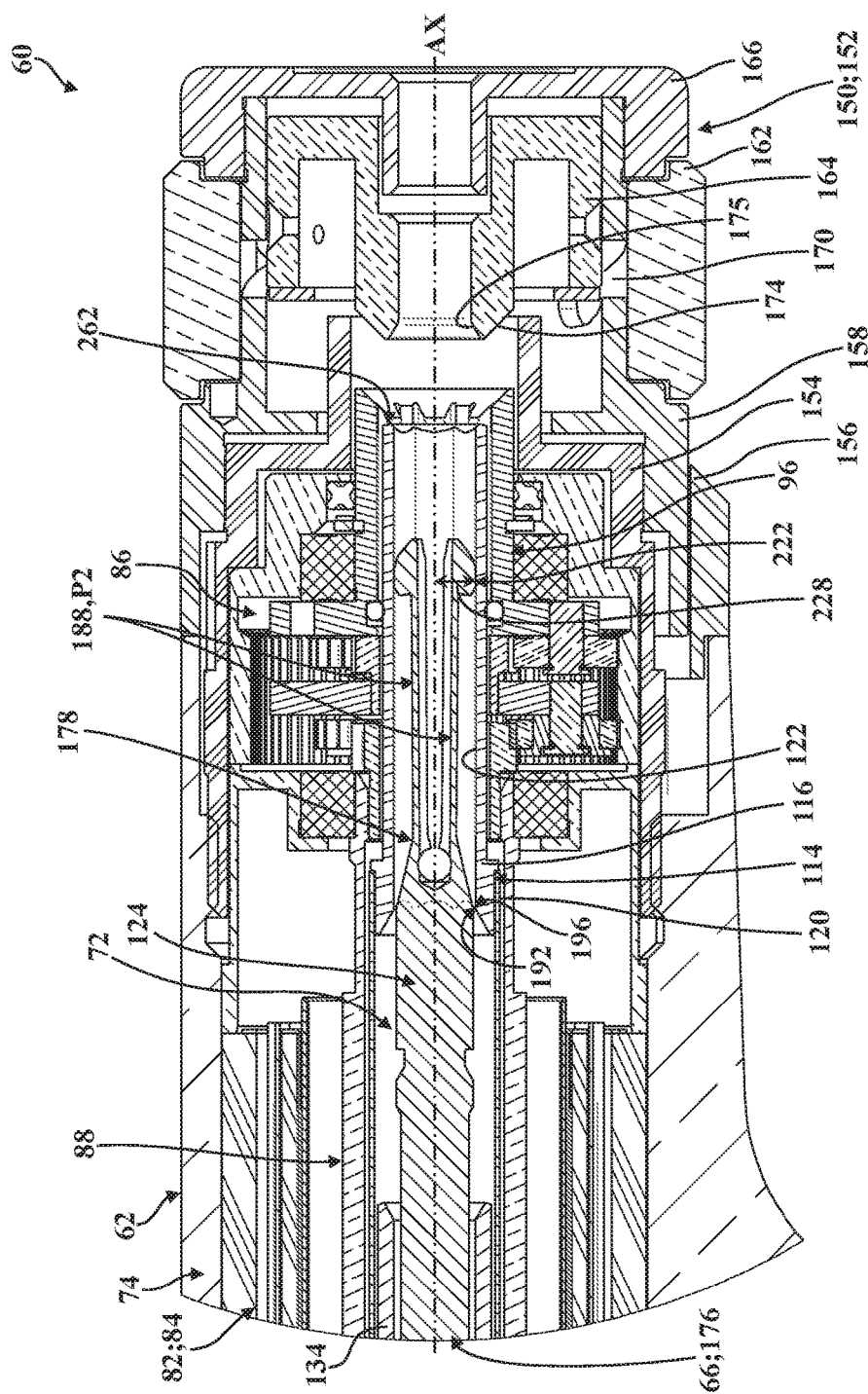
FIG. 7E is another enlarged detail view of the surgical system of FIGS. 7A-7D, shown with the resilient arms of the drill bit disposed further within the bore of the driving cannula, and with the interface of the drill bit positioned within the bore of the driving cannula adjacent to the seat surface.
Figure 7F:
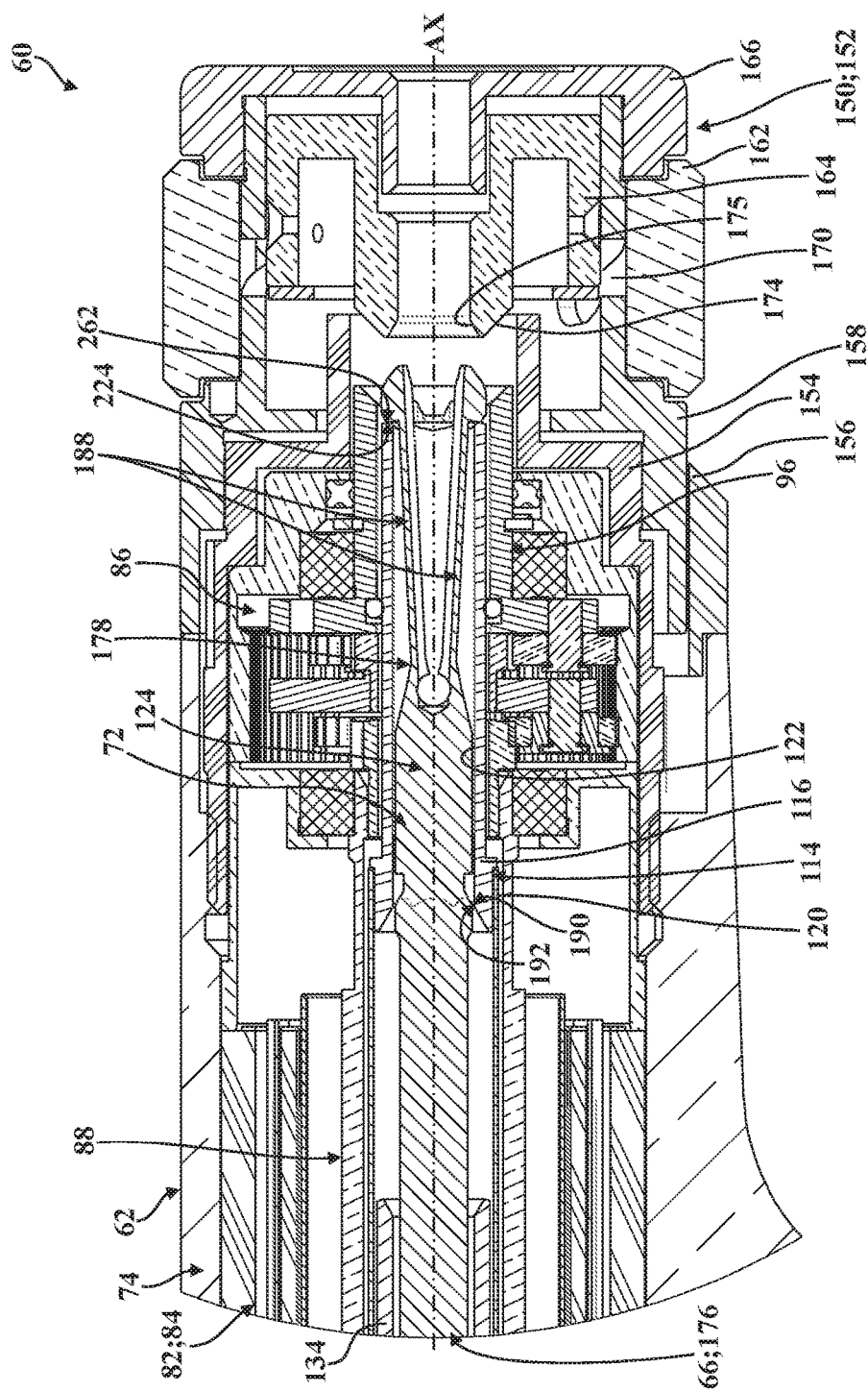
FIG. 7F is another enlarged detail view of the surgical system of FIGS. 7A-7E, shown with the resilient arms of the drill bit deflected resiliently away from one another with each resilient arm having a retention surface abutting a lock surface of the driving cannula, and shown with the stop of the drill bit abutting the seat surface of the driving cannula to retain the interface within the bore.

FIGS. 7A-7I sequentially illustrate certain steps involved with attaching the drill bit 66 to the surgical instrument 22 and then releasing the drill bit 66 from the surgical instrument 66. FIG. 7A depicts various portions of the surgical instrument 62 with the drill bit 66 completely removed.

In FIG. 7B, the insertion portion 72 of the drill bit 66 is shown partially inserted into the surgical instrument 62. While not depicted in this view, it will be appreciated that inserting the drill bit 66 may advantageously be performed with the tip protector 68 removably attached to the cutting tip portion 70, such as to permit relative rotation between the drill bit 66 and the handle 266 as described above. Here in FIG. 7B, the resilient arms 188 are shown extending away from the proximal end 178 of the shank 176 such that the arm ends 200 are disposed axially between the measurement cannula 134 and the distal driving cannula end 254 of the driving cannula 116. The resilient arms 188 are shown arranged in the first position P1.

In FIG. 7C, the drill bit 66 is advanced further into the surgical instrument 62 (compare with FIG. 7B). Here, the ramp surfaces 230 of the resilient arms 188 are shown abutting against the seat surface 192 of the driving cannula 116, deflecting toward the axis AX.

In FIG. 7D, the drill bit 66 is advanced even further into the surgical instrument 62 (compare with FIG. 7C). Here, the outer arm surfaces 222 of the resilient arms 188 are shown in contact with the bore 122 of the driving cannula 116 which, as will be appreciated from the previous description of the aligning element 242, means that the interface 124 of the drill bit 66 is indexed relative to the bore 122 of the driving cannula 116 without any engagement, contact, or abutment occurring between the interface 124 and the bore 122. Furthermore, the resilient arms 188 are shown arranged in the second position P2 in FIG. 7D.

In FIG. 7E, the drill bit 66 is advanced still further into the surgical instrument 62 (compare with FIG. 7D). Here, the proximal interface end 196 of the interface 124 has entered the bore 122 of the driving cannula 116. Here too in FIG. 7E, the resilient arms 188 are shown arranged in the second position P2.

In FIG. 7F, the drill bit 66 is advanced fully into the surgical instrument 62 (compare with FIG. 7E). Here, the resilient arms 188 are shown deflected back away from the axis AX, away from the second position P2 toward (or, in some configurations, at) the first position P1. As noted above, this brings the retention surfaces 224 of the resilient arms 188 into abutment with the lock surfaces 262 provided at the proximal driving cannula end 256, which prevents the drill bit 66 from moving distally along the axis AX. Moreover, abutment between the stop surface 190 of the drill bit 66 and the seat surface 192 of the driving cannula 116 prevents the drill bit 66 from advancing axially further into the surgical instrument 62. Thus, the drill bit 66 is axially locked to the driving cannula 116 in FIG. 7F. Furthermore, because the interface 124 of the drill bit 66 is disposed within the bore 122 of the driving cannula 116, the drill bit 66 is also rotationally locked to the driving cannula 116. As such, when in the orientation depicted in FIG. 7F, the surgical instrument 62 can be utilized to rotate the drill bit 66.

Figure 7G:
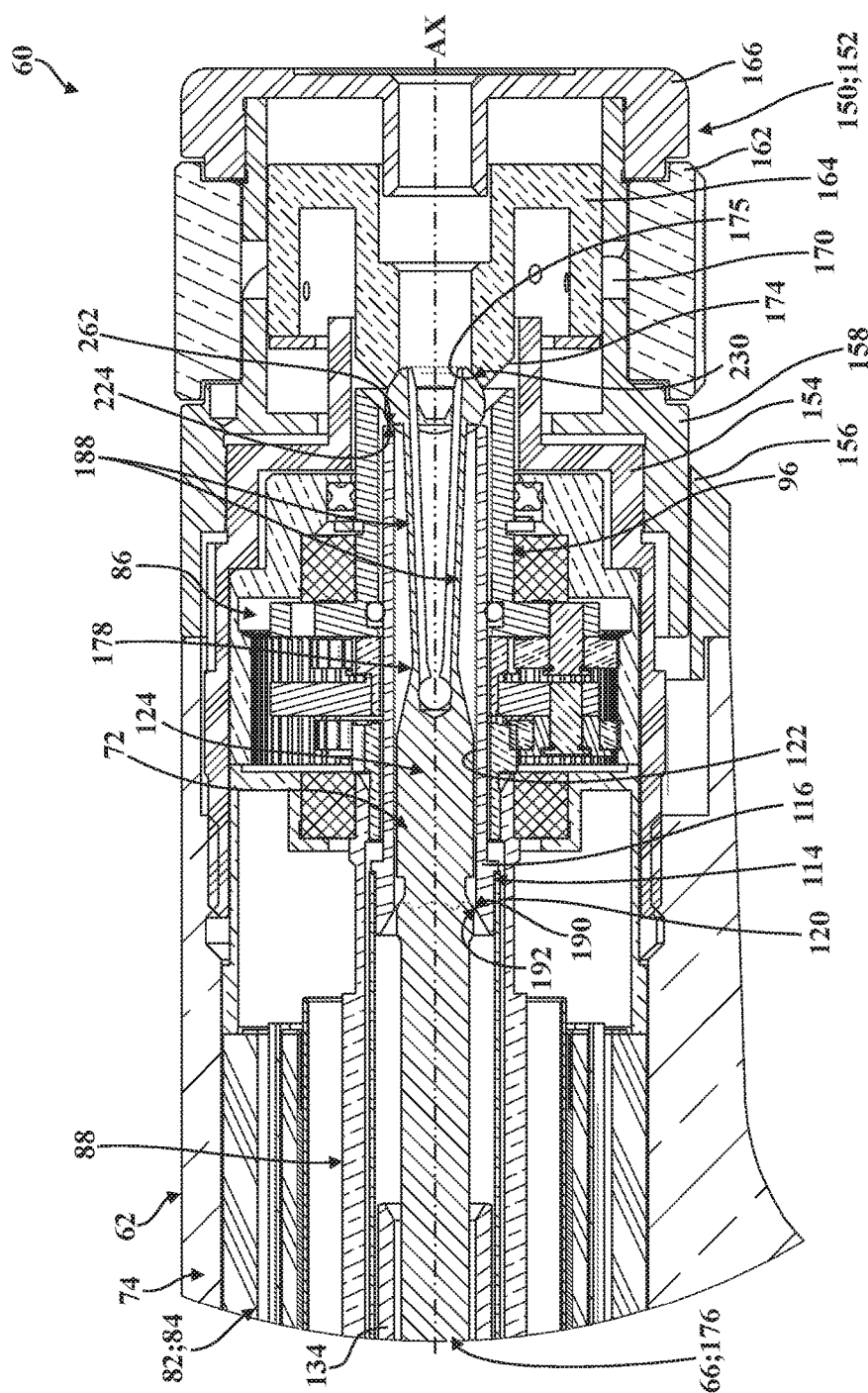
FIG. 7G is another enlarged detail view of the surgical system of FIGS. 7A-7F, shown with a slide element of the release mechanism engaging against the resilient arms and deflecting the resilient arms toward one another to facilitate moving the retention surfaces of the resilient arms out of abutment with the lock surfaces of the driving cannula.

In FIG. 7G, the drill bit 66 is disposed in the same axial position as is illustrated in FIG. 7F, but the resilient arms 188 are shown deflecting back toward the axis AX to facilitate removing the drill bit 66 from the surgical instrument 62 via actuation of the release mechanism 150 (compare with FIG. 7F). More specifically, in FIG. 7G, rotation of the collar 162 of the release mechanism 150 has resulted in axial translation of the slide element 164 to bring the tapered inner surface 175 of the actuating element 174 into abutment with the ramp surfaces 230 of the resilient arms 188, thereby deflecting the resilient arms 188 back toward the axis AX.

Figure 7H:
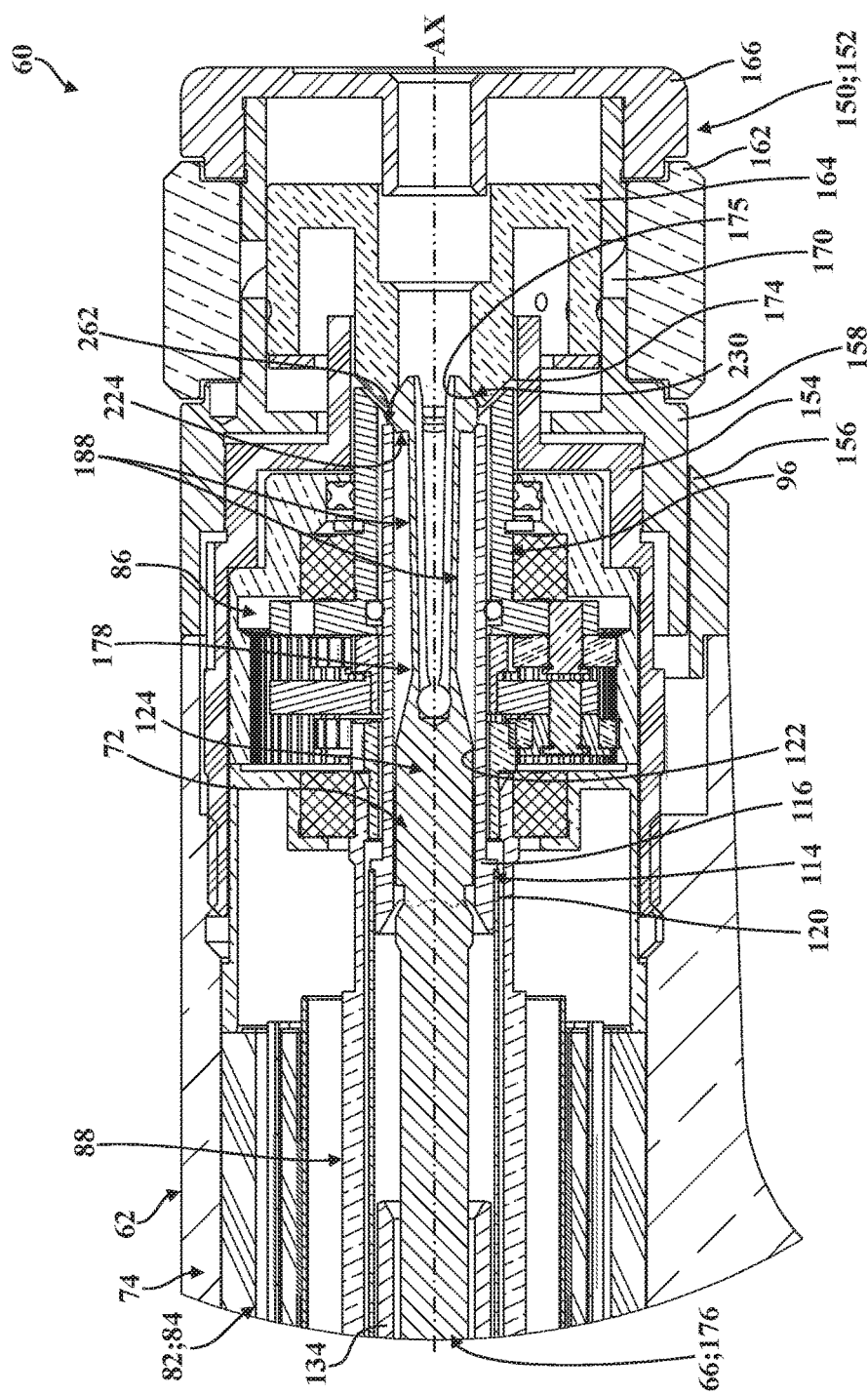
FIG. 7H is another enlarged detail view of the surgical system of FIGS. 7A-7G, shown with the slide element of the release mechanism further engaging against and deflecting the resilient arms with the retention surfaces out of abutment with the lock surfaces of the driving cannula.

In FIG. 7H, the drill bit 66 is still disposed in the same axial position as illustrated in FIGS. 7E-7F, but the resilient arms 188 are shown deflected even further back toward the axis AX (compare with FIG. 7G). Here in FIG. 7H, further rotation of the collar 162 of the release mechanism 150 has resulted in additional axial translation of the slide element 164, thereby causing the resilient arms 188 to deflect even further back toward the axis AX to bring the retention surfaces 224 of the resilient arms 188 back out of abutment with the lock surfaces 262 provided at the proximal driving cannula end 256 to facilitate removing the drill bit 66 from the surgical instrument 62.

Figure 7I:
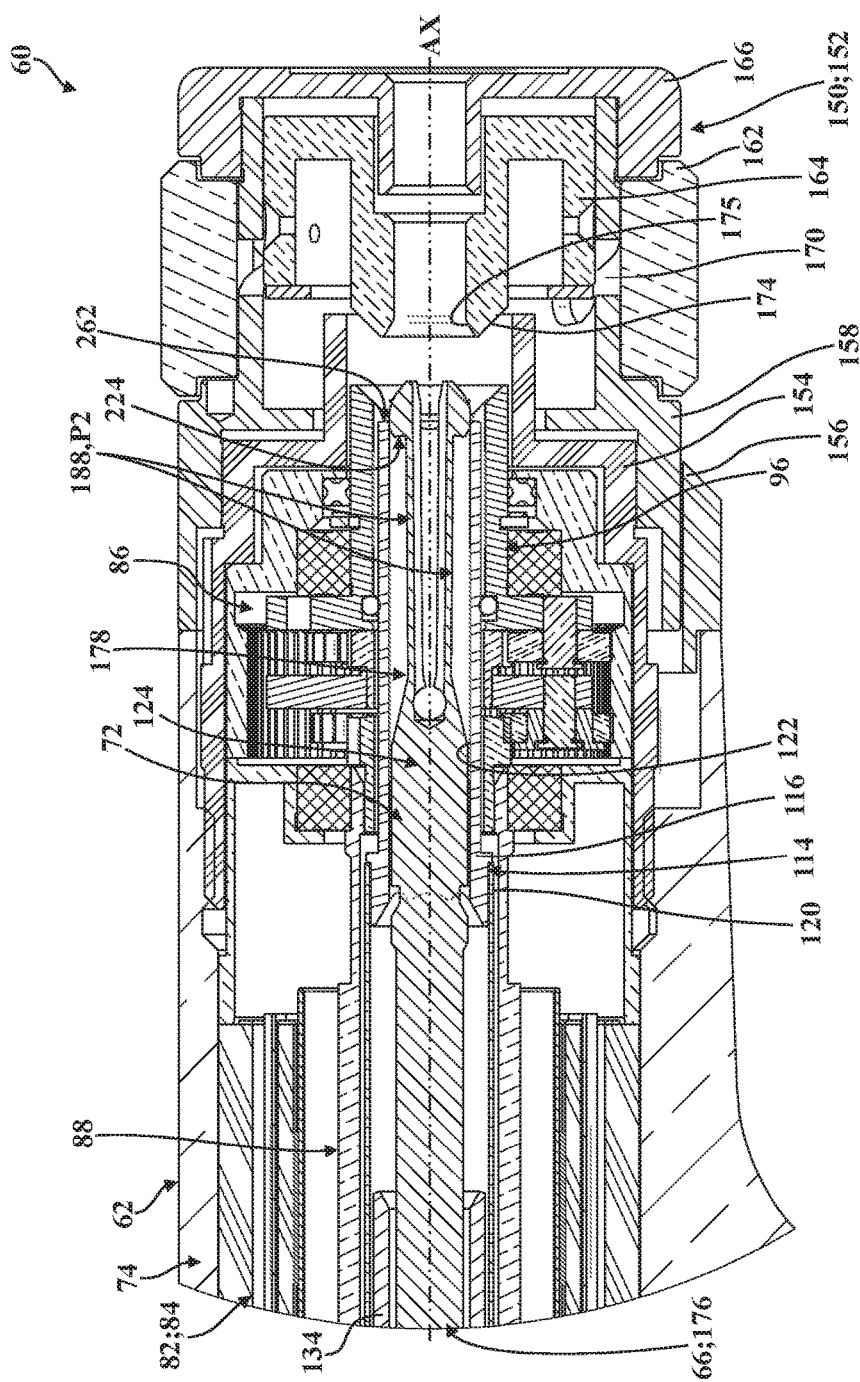
FIG. 7I is another enlarged detail view of the surgical system of FIGS. 7A-7H, shown with the slide element of the release mechanism out of engagement with the resilient arms, and shown with the resilient arms disposed within the bore of the driving cannula adjacent to and out of contact with the lock surfaces.

In FIG. 7I, the drill bit 66 is retracted axially after having been released via the release mechanism 150 (compare with FIG. 7H). Here in FIG. 7I, the resilient arms 188 are shown arranged in the second position P2 and are disposed adjacent to the proximal driving cannula end 256. Here, because the retention surfaces 224 of the resilient arms 188 are out of abutment with the lock surfaces 262 of the driving cannula 115, the drill bit 66 can be removed from the surgical instrument 62.

In this way, the end effector assembly 64 described herein and illustrated throughout the drawings affords significant advantages in connection with facilitating releasable attachment to surgical instruments 62. Specifically, it will be appreciated that the drill bit 66 of the present disclosure can be reliably attached to the surgical instrument 62 in a simple, efficient manner by guiding the insertion portion 72 into the driving cannula 116 and then applying force along the axis AX. Moreover, it will be appreciated that the tip protector 68 described herein affords additional advantages when used in connection with the drill bit 66 by allowing the user to safely handle and position the drill bit 66 while guiding the insertion portion 72 into the driving cannula 116 and applying force along the axis AX. Furthermore, the self-aligning features of the end effector assembly 64 described herein, including without limitation the aligning element 242 of the resilient arms 188 and the relative rotation afforded between the drill bit 66 and the handle 266 of the tip protector 68, further promote improved user experience and efficient, reliable attachment to the surgical instrument.

It will be further appreciated that the terms "include," "includes," and "including" have the same meaning as the terms "comprise," "comprises," and "comprising." Moreover, it will be appreciated that terms such as "first,"

"second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject-matter of a claim dependent from one independent claim can also be implemented in connection with another independent claim.

The present disclosure also comprises the following clauses, with specific features laid out in dependent clauses, that may specifically be implemented as described in greater detail with reference to the configurations and drawings above.

I. A drill bit for releasably attaching to a drive assembly of a surgical instrument, the drill bit comprising:
a shank extending along an axis between a proximal end and a distal end;
a cutting tip portion adjacent to the distal end of the shank;
an interface arranged between the proximal end and the distal end, the interface comprising an outermost drive portion spaced from the axis at a first interface distance, the outermost drive portion comprising an outer drive surface facing away from the axis;
a resilient arm extending from the proximal end of the shank to an arm end, the resilient arm comprising an outer arm surface facing away from the axis, the resilient arm being movable relative to the axis between:
 a first position where the outer arm surface is spaced from the axis at a first arm distance greater than the first interface distance, and
 a second position where the outer arm surface is spaced from the axis at a second arm distance less than the first arm distance.

II. The drill bit as set forth in clause I, wherein the second arm distance is less than or equal to the first interface distance.

III. The drill bit as set forth in any one of clauses I-II, wherein the outer arm surface of the resilient arm and the outer drive surface of the outermost drive portion of the interface are each separately spaced from the axis at substantially the same distance when the resilient arm is in the second position.

IV. The drill bit as set forth in any one of clauses I-III, wherein the interface has a generally polygonal profile.

V. The drill bit as set forth in clause IV, wherein the interface has a rounded hexagonal profile.

VI. The drill bit as set forth in any one of clauses I-V, wherein the resilient arm further comprises an aligning element at the arm end configured to promote at least partial rotation of the drill bit about the axis as the resilient arm moves from the first position to the second position.

VII. The drill bit as set forth in clause VI, wherein the aligning element of the resilient arm at least partially comprises the outer arm surface.

VIII. The drill bit as set forth in any one of clauses VI-VII, wherein the aligning element of the resilient arm comprises a pair of planar arm surfaces adjacent to the outer arm surface;
wherein the interface comprises a pair of planar surfaces; and
wherein one of the planar arm surfaces is generally coplanar with one of the planar surfaces when the resilient arm is in the second position.

IX. An end effector assembly for releasably attaching to a drive assembly of a surgical instrument, the end effector assembly comprising:
a drill bit extending along an axis between a cutting tip portion and an insertion portion; and
a tip protector comprising a handle with a handle bore extending along a handle axis, and
a receiver rotatably supported within the handle bore and constrained from translating along the handle axis relative to the handle, the receiver defining a receptacle capable of receiving the cutting tip portion of the drill bit;
wherein the handle is adapted to be gripped by a user to facilitate attaching the drill bit to the surgical instrument such that the drill bit and the receiver rotate concurrently relative to the handle.

X. The end effector assembly as set forth in clause IX, wherein the insertion portion of the drill bit comprises:
a shank extending along the axis between a proximal end and a distal end, with the cutting tip portion arranged adjacent to the distal end;
an interface arranged between the proximal end and the distal end, the interface comprising an outermost drive portion spaced from the axis at a first interface distance; and
a resilient arm extending from the proximal end of the shank to an arm end, the resilient arm comprising an outer arm surface facing away from the axis, the resilient arm being movable relative to the axis between:
 a first position where the outer arm surface is spaced from the axis at a first arm distance greater than the first interface distance, and
 a second position where the outer arm surface is spaced from the axis at a second arm distance less than the first arm distance; and
wherein the resilient arm further comprises an aligning element at the arm end configured to promote at least partial rotation of the drill bit about the axis as the resilient arm moves from the first position to the second position in response to force applied to the handle as the drill bit end effector assembly is attached to the surgical instrument.

XI. The end effector assembly as set forth in any one of clauses IX-X, wherein at least a portion of the tip protector is resiliently deformable.

XII. The end effector assembly as set forth in any one of clauses IX-XI, wherein the receiver is configured to receive drill bit cutting tip portions of different sizes.

XIII. The end effector assembly as set forth in any one of clauses IX-XII, wherein the drill bit is formed from a ferromagnetic material; and wherein the tip protector further comprises a magnet capable of holding the cutting tip portion of the drill bit within the receiver.

XIV. An end effector assembly for releasably attaching to a drive assembly of a surgical instrument, the end effector assembly comprising:
a drill bit extending along an axis between a cutting tip portion and an insertion portion; and
a tip protector removably coupled to the cutting tip portion of the drill bit for allowing a user to handle the drill bit without contacting the cutting tip portion.

XV. A method for mounting a drill bit on a surgical instrument having a drive assembly, the drill bit having an insertion portion and a cutting tip portion removably coupled to a tip protector, the method comprising:

grasping the tip protector; and inserting the insertion portion of the drill bit into the surgical instrument such that the drill bit rotates relative to at least a portion of the tip protector when the drill bit is coupled to the drive assembly.

XVI. The method as set forth in clause XV, wherein the step of inserting the insertion portion of the drill bit into the surgical instrument comprises rotating a receiver of the tip protector holding the cutting tip portion of the drill bit relative to a handle of the tip protector.

XVII. The method as set forth in any one of clauses XV-XVI, further comprising axially constraining movement of the drill bit relative to the tip protector.

XVIII. A surgical instrument for use with a drill bit extending along an axis and having a retention surface movable from a first position toward the axis to a second position to facilitate releasably attaching the drill bit to the surgical instrument, the surgical instrument comprising:

a handpiece body;

a drive assembly supported within the handpiece body and comprising a driving cannula configured to axially and rotatably secure the drill bit to the surgical instrument; and a release mechanism configured to facilitate removal of the drill bit from the drive assembly.

XIX. The surgical instrument as set forth in clause XVIII, wherein the release mechanism comprises a slide element arranged for axial translation to facilitate removal of the drill bit from the drive assembly.

XX. The surgical instrument as set forth in clause XIX, wherein the slide element of the release mechanism further comprises an actuating element shaped to engage a resilient arm of the drill bit to urge the resilient arm at least partially toward the axis.

XXI. The surgical instrument as set forth in clause XX, wherein the slide element of the release mechanism further comprises a pocket; and wherein the release mechanism further comprises:

a spherical guide supported within the pocket of the slide element;

a release body comprising a helical slot extending helically about and along the axis; and a collar comprising a collar channel facing toward the axis; and wherein the spherical guide rides along the helical slot formed in the release body and translates along the collar channel formed in the collar to facilitate translation of the slide element along the axis in response to rotation of the collar about the axis to facilitate bringing the actuating element into engagement with the resilient arm of the drill bit such that the drill bit can be removed from the surgical instrument.

XXII. A drill bit comprising:

a shank extending along an axis between a proximal end and a distal end;

a cutting tip portion adjacent to the distal end of the shank;

an interface arranged between the proximal end and the distal end, the interface comprising a first outermost drive portion and a second outermost drive portion spaced from one another to define a maximum drive dimension of the interface, with the first outermost drive portion spaced from the axis at a first interface distance and the second outermost drive portion spaced from the axis at a second interface distance; and a resilient arm extending from the proximal end of the shank to an arm end, the resilient arm comprising an outer arm surface facing away from the axis, and a retention surface facing toward the distal end of the shank and radially aligned about the axis with one of the first and second outermost drive portions, the resilient arm being movable relative to the axis between:

a first position where the outer arm surface is spaced from the axis at a first arm distance, with the first arm distance greater than the first interface distance when the retention surface is radially aligned with the first outermost drive portion, and the first arm distance greater than the second interface distance when the retention surface is radially aligned with the second outermost drive portion, and a second position where the outer arm surface is spaced from the axis at a second arm distance less than the first arm distance, with the second arm distance less than or equal to the first interface distance when the retention surface is radially aligned with the first outermost drive portion, and the second arm distance less than or equal to the second interface distance when the retention surface is radially aligned with the second outermost drive portion.

XXIII. The drill bit as set forth in clause XXII, wherein the first interface distance and the second interface distance comprise a common distance at which each of the first outermost drive portion and the second outermost drive portion is spaced from the axis.

What is claimed is:

1. A drill bit comprising:

a shank extending along an axis between a proximal end and a distal end;

a cutting tip portion adjacent to the distal end of the shank;

an interface arranged between the proximal end and the distal end, the interface comprising at least two outermost drive portions spaced from one another to define a maximum drive dimension of the interface with the at least two outermost drive portions each separately spaced at a first interface distance from the axis; and a resilient arm extending from the proximal end of the shank to an arm end, the resilient arm comprising an outer arm surface facing away from the axis, and a retention surface facing toward the distal end of the shank and radially aligned about the axis with one of the at least two outermost drive portions, the resilient arm being movable relative to the axis between:

a first position where the outer arm surface is spaced from the axis at a first arm distance greater than the first interface distance, and a second position where the outer arm surface is spaced from the axis at a second arm distance less than the first arm distance and less than or equal to the first interface distance.

2. The drill bit as set forth in claim 1, wherein the interface comprises at least four planar surfaces.

3. The drill bit as set forth in claim 2, wherein the interface comprises six planar surfaces.

4. The drill bit as set forth in claim 1, wherein the interface comprises at least four corners with two of the corners defining the at least two outermost drive portions.

5. The drill bit as set forth in claim 4, wherein the interface comprises at least six corners.

6. The drill bit as set forth in claim 1, wherein the interface comprises a plurality of drive lobes with two of the drive lobes defining the at least two outermost drive portions.

7. The drill bit as set forth in claim 6, wherein the plurality of drive lobes comprises four or more drive lobes.

8. The drill bit as set forth in claim 6, wherein the resilient arm and one of the drive lobes comprise a common bisecting plane intersecting the axis to define two equal portions of the resilient arm and two equal portions of at least one of the at least two outermost drive portions.

9. The drill bit as set forth in claim 1, wherein the resilient arm is further defined as a first resilient arm; and further comprising a second resilient arm extending from the proximal end of the shank to a second arm end, the second resilient arm comprising a second outer arm surface facing away from the axis, and a second retention surface facing toward the distal end of the shank and radially aligned about the axis with one of the at least two outermost drive portions; and wherein the first and second resilient arms are each respectively movable relative to the axis between:

respective first positions where the respective outer arm surfaces are spaced from the axis at respective first arm distances greater than the first interface distance, and respective second positions where the respective outer arm surfaces are spaced from the axis at respective second arm distances less than the respective first arm distances and less than or equal to the first interface distance.

10. The drill bit as set forth in claim 1, wherein the resilient arm extends at least partially away from the axis from the proximal end of the shank to the arm end.

11. The drill bit as set forth in claim 1, wherein the resilient arm comprises a finger portion at the arm end, the finger portion providing the retention surface.

12. The drill bit as set forth in claim 11, wherein the finger portion forms a ramp surface configured to deflect the resilient arm toward the axis.

13. The drill bit as set forth in claim 1, wherein the interface extends along the axis between a distal interface end and a proximal interface end, with an interface length defined between the distal interface end and the proximal interface end; and wherein the retention surface is spaced from the proximal interface end at a retention distance greater than or equal to the interface length.

14. The drill bit as set forth in claim 1, wherein the interface extends along the axis between a distal interface end and a proximal interface end, with an interface length defined between the distal interface end and the proximal interface end; and wherein the shank has a shank length defined between the distal end and the proximal end, with the shank length being greater than or equal to three times the interface length.

15. The drill bit as set forth in claim 1, wherein the drill bit is cannulated.

16. The drill bit as set forth in claim 1, wherein the drill bit is a twist drill bit.

17. The drill bit as set forth in claim 1, wherein the resilient arm and one of the at least two outermost drive portions are radially positioned within fifteen degrees of one another relative to the axis.

18. The drill bit as set forth in claim 1, wherein the retention surface and one of the at least two outermost drive portions comprise a common bisecting plane intersecting the axis to define two equal portions of the resilient arm and two equal portions of one of the at least two outermost drive portions.

19. A drill bit comprising:

a shank extending along an axis between a proximal end and a distal end;

a cutting tip portion adjacent to the distal end of the shank;

an interface arranged between the proximal end and the distal end, the interface comprising at least two outermost drive portions spaced from one another to define a maximum drive dimension of the interface with each of the at least two outermost drive portions separately spaced at a first interface distance from the axis; and a resilient arm extending from the proximal end of the shank to an arm end, the resilient arm comprising an outer arm surface facing away from the axis, and a retention surface facing toward the distal end of the shank, the resilient arm being movable relative to the axis between:

a first position where the outer arm surface is spaced from the axis at a first arm distance greater than the first interface distance, and a second position where the outer arm surface is spaced from the axis at a second arm distance less than the first arm distance and less than or equal to the first interface distance;

wherein the retention surface comprises a first bisecting plane that intersects the axis to define two equal portions of the retention surface;

wherein one of the outermost drive portions comprises a second bisecting plane that intersects the axis to define two equal portions of at least one of the at least two outermost drive portions; and wherein the second bisecting plane is radially spaced approximately 60 degrees from the first bisecting plane about the axis.

20. A drill bit comprising:

a shank extending along an axis between a proximal end and a distal end;

a cutting tip portion adjacent to the distal end of the shank;

an interface arranged between the proximal end and the distal end, the interface comprising at least two outermost drive portions spaced from one another to define a maximum drive dimension of the interface with the at least two outermost drive portions each separately spaced at a first interface distance from the axis, and the interface further comprising at least two outer non-drive portions spaced diametrically from one another relative to the axis to define a minimum interface dimension, the two outer non-drive portions being radially spaced from the at least two outermost drive portions about the axis;

a resilient arm extending from the proximal end of the shank to an arm end, the resilient arm comprising an outer arm surface facing away from the axis, and a retention surface facing toward the distal end of the shank and radially aligned about the axis with one of the at least two outermost drive portions, the resilient arm being movable relative to the axis between:

a first position where the outer arm surface is spaced from the axis at a first arm distance greater than the first interface distance, and a second position where the outer arm surface is spaced from the axis at a second arm distance less than the first arm distance and less than or equal to the first interface distance.

21. The drill bit as set forth in claim 20, wherein the interface comprises at least four planar surfaces.

22. The drill bit as set forth in claim 20, wherein the interface comprises at least four corners with two of the corners defining the at least two outermost drive portions.

23. The drill bit as set forth in claim 20, wherein the interface comprises a plurality of drive lobes with two of the drive lobes defining the at least two outermost drive portions.

24. The drill bit as set forth in claim 23, wherein the plurality of drive lobes comprises four or more drive lobes.

25. The drill bit as set forth in claim 20, wherein the resilient arm is further defined as a first resilient arm; and
further comprising a second resilient arm extending from the proximal end of the shank to a second arm end, the second resilient arm comprising a second outer arm surface facing away from the axis, and a second retention surface facing toward the distal end of the shank and radially aligned about the axis with one of the at least two outermost drive portions; and
wherein the first and second resilient arms are each respectively movable relative to the axis between:
respective first positions where the respective outer arm surfaces are spaced from the axis at respective first arm distances greater than the first interface distance, and
respective second positions where the respective outer arm surfaces are spaced from the axis at respective second arm distances less than the respective first arm distances and less than or equal to the first interface distance.

26. The drill bit as set forth in claim 20, wherein the resilient arm extends at least partially away from the axis from the proximal end of the shank to the arm end.

27. The drill bit as set forth in claim 26, wherein the resilient arm comprises a finger portion at the arm end, the finger portion providing the retention surface.

28. The drill bit as set forth in claim 27, wherein the finger portion forms a ramp surface configured to deflect the resilient arm toward the axis.

29. A drill bit comprising:
a shank extending along an axis between a proximal end and a distal end;
a cutting tip portion adjacent to the distal end of the shank;
an interface arranged between the proximal end and the distal end, the interface comprising at least one outermost drive portion spaced at a first interface distance from the axis; and
a resilient arm extending from the proximal end of the shank to an arm end, the resilient arm comprising an outer arm surface facing away from the axis, and a retention surface facing toward the distal end of the shank and radially aligned about the axis with respect to the outermost drive portion at an angle of approximately 0-degrees, 60-degrees, 120-degrees, or 180-degrees, the resilient arm being movable relative to the axis between:
a first position where the outer arm surface is spaced from the axis at a first arm distance greater than the first interface distance, and
a second position where the outer arm surface is spaced from the axis at a second arm distance less than the first arm distance and less than or equal to the first interface distance.

* * * * *